US 7,081,529 B2
United States Patent
Smith et al.

(10) Patent No.: US 7,081,529 B2
(45) Date of Patent: Jul. 25, 2006

(54) RECOMBINANT VACCINE AGAINST BOTULINUM NEUROTOXIN

(75) Inventors: Leonard A. Smith, Clarksburg, MD (US); Michael P. Byrne, New Market, MD (US); John L. Middlebrook, Middletown, MD (US); Hugh Lapenotiere, Charlestown, WV (US); Michael A. Clayton, Mt. Airy, MD (US); Douglas R. Brown, Githersburg, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/910,186

(22) Filed: Jul. 20, 2001

(65) Prior Publication Data
US 2003/0009025 A1    Jan. 9, 2003

Related U.S. Application Data

(63) Continuation of application No. 09/611,419, filed on Jul. 6, 2000, which is a continuation of application No. PCT/US00/12890, filed on May 12, 2000, which is a continuation-in-part of application No. 08/123,975, filed on Sep. 21, 1993, now abandoned.

(60) Provisional application No. 60/146,192, filed on Jul. 29, 1999, provisional application No. 60/133,866, filed on May 12, 1999, provisional application No. 60/133,868, filed on May 12, 1999, provisional application No. 60/133,869, filed on May 12, 1999, provisional application No. 60/133,865, filed on May 12, 1999, provisional application No. 60/133,873, filed on May 12, 1999, provisional application No. 60/133,867, filed on May 12, 1999.

(51) Int. Cl.
C07H 21/04    (2006.01)

(52) U.S. Cl. .................. 536/23.7; 514/44; 435/69.1

(58) Field of Classification Search .................. 514/44, 514/12; 536/23.1, 23.7, 23.4; 435/69.1, 435/6, 252.3, 325, 252.1, 69.3, 320, 70.1, 435/71.1, 71.2, 69.7, 252.35, 320.1, 7.2, 435/254.3, 348; 424/190.1, 183.1, 194.1, 424/234.1, 260.1, 199.1, 186.1; 530/350
See application file for complete search history.

(56) References Cited

U.S. PATENT DOCUMENTS

| 5,601,823 | A | 2/1997 | Williams et al. |
| 5,916,193 | A | 6/1999 | Stevens et al. |
| 5,919,665 | A * | 7/1999 | Williams .................... 435/71.1 |

(Continued)

FOREIGN PATENT DOCUMENTS

WO    98/08540    *    3/1998

(Continued)

OTHER PUBLICATIONS

Binz, T et al, Journal of biological chemistry, vol. 265(16), pp. 9153-9158, Jun. 5.*

(Continued)

Primary Examiner—Lynette R. F. Smith
Assistant Examiner—Ginny Allen Portner
(74) Attorney, Agent, or Firm—Elizabeth Arwine

(57) ABSTRACT

This invention is directed to preparation and expression of synthetic genes encoding polypeptides containing protective epitopes of botulinum neurotoxin (BoNT). The invention is also directed to production of immunogenic peptides encoded by the synthetic genes, as weel as recovery and purification of the immunogenic peptides from recombinant organisms. The invention is also directed to methods of vaccination against botulism using the expressed peptides.

17 Claims, 22 Drawing Sheets

A: BoNTB(H$_c$) synthetic gene SEQ ID NO: 7

```
GAATTCACGatgGCCAACAAATACAATTCCGAAATCCTGAACAATATCAT
CCTGAAACCTGCGTTACAAAGACAACAATCTGATCGATCTGTCTGGTTACG
GTGCTAAAGTTGAAGTATACGACGGTGTTGAACTGAATGACAAGAACCA
GTTCAAACTGACCTCTTCCGCTAACTCTAAGATCCGTGTTACTCAGAATC
AGAACATCATCTTCAACTCCGTATTCCTGGACTTCTCTGTTTCCTTCTGGA
TTCGTATCCCXAAATACAAGAACGACGGTATCCAGAATTACATCCACAA
TGAATACACCATCATCAACTGCATGAAGAATAACTCTGGTTGGAAGATC
TCCATCCGCGGTAACCGTATCATCTGGACTCTGATCGATATCAACGGTAA
GACCCAAATCTGTATTCTTCGAATACAACATCCGTGAAGACATCTCTGAAT
ACATCAATCGCTGGTTCTTCGTTACCATCACCAATAACCTGAACAATGCT
AAAATCTACATCAACGGTAAACTGGAATCTAATACCGACATCAAAGACA
TCCGTGAAGTTATCGCTAACCGGTGAAATCATCTTCAAACTGGACGGTGA
CATCGATCGTACCCAGTTCATCTGGATGAAATACTTCTCCATCTTCAACA
CCGAACTGTCTCAGTCCAATATCGAAGAACGGTACAAGATCCAGTCTTA
CTCCGAATACCTGAAAGACTTCTGGGGTAATCCGCTGATGTACAACAAA
GAATACTATATGTTCAATGCTGGTAACAAGAACTCTTACATCAAACTGA
AGAAAGACTCTCCGGTTGGTGAAATCCTGACTCGTTCCAAATACAACCA
GAACTCTAAATACATCAACTACCGCGACCTGTACATCGGTGAAAAGTTC
ATCATCCGTCGCAAATCTAACTCTCAGTCCATCAATGATGACATCGTACG
TAAAGAAGACTACATCTACCTGACTTCTTCAACCTGAATCAGGAATGG
CGTGTATACACCTACAAGTACTTCAAGAAAGAAGAAGAAAAGCTTTTCC
TGGCTCCGATCTCTGATTCCGACGAACTCTACAACACCATCCAGATCAAA
GAATACGACGAACAGCCGAACTACTCTTGCCAGCTGCTGTTCAAGAAAG
ATGAAGAATCTACTGACGAAATCGGTCTGATCGGTATCCACCCGTTTCTAC
GAATCTGGTATCGTATTCGAAGAATACAAAGACTACTTCTGCATCTCCAA
ATGGTACCTGAAGGAAGTTAAACGCAAACCGTACAACCTGAAAACTGGGT
TGCAATTGGCAGTTCATCCCGAAAGACGAAGGTTGGACCGAAtagtaaGAA
TTC
```

B: BoNTB(H$_c$) encoded protein SEQ ID NO: 8

```
MANKYNSEILNNILNLRYKDNNLIDLSGYGAKVEVYDGVELNDKNQFKLT
SSANSKIRVTQNQNIIFNSVFLDFSVSFWIREPKYKNDGIQNYIHNEYTIINCM
KNNSOWKISIRGNRIIWTLIDINGKTKSVFEYNIREDISEYINRWFFVTITNNL
NNAKIYINGKLESNTDKDIREVIANGEIFKLLDGDIDRTQFIWMKYFSIFNTEL
SQSNIEERYKIQSYSEYLKDFWGNPLMYNKEYYMFNAGNKNSYIKLKKDSP
VGEILTRSKYNQNSKYINYRDLYIGEKFIIRRKSNSQSINDDIVRKEDYIYLDF
FNLNQEWRVYTYKYFKKEEEKLFLAPISDSDELYNTIQIKEYDEQPTYSCQL
LFKKDEESTDEIGLIGIHRFYESGIVFEEYKDYFCISKWYLKEVKRKPYNLKL
GCNWQFIPKDEGWTE**
```

U.S. PATENT DOCUMENTS

| | | | | |
|---|---|---|---|---|
| 5,939,070 | A * | 8/1999 | Johnson et al. | 424/194.1 |
| 5,989,545 | A * | 11/1999 | Foster et al. | 424/183.1 |
| 6,214,602 | B1 * | 4/2001 | Zdanovsky | 435/252.3 |
| 6,270,777 | B1 * | 8/2001 | Sokol et al. | 424/260.1 |
| 6,287,566 | B1 * | 9/2001 | Dertzbaugh | 424/190.1 |
| 6,461,617 | B1 * | 10/2002 | Shone et al. | 424/236.1 |
| 6,495,143 | B1 | 12/2002 | Lee et al. | |
| 6,521,235 | B1 * | 2/2003 | Johnston et al. | 424/199.1 |
| 6,713,444 | B1 * | 3/2004 | Garcia et al. | 514/2 |

FOREIGN PATENT DOCUMENTS

| | | |
|---|---|---|
| WO | 9715394 | 5/1998 |
| WO | 0012890 | 11/2000 |

OTHER PUBLICATIONS

Campbell, KD et al, J. Clin. Microbiol. 1993, Sep., vol. 31(9), pagtes 2255-2262.*

Campbell, K et al, Biochim Biophys ACTA, 1993, Dec. 14, vol. 1216(3), pp. 487-491.*

Dasgupta, Bibhuti R et al, Biochimie, vol. 70, pp. 811-817, 1988.*

East, AK et al, International Journal of Systematic Bacteriology, Voo. 46(4), pp. 1105-1112, Oct. 1996.*

Evans, DM e tal, Eur. J. Biochem, vol. 154, pp. 409-416, 1986.*

Fach, P et al, Applied and Environmental Microbiology, Jan. 1995, pp. 389-392, vol. 61(1).*

Fujinage, Y et al, vol. 213(3), pp. 737-745, Aug. 24, 1995.*

Halpern, JL et al, Journal of Biological Chemistry, vol. 268(15), May 25, 1993, pp. 11188-11192.*

Hutson, RA et al, Curr. Microbiol. 1994, Voo. 28(2), pates 101-110.*

Jung, HH et al, FEMS Microbiol. Lett, Feb. 1, 1992, vol. 91, pp. 69-72.*

Szabo, EA et al. AppOl. Environ Microbiol. Sep. 1993, vol. 59(9), pp. 3011-3020.*

Thompson, DE et al, FEMS Microbiol Lett. 1993, Apr. 1, vol. 108(2), pp. 175-182.*

Thompson, De et al, Eur. J. Biochem, vol. 189, pp. 73-81, 1990.*

Whelan, Sarah M. et al, applied and Environmental Microbiology, Aug. 1992, Vol. 58(8), pp. 2345-2354.*

Whelan et al (reference of record), App & Environmental Microbiol, Aug. 1992, vol. 58(8), p. 2345-2356.*

Smith et al (reference of record), Toxicon, vol. 36 (11) pp. 1539-1548, 1998.*

Halpern et al (reference of record) May 1993, J. Biol. Chem., vol. 268(15), May 25, p. 11188-11192.*

Ahmed SA et al., 2001, "Enzymatic autocatalysis of botulinum A neurotoxin light chain" *J. Protein Chem.* 20(3):221-231.

Schmidt JJ et al., 2001, "High-throughput assays for botulinum neurotoxin proteolytic activity: serotypes A, B, D, and F" *Analytical Biochemistry* 296:130-137.

URL:http://www.cdc.gov/ncidod/srp/drugservice/immuodrugs.htm, 2001, "Immunobiologic Agents and Drugs Available from the Centers for Disease Control. Descriptions, Recommendations, Adverse Reactions and Serologic Response" Centers for Disease Control, Atlanta, GA.

Ahmed SA et al., 2000, "Light chain of botulinum A neurotoxin expressed as an inclusion body from a synthetic gene is catalytically and functionally active" *J. Protein Chem.* 19(6):475-487.

Alderton JM et al., 2000, "Evidence for a vesicle-mediated maintenance of store-operated calcium channels in human embryoinic kidney cell line" *Cell Calcium* 28(3):161-169.

Byrne MP et al., 2000, "Fermentation, purification, and efficacy of a recombinant vaccine candidiate against botulinum neurotoxin type F from *Pichia pastoris*" *Protein Expr Purif.* 18(3):327-337.

Dalbey RE et al., 2000, "Evolutionarily related insertion pathways of bacterial, mitochondrial, and thylakoid membrane proteins" *Annu. Rev. Cell Dev. Biol.* 16:51-87.

Ettinger RA et al., 2000, "Beta 57-Asp plays an essential role in the unique SDS stability of HLA-DQA1*0102/DQB1*0602 alpha beta protein dimer, the class II MHC allele associated with protection from insulin-dependent diabetes mellitus" *J. Immunol* 165:3232-3238.

Kadkhodayan S et al., 2000, "Cloning, expression, and one-step purfication of the minimal essential domain of the light chain of botulinum neurotoxin type A" *Protein Expr. Purif.* 19(1):125-130.

Knapp M et al., 2000, "The crystal structure of botulinum toxin A zinc protease domain." Presented at teh 37th Annual Meeting of the Interagency Botulinum Research Coordinating Committee, Oct. 17-20, 2000, Alisomar, California.

Li L et al., 2000, "Role of zinc binding in type A botulinum neurotoxin light chain's toxic structure" *Biochemistry* 39:10581-10586.

Strasser A et al., 2000, "Apoptosis signaling" *Annu. Rev. Biochem* 69:217-245.

Cai S et al., 1999, "Enhancement of the endopeptidase activity of botulinum neurotoxin by its associated proteins and dithiothreitol" *Biochemistry* 38:6903-6910.

Caliborne A et al., 1999, "Protein-sulfenic acids: diverse roles for an unlikely player in enzyme catalysis and redox regulation" *Biochemistry* 38:15407-15416.

Lacy DB et al., 2999, "Sequence homology and structural analysis of the clostridial neurotoxins" *J. Mol. Biol.* 291:1091-1104.

Li L et al., 1999, "High-level expression, purification, and characterization of recombinant type A botulinum neurotoxin light chain" *Protein Expr. Purif.* 17:339-344.

Li L et al., 1000, "In vitro translation of type A Clostridium botulinum neurotoxin heavy chain an analysis of its binding to rat synaptosomes" *J Protein Chem.* 18(1):89-95.

Byrne MP et al., 1998, "Purification, Potency, and Efficacy of the Botulinum Neurotoxin Type A Binding Domain from *Pichia pastoris* as a Recombinant Vaccine Candidate," *Infect. Immun.* 66:4817-4822.

Fu F et al., 1998, "Role of zinc in the structure and toxic activity of botulinum neurotoxin" *Biochemistry* 37:5267-5278.

Lacy DB et al., 1998, "Crystal Structure of Botulinum Neurotoxin Type A and Implications for Toxicity," *Nat. Struct. Biol.* 5:898-902.

Nowakowski JL et al., 1998, "Production of an expression system for a synaptobrevin fragment to monitor cleavage by botulinum neurotoxin B" *J. Protein Chem.* 17:453-462.

Potter KJ et al., 1998, "Production and purification of the heavy-chain fragment C of botulinum neurotoxin, serotype B, expressed in the methylotrophic yeast *Pichia pastoris*" *Protein Expr Purif.* 13(3):357-365.

Schmidt JJ et al., 1998, "Type A botulinum neurotoxin proteolytic activity: development of competitive inhibitors and implications for substrate specificity at the S1' binding subsite" *FEBS Lett.* 435:61-64.

Smith LA, 1998, "Development of recombinant vaccines for botulinum neurotoxin" *Toxicon.* 36(11):1539-48.

Adler M et al., 1997, "Protection by the heavy metal chelator N,N,N', N'-tetrakis (2-pyridylmethyl)ethylenediamine (TPEN) against the lethal action of botulinum neurotoxin A and B" *Toxicon* 35:1089-1100.

Brown DR et al., 1997, "Identification and Characterization of a Neutralizing Monoclonal Antibody Against Botulinum Neurotoxin, Serotype F, Following Vaccination with Active Toxin," *Hybridoma*, 16:447-456.

Chen F et al., 1997 "Antibody mapping to domains of botulinum neurotoxin serotype A in the complexed and uncomplexed forms" *Infect. Immun.* 65:1626-1630

Chiruvolu V et al., 1997, Recombinant Protein Expression in an Alcohol Oxidase-Defective Strain of *Pichia pastoris* in Feed-Batch Fermentations, *Enzyme Microbiol. Technol.* 21:277-283.

Kiyatkin N et al., 1997, "Induction of an immune response by oral administration of recombinant botulinum toxin" *Infect. Immun.* 65:4586-4591.

Lebeda FJ et al., 1997, "Predicting Differential Antigen-Antibody Contact Regions Based on Solvent Accessibility," *J. Protein Chem.* 16:607-618.

Schmidt JJ et al., 1997, "Endoproteinase activity of type A botulinum neurotoxin: substrate requirements and activation by serum albumin" *J. Protein Chem.* 16(1):19-26.

Sheridan RE et al., 1997, "Structural features of aminoquinolines necessary for antagonist activity against botulinum neurotoxin" *Toxicon* 35:1439-1451.

Washbourne P et al., 1997, "Botulinum neurotoxin types A and E require the SNARE motif in SNAP-25 for proteolysis" *FEBS Lett.* 418:1-5.

Dertzbaugh MT et al., 1996, "Mapping of protective and cross-reactive domains of the type A neurotoxin of Clostridium botulinum" *Vaccine* 14:1538-1544.

Foran P et al., 1996, "Botulinum neurotoxin C1 cleaves both syntaxin and SNAP-25 in intact and permeabilized chromaffin cells: correlation with its blockade of catecholomine release" *Biochemistry* 35:2630-2636.

Auld DS, 1995, "Removal and replacement of metal ions in metallopeptidases" *Meth. Enzymol.* 248:228-242.

Bi GQ et al., 1995, "Calcium-regulated exocytosis is required for cell membrane resealing" *J. Cel Biol.* 131:1747-1758.

Cardoso F et al., 1995, "Clinical use of botulinum neurotoxins". In *Current Topics in Microbiology and Immunology* (Capron A et al., eds.), Springer-Verlag, Germany, 195:123-141.

Clayton MA et al., 1995, "Protective vaccination with a recombinant fragment of Clostridium botulinum neurotoxin serotype A expressed from a synthetic gene in *Escherichia coli*" *Infect Immun.* 63(7):2738-2742.

Klatt P et al., 1995, "Structural analysis of porcine brain nitric oxide synthase reveals a role for tetrahydrobiopterin and L-arginine in the formation of an SDS-resistant dimer" *EMBO J.* 14:3687 3695.

LaPenotiere HF et al., 1995, "Expression of a large, nontoxic fragment of botulinum neurotoxin serotype A and its use as an immunogen" *Toxicon.* 33(10):1383-1386.

Montecucco C et al., 1995, "Structure and function of tetanus and botulinum neurotoxins" *Q. Rev. Biophys.* 28:423-472.

Oguma K et al., 1995, "Structure and Function of *Clostridium botulinum* Toxin" *Microbiol. Immunol.* 39:161-168.

Pace CN et al., 1995, "How to measure and predict the molar absorption coefficient of a protein" *Protein Sci.* 4:2411-2423.

Romanos MA et al., 1995, "Expression of Cloned Genes in Yeast," *DNA Cloning 2: Expression Systems*, (Glover D., et al., Eds), Oxford Univ. Press, London, pp. 123-167.

Schiavo G et al., 1995, "Intracellular targets and metalloprotease activity of tetanus and botulinum neurotoxins." In *Clostridial Neurotoxins: The Molecular Pathogenesis of Tetanus and Botulism* (Montecucco, C., ed.), Springer, New York, pp. 257-273.

Schmidt JJ et al., 1995, "Proteolysis of synthetic peptides by type A botulinum neurotoxin" *J. Protein Chem.* 14(8):703-708.

Shone CC et al., 1995, "Growth of clostridia and preparation of their neurotoxins" *Curr. Top. Microbiol. Immunol.* 195:143-160.

Zhou L et al., 1995, "Expression and purificaiton of the light chain of botulinum neurotoxin A: a single mutation abolishes its cleavage of SNAP-25 and neurotoxicity after reconstitution with the heavy chain" *Biochemistry* 34(46):15175-15181.

Foran P et al., 1994, "Differences in the protease activities of tetanus and botulinum B toxins revealed by the cleavage of vesicle-associated membrne protein and various sized fragments" *Biochemistry* 33:15365-15374.

Krieglstein KG et al., 1994, "Covalent structure of botulinum neurotoxin type A: location of sulfhydryl groups, and disulfide bridges and identification of C-termini of light and heavy chains" *J. Protein Chem.* 13:49-57.

Lebeda FJ et al.: 1994, "Secondary structural predictions for teh clostridial neurotoxins" *Proteins* 20:293-300.

Li Y et al., 1994, "A single mutation in the recombinant light chain of tetanus toxin abolishes its proteolytic activity and removes the toxicity seen after reconstitution with native heavy chain" *Biochemistry* 33:7014-7020.

Montecucco C et al., 1994, "Mechanism of action of tetanus and botulinum neurotoxins" *Mol. Microbiol.* 13:1-8.

Nishiki TI et al., 1994, "Identification of Protein Receptor for *Clostridium botulinum* Type B Neurotoxin in Rat Brain Synaptosomes"*J. Biol. Chem.* 269:10498-10503.

Rossetto O et al., 1994, "SNARE motif and neurotoxins" *Nature* 372:415-416.

Schiavo G et al., 1994, "Botulinum G neurotoxin cleaves VAMP/synaptobrevin at a single Ala—Ala peptide bond" *J. Biol. Chem.* 269:20213-20216.

Scorer CA et al., 1994, "Rapid Selection Using G418 of High Copy Number Transformants of *Pichia pastoris* for High-Level Foreign Gene Expression," *Bio/Technology*, 12:181-184.

Shone CC et al., 1994, "Peptide substrate specificity and properties of the zinc-endopeptidase activity of botulinum type B neurotoxin" *Eur. J. Biochem.* 225:263-270.

Steinhardt RA et al., 1994, "Cell membrane resealing by a vesicular mechanism similar to neurotransmitter release" *Science* 263:390-393.

Baltz RH et al., eds., 1993, *Industrial Microorganisms: Basic and Applied Molecular Genetics*, American Society for Microbiology, Washington, D.C., pp. 122-126.

Blasi J et al., 1993, "Botulinum neurotoxin A selectively cleaves the synaptic protein SNAP-25" *Nature* 365:160-163.

Campbell KD et al., 1993, "Gene probes for identification of the botulinal neurotoxin gene and specific identification of neurotoxin types B, E, and F" *J. Clin Microbiol.* 31(9):2255-2262.

Cregg JM et al., 1993, "Recent Advances in the Expression of Foreign Genes in *Pichia pastoris*," *Bio/Technology*, 11:905-910.

de Paiva A et al., 1993, "A role for the interchain disulfide or its participting thiols in the internalization of botulinum neurotoxin A revealed by a toxin derivative that binds to ecto-acceptors and inhibits transmitter release intracellularly" *J. Biol. Chem.* 268:20838-20844.

Dertzbaugh M et al., May 1993, "Cloning and Expression of Peptides derived from the botulinum neurotoxin serotype A gene" 93rd American Society for Microbiology General Meeting, Atlanta, GA, Session 334, E-105, p. 161.

Gimenez JA et al., 1993, "Boutilinum Type A neurotoxin disgested with pepsin yields 132, 97, 72, 45, 42, and 18 kD fragments" *J Protein Chem.* 12(3):351-363.

LaPenotiere HF et al., 1993, "Development of a molecular engineered vaccine for C. botulinum neurotoxins" in Botulinum and Tetnus Toxin (DasGupta BR, ed.) Plenum Press, New York.

Schiavo G et al., 1993, "Identification of the Nerve Termianl Targets of Botulinum Neurotoxin Serotypes, A, D, and E"*J. Biol. Chem.* 268:23784-23787.

Shone CC et al., 1993, "Proteolytic Cleavage of Synthetic Fragments of Vesicle-Associated Membrane Protein, Isoform-2 by Botulinum Type B Neurotoxin"*Eur. J. Biochem.* 217:965-971.

Simpson LL et al., 1993, "Chelation of zinc antagonizes the neuromuscular blocking properties of the seven serotypes of botulinum neurotoxin as well as tetanus toxin" *J. Pharmacol. Exp. Ther.* 267:720-727.

Sreekrishna K, 1993, "Strategies for Optimizing Protein Expression and Secretion in the Methylotrophic Yeast *Pichia pastoris*, "*Industrial Micororganisms: Basic and Applied Molecular Genetics*, Baltz, R. H. et al., Eds.), pp. 119-126, Am. Soc. Microbiol., Washington, DC.

Ahmed SA et al., 1992, "Active-site structural comparison of streptococcal NADH peroxidase and NADH oxidase. Reconstitution with artificial flavins" *J. Biol. Chem.* 267:3832-3840.

Kurazono H et al., 1992, "Minimal essential domains specifying toxicity of the light chains of tetanus toxin and botulinum neurotoxin type A" *J Biol chem.* 267(21):14721-14729.

Montal MS et al., 1992, "Identification of an Ion Channel-Forming Motif in the Primary Structure of Tetanus and Botulinum Neurotoxins"*FEBS* 313:12-18.

Romanos MA et al., 1992, "Foreign Gene Expression in Yeast: A Review," *Yeast*, 8:423-488.

Schiavo G et al., 1992, "Tetanus and Botulinum-B Neurotoxins Block Neurotransmitter Release by Proteolytic Cleavage of Synaptobrevin"*Nature* 359:832-835.

Schiavo G et al., 1992, "Tetanus Toxin is a Zinc Protein and its Inhibition of Neurotransmitter Release and Protease Activity Depend on Zinc"*EMBO J.* 11:3577-3583.

Whelan SM et al., 1992, "Molecular cloning of the Clostridium botulinum structural gene encoding the type B neurotoxin and determination of its entire nucleotide sequence" *Appl. Environ. Microbiol.* 58:2345-2354.

Clare JJ et al., 1991, "High-Level Expression of Tetanus Toxin Fragment C in *Pichia pastoris* Strains Contining Multiple Tandem Integrations of the Gene," *Bio/Technology* 9:455-460.

Niemann H et al., 1991, "Clostridial neurotoxins: from toxins to therapeutic tools?" *Behring Inst Mitt.* 89:153-162.

Poulain B et al., 1991, "Heterologous Combinations of Heavy and Light Chains from Botulinum Neurotoxin A and Tetanus Toxin Inhibit Neurotransmitter Release in *Aplysia*"*J. Biol. Chem.* 266:9580-9585.

Romanos MA, et al., 1991, "Expression of Tetanus Toxin Fragment C in Yeast: Gene Synthesis is Required to Eliminate Fortuitous Polyadenylation Sites in AT-rich DNA," *Nucleic Acids Res.* 19:1461-1467.

Ahnert-Hilger G et al.,1990, "Chains and fragments of tetanus toxin, and their contribution to toxicity" *J Physiol* (Paris) 84(3):229-236.

Andersson SG et al., 1990, "Codon preferences in free-living microorganisms" *Microbial. Rev.* 54(2):198-210.

DasGupta BR et al., 1990, "Botulinum neurotoxin type A: sequence of amino acids at the N-terminus and around the nicking site" *Biochemie* 72:661-664.

Dekleva ML et al., 1990, "Purification and characterization of a protease from Clostridium botulinum type A that nicks single-chain type A botulinum neurotoxin into the di-chain form " *J. Bacteriol.* 172:2498-2503.

Thompson DE et al., 1990, "The complete amino acid sequence of the Clostridium botulinum type A neurotoxin, deduced by nucleotide sequence analysis of the encoding gene" *Eur. J. Biochem.* 189:73-81.

Wadsworth JDF et al., 1990, "Botulinum Type F Neurotoxin"*Biochem. J.* 268:123-128.

Bittner MA et al., 1989, "Isolated light chains of botulinum neurotoxins inhibit exocytosis. Studies in digitonin-permeabilized chromaffin cells" *J. Biol. Chem.* 2647:10354-10360.

DasGupta BR et al., 1989, "C. botulinum neurotoxin types A and E: isolated light chain breaks down into two fragments. Comparison of their amino acid sequences with tetanus neurotoxin" *Biochimie* 71:1193-1200.

DasGupta BR, 1989, "The Structure of Botulinum Neurotoxins"*Botulinum Neurotoxin and Tetanus Toxin*, (Simpson, L.L., Ed.) Academic Press, New Yourk, pp. 53-67.

Kozaki S et al., 1989, "Immunological characterization of papain-induced fragments of Clostridium botulinum type A neurotoxin and interaction of the fragments with brain synaptosomes" *Infect Immun.* 57(9):2634-2639.

Kozaki et al., 1989, "Antibodies against Botulism Neurotoxin", L.L. Simpson, ed. Academic Press, New York, pp. 301-318.

Makoff AJ et al., 1989, "Expression of Tetanus Toxin Fragment C in *E. coli*: High Level Expression by Removing Rare Condons," *Nucleic Acids Res.* 17:10191-10201.

Middlebrook JL, 1989, "Cell Surface Receptors for Protein Toxins"*Botulinum Neurotoxins and Tetanus Toxin*, (Simpson, L.L., Ed.) Academic Press, New York, pp. 95-119.

Maisey EA et al., 1988, "Involovement of the constituent chains of botulinum neurotoxin A and B in the blockaede of neurotransmitter release" *Eur. J. Biochem.* 177:683-691.

Sathyamoorthy V et al., 1988, "Botulinum neurotoxin type A: cleavage of the heavy chain into two halves and their partial sequences" *Arch Biochem Biophys.* 266(1):142-151.

Siegel LS, 1988, "Human Immune Response to Botulinum Pentavalent (ABCDE) Toxoid Determined by a Neutralization Test and by an Enzyme-Linked Immunosorbent Assay" *J. Clin. Microbiol.* 26:2351-2356.

Sreekrishna K et al., 1988, "High Level Expression of Heterologous Proteins in Methylotrophic Yeast *Pichia pastoris*," *J. Bas. Microbiol.* 28:265-278.

Winkler HH et al., 1988, "Codon usage in selected AT-rich bacteria" *Biochimie* 70:977-986.

Schagger H et al., 1987, "Tricine-sodium dodecyl sulfate-polyacrylamide gel electrophoresis for the separation of proteins in the range from 1 to 100 kDa" *Anal. Biochem.* 166:368-379.

Shone CC et al., 1987, A 50-kDa Fragment from the NH$_2$-terminus of the Heavy Subunit of *Clostridium botulinum* Type A Neurotoxin Forms Channels in Lipid Vesicles, *Euro. J. Biochem.* 167:175-180.

Sonnabend WF et al, 1987, "Intestinal Toxicoinfectin by *Clostridium botulinum* Type F in an Adult. Case Associated with Guillian-Barre Syndrome" *Lancet* 1:357-361.

Ahmed SA et al., 1986, "Identification of three site of proteolytic cleavage in the hinge region between the two domains of the beta 2 subunit of tryptophan synthase of *Escherichia coli* or Salmonella typhimurium" *Biochemistry* 25, 3118-3124.

Black JD et al., 1986, "Interaction of $^{125}$I-botulinum Neurotoxins with Nerve Terminals. I. Ultrastructural Autoradiographic Localization and Quantitation of Distinct Membrane Acceptors for Types A and B on Motor Nerves" *J. Cell Biol.* 103:521-534.

Habermann E et al., 1986, "Clostridial Neurotoxins: Handling and Action at the Cellular and Molecular Level"*Cur. Top. Microbiol. Immunol.* 129:93-179.

Simpson LL, 1986, "Molecular Pharmacology of Botulinum Toxin and Tetanus Toxin" *Annu. Rev Pharmacol. Toxicol.* 26:427-453.

Cregg JM et al., 1985, "*Pichia pastoris* as a Host System for Transformations," *Mol. Cell. Biol.* 5:3376-3385.

Sathyamoorthy V et al., 1985, "Separation, purification, partial characterization and comparison o the heavy and light chains of botulinum neurotoxin types A, B, and E" *J Biol Chem.* 260(19):10461-10466.

Schmidt JJ et al., 1985, "Partial amino acid sequences of botulinum neurotoxins types B and E" *Arch. Biochem. Biophys.* 238:544-548.

Shone CC et al., 1985, Inactivation of *Clostridium botulinum* Type A Neurotoxin by Trypsin and Purification of Two Tryptic Fragments. Proteolytic Action Near the COOH-terminus of the Heavy Subunit Destroys Toxin-Binding Activiity, *Eur. J. Biochem.* 151:75-82.

Anderson JH et al., 1981, "Clinical Evaluation of Botulinum Toxoids"*Biomedical Aspects of Botulism*, (Lewis, G.E., Ed.) Academic Press, New York, pp. 233-246.

Syuto B et al., 1981, "Separation and characterization of heavy and light chains from *Clostridium botulinum* type C toxin and their reconstitution" *J. Biol. Chem.* 256:3712-3717.

Hatheway CL, 1976, "Toxoid of *Clostridium botulinum* Type F: Purfication and Immunogenicity Studies "*Appl. Environ. Microbiol.* 31:234-242.

DasGupta BR et al., 1972, "A Common Subunit Structure in *Clostridium botulinum* Type A, B, and E Toxins" Biohys. Res. Commun. 48:108-112.

Midura TF et al., 1972, "*Clostridium botulinum* Type F: Isolation from Venison Jerky" *Appl. Microbiol.* 24:165-167.

Laemmli UK, 1970, "Cleavage of structural proteins during the assembly of the head of bacteriophage T4" *Nature* 227:680-685.

van Heyningen WE, 1968, "Tetanus"*Sci. Am.* 218:69-77.

Fiock MA et al., 1963, "Studies of Immunities to Toxins of *Clostridium Botulinum*. IX. Immunologic Response of Man to Purified Pentavalent ABCDE Botulinum Toxoid"*J. Immunol.* 90:697-702.

* cited by examiner

FIGURE 1

A: BoNTA(H$_C$) synthetic gene (Version #1) SEQ ID NO: 1

GAATTCGAAACGatgCGTCTGCTGTCTACCTTCACTGAATACATCAAGAAC
ATCATCAATACCTCCATCCTGAACCTGCGCTACGAATCCAATCACCTGAT
CGACCTGTCTCGCTACGCTTCCAAAATCAACATCGGTTCTAAAGTTAACT
TCGATCCGATCGACAAGAATCAGATCCAGCTGTTCAATCTGGAATCTTCC
AAAATCGAAGTTATCCTGAAGAATGCTATCGTATACAACTCTATGTACG
AAAACTTCTCCACCTCCTTCTGGATCCGTATCCCGAAATACTTCAACTCC
ATCTCTCTGAACAATGAATACACCATCATCAACTGCATGGAAAACAATT
CTGGTTGGAAAGTATCTCTGAACTACGGTGAAATCATCTGGACTCTGCAG
GACACTCAGGAAATCAAACAGCGTGTTGTATTCAAATACTCTCAGATGA
TCAACATCTCTGACTACATCAATCGCTGGATCTTCGTTACCATCACCAAC
AATCGTCTGAATAACTCCAAAATCTACATCAACGGCCGTCTGATCGACC
AGAAACCGATCTCCAATCTGGGTAACATCCACGCTTCTAATAACATCATG
TTCAAACTGGACGGTTGTCGTGACACTCACCGCTACATCTGGATCAAATA
CTTCAATCTGTTCGACAAGAACTGAACGAAAAAGAAATCAAAGACCTG
TACGACAACCAGTCCAATTCTGGTATCCTGAAAGACTTCTGGGGTGACTA
CCTGCAGTACGACAAACCGTACTACATGCTGAATCTGTACGATCCGAAC
AAATACGTTGACGTCAACAATGTAGGTATCCGCGGTTACATGTACCTGA
AAGGTCCGCGTGGTTCTGTTATGACTACCAACATCTACCTGAACTCTTCC
CTGTACCGTGGTACCAAATTCATCATCAAGAAATACGCGTCTGGTAACA
AGGACAATATCGTTCGCAACAATGATCGTGTATACATCAATGTTGTAGTT
AAGAACAAAGAATACCGTCTGGCTACCAATGCTTCTCAGGCTGGTGTAG
AAAAGATCTTGTCTGCTCTGGAAATCCCGGACGTTGGTAATCTGTCTCAG
GTAGTTGTAATGAAATCCAAGAACGACCAGGGTATCACTAACAAATGCA
AAATGAATCTGCAGGACAACAATGGTAACGATATCGGTTTCATCGGTTT
CCACCAGTTCAACAATATCGCTAAACTGGTTGCTTCCAACTGGTACAATC
GTCAGATCGAACGTTCCTCTCGCACTCTGGGTTGCTCTTGGGAGTTCATC
CCGGTTGATGACGGTTGGGGTGAACGTCCGCTGtaaGAATTC B: BoNTA(H$_C$) encoded protein (Version #1) SEQ ID NO: 2

MRLLSTFTEYIKNIINTSILNLRYESNHLIDLSRYASKINIGSKVNFDPIDKNQI
QLFNLESSKIEVILKNAIVYNSMYENFSTSFWIRIPKYFNSISLNNEYTIINCME
NNSGWKVSLNYGEIIWTLQDTQEIKQRVVFKYSQMINISDYINRWIFVTITNN
RLNNSKIYINGRLIDQKPISNLGNIHASNNIMFKLDGCRDTHRYIWIKYFNLF
DKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVRN
NDRVYINVVVKNKEYRLATNASQAGVEKILSALEIPDVGNLSQVVVMKSKN
DQGITNKCKMNLQDNNGNDIGFIGFHQFNNIAKLVASNWYNRQIERSSRTL
GCSWEFIPVDDGWGERPL*

FIGURE 2

A: BoNTA(H$_c$) synthetic gene (version #2) SEQ ID NO: 3

GAATTCGAAACGatgTCTACCTTCACTGAATACATCAAGAACATCATCAAT
ACCTCCATCCTGAACCTGCGCTACGAATCCAATCACCTGATCGACCTGTC
TCGCTACGCTTCCAAAATCAACATCGGTTCTAAAGTTAACTTCGATCCGA
TCGACAAGAATCAGATCCAGCTGTTCAATCTGGAATCTTCCAAAATCGA
AGTTATCCTGAAGAATGCTATCGTATACAACTCTATGTACGAAAACTTCT
CCACCTCCTTCTGGATCCGTATCCCGAAATACTTCAACTCCATCTCTCTG
AACAATGAATACACCATCATCAACTGCATGGAAAACAATTCTGGTTGGA
AAGTATCTCTGAACTACGGTGAAATCATCTGGACTCTGCAGGACACTCA
GGAAATCAAACAGCGTGTTGTATTCAAATACTCTCAGATGATCAACATCT
CTGACTACATCAATCGCTGGATCTTCGTTACCATCACCAACAATCGTCTG
AATAACTCCAAAATCTACATCAACGGCCGTCTGATCGACCAGAAACCGA
TCTCCAATCTGGGTAACATCCACGCTTCTAATAACATCATGTTCAAACTG
GACGGTTGTCGTGACACTCACCGCTACATCTGGATCAAATACTTCAATCT
GTTCGACAAGAACTGAACGAAAAGAAATCAAGACCTGTACGACAA
CCAGTCCAATTCTGGTATCCTGAAAGACTTCTGGGGTGACTACCTGCAGT
ACGACAAACCGTACTACATGCTGAATCTGTACGATCCGAACAAATACGT
TGACGTCAACAATGTAGGTATCCGCGGTTACATGTACCTGAAAGGTCCG
CGTGGTTCTGTTATGACTACCAACATCTACCTGAACTCTTCCCTGTACCG
TGGTACCAAATTCATCATCAAGAAATACGCGTCTGGTAACAAGGACAAT
ATCGTTCGCAACAATGATCGTGTATACATCAATGTTGTAGTTAAGAACAA
AGAATACCGTCTGGCTACCAATGCTTCTCAGGCTGGTGTAGAAAAGATC
TTGTCTGCTCTGGAAATCCCGGACGTTGGTAATCTGTCTCAGGTAGTTGT
AATGAAATCCAAGAACGACCAGGGTATCACTAACAAATGCAAAATGAAT
CTGCAGGACAACAATGGTAACGATATCGGTTTCATCGGTTTCCACCAGTT
CAACAATATCGCTAAACTGGTTGCTTCCAACTGGTACAATCGTCAGATCG
AACGTTCCTCTCGCACTCTGGGTTGCTCTTGGGAGTTCATCCCGGTTGAT
GACGGTTGGGGTGAACGTCCGCTGtaaGAATTC

B: BoNTA(H$_c$) encoded protein (Version #2) SEQ ID NO: 4

MSTFTEYIKNIINTSILNLRYESNHLIDLSRYASKINIGSKVNFDPIDKNQIQLF
NLESSKIEVILKNAIVYNSMYENFSTSFWIRIPKYFNSISLNNEYTIINCMENNS
GWKVSLNYGEIIWTLQDTQEIKQRVVFKYSQMINISDYINRWIFVTITNNRLN
NSKIYINGRLIDQKPISNLGNIHASNNIMFKLDGCRDTHRYIWIKYFNLFDKE
LNEKEIKDLYDNQSNSGILKDFWGDYLQYDKPYYMLNLYDPNKYVDVNNV
GIRGYMYLKGPRGSVMTTNIYLNSSLYRGTKFIIKKYASGNKDNIVRNNDRV
YINVVVKNKEYRLATNASQAGVEKILSALEIPDVGNLSQVVVMKSKNDQGI
TNKCKMNLQDNNGNDIGFIGFHQFNNIAKLVASNWYNRQIERSSRTLGCSW
EFIPVDDGWGERPL*

FIGURE 3

A: BoNTA(H$_c$) synthetic gene (Version #3) SEQ ID NO: 5

GAATTCGAAACGatgGCCTCTACCTTCACTGAATACATCAAGAACATCATC
AATACCTCCATCCTGAACCTGCGCTACGAATCCAATCACCTGATCGACCT
GTCTCGCTACGCTTCCAAAATCAACATCGGTTCTAAAGTTAACTTCGATC
CGATCGACAAGAATCAGATCCAGCTGTTCAATCTGGAATCTTCCAAAAT
CGAAGTTATCCTGAAGAATGCTATCGTATACAACTCTATGTACGAAAACT
TCTCCACCTCCTTCTGGATCCGTATCCCGAAATACTTCAACTCCATCTCTC
TGAACAATGAATACACCATCATCAACTGCATGGAAAACAATTCTGGTTG
GAAAGTATCTCTGAACTACGGTGAAATCATCTGGACTCTGCAGGACACT
CAGGAAATCAAACAGCGTGTTGTATTCAAATACTCTCAGATGATCAACA
TCTCTGACTACATCAATCGCTGGATCTTCGTTACCATCACCAACAATCGT
CTGAATAACTCCAAAATCTACATCAACGGCCGTCTGATCGACCAGAAAC
CGATCTCCAATCTGGGTAACATCCACGCTTCTAATAACATCATGTTCAAA
CTGGACGGTTGTCGTGACACTCACCGCTACATCTGGATCAAATACTTCAA
TCTGTTCGACAAAGAACTGAACGAAAAGAAATCAAAGACCTGTACGAC
AACCAGTCCAATTCTGGTATCCTGAAAGACTTCTGGGGTGACTACCTGCA
GTACGACAAACCGTACTACATGCTGAATCTGTACGATCCGAACAAATAC
GTTGACGTCAACAATGTAGGTATCCGCGGTTACATGTACCTGAAAGGTC
CGCGTGGTTCTGTTATGACTACCAACATCTACCTGAACTCTTCCCTGTAC
CGTGGTACCAAATTCATCATCAAGAAATACGCGTCTGGTAACAAGGACA
ATATCGTTCGCAACAATGATCGTGTATACATCAATGTTGTAGTTAAGAAC
AAAGAATACCGTCTGGCTACCAATGCTTCTCAGGCTGGTGTAGAAAAGA
TCTTGTCTGCTCTGGAAATCCCGGACGTTGGTAATCTGTCTCAGGTAGTT
GTAATGAAATCCAAGAACGACCAGGGTATCACTAACAAATGCAAAATGA
ATCTGCAGGACAACAATGGTAACGATATCGGTTTCATCGGTTTCCACCAG
TTCAACAATATCGCTAAACTGGTTGCTTCCAACTGGTACAATCGTCAGAT
CGAACGTTCCTCTCGCACTCTGGGTTGCTCTTGGGAGTTCATCCCGGTTG
ATGACGGTTGGGGTGAACGTCCGCTGtaaGAATTC

B: BoNTA(H$_c$) encoded protein (Version #3) SEQ ID NO: 6

MASTFTEYIKNIINTSILNLRYESNHLIDLSRYASKINIGSKVNFDPIDKNQIQL
FNLESSKIEVILKNAIVYNSMYENFSTSFWIRIPKYFNSISLNNEYTIINCMENN
SGWKVSLNYGEIIWTLQDTQEIKQRVVFKYSQMINISDYINRWIFVTITNNRL
NNSKIYINGRLIDQKPISNLGNIHASNNIMFKLDGCRDTHRYIWIKYFNLFDK
ELNEKEIKDLYDNQSNSGILKDFWGDYLQYDKPYYMLNLYDPNKYVDVNN
VGIRGYMYLKGPRGSVMTTNIYLNSSLYRGTKFIIKKYASGNKDNIVRNNDR
VYINVVVKNKEYRLATNASQAGVEKILSALEIPDVGNLSQVVVMKSKNDQ
GITNKCKMNLQDNNGNDIGFIGFHQFNNIAKLVASNWYNRQIERSSRTLGCS
WEFIPVDDGWGERPL*

FIGURE 4

A: BoNTB(H$_c$) synthetic gene SEQ ID NO: 7

GAATTCACGatgGCCAACAAATACAATTCCGAAATCCTGAACAATATCAT
CCTGAACCTGCGTTACAAAGACAACAATCTGATCGATCTGTCTGGTTACG
GTGCTAAAGTTGAAGTATACGACGGTGTTGAACTGAATGACAAGAACCA
GTTCAAACTGACCTCTTCCGCTAACTCTAAGATCCGTGTTACTCAGAATC
AGAACATCATCTTCAACTCCGTATTCCTGGACTTCTCTGTTTCCTTCTGGA
TTCGTATCCCGAAATACAAGAACGACGGTATCCAGAATTACATCCACAA
TGAATACACCATCATCAACTGCATGAAGAATAACTCTGGTTGGAAGATC
TCCATCCGCGGTAACCGTATCATCTGGACTCTGATCGATATCAACGGTAA
GACCAAATCTGTATTCTTCGAATACAACATCCGTGAAGACATCTCTGAAT
ACATCAATCGCTGGTTCTTCGTTACCATCACCAATAACCTGAACAATGCT
AAAATCTACATCAACGGTAAACTGGAATCTAATACCGACATCAAAGACA
TCCGTGAAGTTATCGCTAACGGTGAAATCATCTTCAAACTGGACGGTGA
CATCGATCGTACCCAGTTCATCTGGATGAAATACTTCTCCATCTTCAACA
CCGAACTGTCTCAGTCCAATATCGAAGAACGGTACAAGATCCAGTCTTA
CTCCGAATACCTGAAAGACTTCTGGGGTAATCCGCTGATGTACAACAAA
GAATACTATATGTTCAATGCTGGTAACAAGAACTCTTACATCAAACTGA
AGAAAGACTCTCCGGTTGGTGAAATCCTGACTCGTTCCAAATACAACCA
GAACTCTAAATACATCAACTACCGCGACCTGTACATCGGTGAAAAGTTC
ATCATCCGTCGCAAATCTAACTCTCAGTCCATCAATGATGACATCGTACG
TAAAGAAGACTACATCTACCTGGACTTCTTCAACCTGAATCAGGAATGG
CGTGTATACACCTACAAGTACTTCAAGAAAGAAGAAGAAAAGCTTTTCC
TGGCTCCGATCTCTGATTCCGACGAACTCTACAACACCATCCAGATCAAA
GAATACGACGAACAGCCGACCTACTCTTGCCAGCTGCTGTTCAAGAAAG
ATGAAGAATCTACTGACGAAATCGGTCTGATCGGTATCCACCGTTTCTAC
GAATCTGGTATCGTATTCGAAGAATACAAAGACTACTTCTGCATCTCCAA
ATGGTACCTGAAGGAAGTTAAACGCAAACCGTACAACCTGAAACTGGGT
TGCAATTGGCAGTTCATCCCGAAAGACGAAGGTTGGACCGAAtagtaaGAA
TTC

B: BoNTB(H$_c$) encoded protein SEQ ID NO: 8

MANKYNSEILNNIILNLRYKDNNLIDLSGYGAKVEVYDGVELNDKNQFKLT
SSANSKIRVTQNQNIIFNSVFLDFSVSFWIRIPKYKNDGIQNYIHNEYTIINCM
KNNSGWKISIRGNRIIWTLIDINGKTKSVFFEYNIREDISEYINRWFFVTITNNL
NNAKIYINGKLESNTDIKDIREVIANGEIIFKLDGDIDRTQFIWMKYFSIFNTEL
SQSNIEERYKIQSYSEYLKDFWGNPLMYNKEYYMFNAGNKNSYIKLKKDSP
VGEILTRSKYNQNSKYINYRDLYIGEKFIIRRKSNSQSINDDIVRKEDYIYLDF
FNLQEWRVYTYKYFKKEEEKLFLAPISDSDELYNTIQIKEYDEQPTYSCQL
LFKKDEESTDEIGLIGIHRFYESGIVFEEYKDYFCISKWYLKEVKRKPYNLKL
GCNWQFIPKDEGWTE**

FIGURE 5

A: BoNTC$_1$(H$_c$) synthetic gene SEQ ID NO: 9

GAATTCACGatgACCATCCCATTCAACATCTTCTCCTACACCAACAACTCC
CTGTTGAAGGACATCATCAACGAGTACTTCAACAACATCAACGACTCCA
AGATCCTGTCCCTGCAGAACCGTAAGAACACCTTGGTCGACACCTCCGG
TTACAACGCCGAGGTCTCCGAGGAGGGTGACGTCCAGCTGAACCCAATC
TTCCCATTCGACTTCAAGCTGGGTTCCTCCGGTGAGGACAGAGGTAAGGT
CATCGTCACCCAGAACGAGAACATCGTCTACAACTCCATGTACGAGTCC
TTCTCCATCTCCTTCTGGATCAGAATCAACAAGTGGGTCTCCAACTTGCC
AGGTTACACCATCATCGACTCCGTCAAGAACAACTCCGGTTGGTCCATCG
GTATCATCTCCAACTTCCTGGTCTTCACCCTGAAGCAGAACGAGGACTCC
GAGCAGTCCATCAACTTCTCCTACGACATCTCCAACAACGCTCCTGGTTA
CAACAAGTGGTTCTTCGTCACCGTCACCAACAACATGATGGGTAACATG
AAGATCTACATCAACGGTAAGCTGATCGACACCATCAAGGTCAAGGAGT
TGACCGGTATCAACTTCTCCAAGACCATCACCTTCGAGATCAACAAGATC
CCAGACACCGGTCTGATCACCTCCGACTCCGACAACATCAACATGTGGA
TCCGTGACTTCTACATCTTCGCCAAGGAGTTGGACGGTAAGGACATCAA
CATCCTGTTCAACTCCTTGCAGTACACCAACGTCGTCAAGGACTACTGGG
GTAACGACCTGAGATACAACAAGGAGTACTACATGGTCAACATCGACTA
CTTGAACAGATACATGTACGCCAACTCCAGACAGATCGTCTTCAACACC
AGACGTAACAACAACGACTTCAACGAGGGTTACAAGATCATCATCAAGC
GTATCAGAGGTAACACCAACGACACCAGAGTCAGAGGTGGTGACATCCT
GTACTTCGACATGACTATCAACAACAAGGCCTACAACCTGTTCATGAAG
AACGAGACCATGTACGCCGACAACCACTCCACCGAGGACATCTACGCCA
TCGGTCTGCGTGAGCAGACCAAGGACATCAACGACAACATCATCTTCCA
GATCCAGCCAATGAACAACACTTACTACTACGCTTCCCAGATCTTCAAGT
CCAACTTCAACGGTGAGAACATCTCCGGTATCTGTTCCATCGGTACCTAC
AGATTCCGTCTGGGTGGTGACTGGTACAGACACAACTACTTGGTTCCAAC
TGTCAAGCAGGGTAACTACGCCTCCTTGCTGGAGTCCACTTCCACCCACT
GGGGATTCGTCCCAGTCTCCGAGtaatagGAATTC B: BoNTC$_1$(H$_c$) encoded protein SEQ ID NO: 10

MTIPFNIFSYTNNSLLKDIINEYFNNINDSKILSLQNRKNTLVDTSGYNAEVSE
EGDVQLNPIFPFDFKLGSSGEDRGKVIVTQNENIVYNSMYESFSISFWIRINK
WVSNLPGYTIIDSVKNNSGWSIGIISNFLVFTLKQNEDSEQSINFSYDISNNAP
GYNKWFFVTVTNNMMGNMKIYINGKLIDTIKVKELTGINFSKTITFEINKIPD
TGLITSDSDNINMWIRDFYIFAKELDGKDINILFNSLQYTNVVKDYWGNDLR
YNKEYYMVNIDYLNRYMYANSRQIVFNTRRNNNDFNEGYKIIIKRIRGNTN
DTRVRGGDILYFDMTINNKAYNLFMKNETMYADNHSTEDIYAIGLREQTKD
INDNIIFQIQPMNNTYYYASQIFKSNFNGENISGICSIGTYRFRLGGDWYRHN
YLVPTVKQGNYASLLESTSTHWGFVPVSE**

FIGURE 6

A: BoNTD(H$_c$) synthetic gene SEQ ID NO: 11

GAATTCACGatgCGTTTGAAGGCTAAGGTCAACGAGTCCTTCGAGAACAC
CATGCCATTCAACATCTTCTCCTACACCAACAACTCCTTGTTGAAGGACA
TCATCAACGAGTACTTCAACTCCATCAACGACTCCAAGATCTTGTCCTTG
CAGAACAAGAAGAACGCCTTGGTCGACACCTCCGGTTACAACGCCGAGG
TCAGAGTCGGTGACAACGTCCAGTTGAACACCATCTACACCAACGACTT
CAAGTTGTCCTCTTCCGGTGACAAGATCATCGTCAACTTGAACAACAACA
TCTTGTACTCCGCCATCTACGAGAACTCCTCTGTCTCCTTCTGGATCAAG
ATCTCCAAGGACTTGACCAACTCCCACAACGAGTACACCATCATCAACT
CCATCGAGCAGAACTCCGGTTGGAAGTTGTGTATCCGTAACGGTAACAT
CGAGTGGATCTTGCAGGACGTCAACCGTAAGTACAAGTCCTTGATCTTCG
ACTACTCCGAGTCCTTGTCCCACACCGGTTACACCAACAAGTGGTTCTTC
GTCACCATCACCAACAACATCATGGGTTACATGAAGTTGTACATCAACG
GTGAGTTGAAGCAGTCCCAGAAGATCGAGGACCTGGACGAGGTCAAGCT
GGACAAGACCATCGTCTTCGGTATCGACGAGAACATCGACGAGAACCAG
ATGTTGTGGATCCGTGACTTCAACATCTTCTCCAAGGAGCTGTCCAACGA
GGACATCAACATCGTCTACGAGGGTCAGATCCTGAGGAACGTCATCAAG
GACTACTGGGGTAACCCACTGAAGTTCGACACCGAGTACTACATCATCA
ACGACAACTACATCGACCGTTACATCGCCCCAGAGTCCAACGTCCTGGT
CCTGGTCCAGTACCCTGACCGTTCCAAGCTGTACACCGGTAACCCTATCA
CCATCAAGTCCGTCTCCGACAAGAACCCTTACTCCCGTATCCTGAACGGT
GACAACATCATCCTGCACATGCTGTACAACTCCCGTAAGTACATGATCAT
CCGTGACACCGACACCATCTACGCCACCCAGGGTGGTGACTGTTCCCAG
AACTGTGTCTACGCCCTGAAGCTGCAGTCCAACCTGGGTAACTACGGTAT
CGGTATCTTCTCCATCAAGAACATCGTCTCCAAGAACAAGTACTGCTCCC
AGATCTTCTCCTCCTTCCGTGAGAACACCATGCTGCTGGCCGACATCTAC
AAGCCTTGGCGTTTCTCCTTCAAGAACGCCTACACTCCTGTCGCCGTCAC
CAACTACGAGACCAAGCTGCTGTCCACCTCCTCCTTCTGGAAGTTCATCT
CCCGTGACCCAGGTTGGGTCGAGtaatagGAATTC

B: BoNTD(H$_c$) encoded protein SEQ ID NO: 12

MRLKAKVNESFENTMPFNIFSYTNNSLLKDIINEYFNSINDSKILSLQNKKNA
LVDTSGYNAEVRVGDNVQLNTIYTNDFKLSSSGDKIIVNLNNNILYSAIYENS
SVSFWIKISKDLTNSHNEYTIINSIEQNSGWKLCIRNGNIEWILQDVNRKYKS
LIFDYSESLSHTGYTNKWFFVTITNNIMGYMKLYINGELKQSQKIEDLDEVK
LDKTIVFGIDENIDENQMLWIRDFNIFSKELSNEDINIVYEGQILRNVIKDYW
GNPLKFDTEYYIINDNYIDRYIAPESNVLVLVQYPDRSKLYTGNPITIKSVSD
KNPYSRILNGDNIILHMLYNSRKYMIIRDTDTIYATQGGDCSQNCVYALKLQ
SNLGNYGIGIFSIKNIVSKNKYCSQIFSSFRENTMLLADIYKPWRFSFKNAYTP
VAVTNYETKLLSTSSFWKFISRDPGWVE**

FIGURE 7

A: BoNTE(H$_c$) synthetic gene SEQ ID NO: 13

GAATTCACCatgGGAGAGAGTCAGCAAGAACTAAATTCTATGGTAACTGA
TACCCTAAATAATAGTATTCCTTTTAAGCTTTCTTCTTATACAGATGATAA
AATTTTAATTTCCTACTTCAACAAGTTCTTCAAGAGAATTAAGTCTTCTTC
CGTTTTAAACATGAGATACAAGAATGATAAATACGTCGACACTTCCGGT
TACGACTCCAATATCAACATTAACGGTGACGTGTACAAGTACCCAACTA
ACAAAAACCAATTCGGTATCTACAACGACAAGCTTACTGAGCTGAACAT
CTCTCAAAACGACTACATTATCTACGACAACAAGTACAAGAACTTCTCTA
TTTCTTTCTGGGTCAGGATTCCTAACTACGACAACAAGATCGTCAACGTT
AACAACGAGTACACTATCATCAACTGTATGAGAGACAACAACTCCGGTT
GGAAGGTCTCTCTTAACCACAACGAGATCATTTGGACCTTGCAAGACAA
CGCAGGTATTAACCAAAAGTTAGCATTCAACTACGGTAACGCAAACGGT
ATTTCTGACTACATCAACAAGTGGATTTTCGTCACTATCACTAACGACAG
ATTAGGTGACTCTAAGCTTTACATTAACGGTAACTTAATCGACCAAAAGT
CCATTTTAAACTTAGGTAACATTCACGTTTCTGACAACATCTTATTCAAG
ATCGTTAACTGCAGTTACACCAGATACATTGGCATTAGATACTTCAACAT
TTTCGACAAGGAGTTAGACGAGACCGAGATTCAAACTTTATACAGCAAC
GAACCTAACACCAATATTTTGAAGGACTTCTGGGGTAACTACTTGCTTTA
CGACAAGGAATACTACTTATTAAACGTGTTAAAGCCAAACAACTTCATT
GATAGGAGAAAGGATTCTACTTTAAGCATTAACAACATCAGAAGCACTA
TTCTTTTAGCTAACAGATTATACTCTGGTATCAAGGTTAAGATCCAAAGA
GTTAACAACTCTTCTACTAACGATAACCTTGTTAGAAAGAACGATCAGGT
CTATATTAACTTCGTCGCTAGCAAGACTCACTTATTCCCATTATATGCTG
ATACCGCTACCACCAACAAGGAGAAGACCATCAAGATCTCCTCCTCTGG
CAACAGATTTAACCAAGTCGTCGTTATGAACTCCGTCGGTAACAACTGTA
CCATGAACTTTAAAAATAATAATGGAAATAATATTGGGTTGTTAGGTTTC
AAGGCAGATACTGTAGTTGCTAGTACTTGGTATTATACCCACATGAGAG
ATCACACCAACAGCAATGGATGTTTTGGAACTTTATTTCTGAAGAACAT
GGATGGCAAGAAAAAtaa
TagGGATCC GCGGCCGC ACGCGT CCCGGG ACTAGT GAATTC

B: BoNTE(H$_c$) encoded protein SEQ ID NO: 14

MGESQQELNSMVTDTLNNSIPFKLSSYTDDKILISYFNKFFKRIKSSSVLNMR
YKNDKYVDTSGYDSNININGDVYKYPTNKNQFGIYNDKLTELNISQNDYIIY
DNKYKNFSISFWVRIPNYDNKIVNVNNEYTIINCMRDNNSGWKVSLNHNEII
WTLQDNAGINQKLAFNYGNANGISDYINKWIFVTITNDRLGDSKLYINGNLI
DQKSILNLGNIHVSDNILFKIVNCSYTRYIGIRYFNIFDKELDETEIQTLYSNEP
NTNILKDFWGNYLLYDKEYYLLNVLKPNNFIDRRKDSTLSINNIRSTILLANR
LYSGIKVKIQRVNNSSTNDNLVRKNDQVYINFVASKTHLFPLYADTATTNKE
KTIKISSSGNRFNQVVVMNSVGNNCTMNFKNNNGNNIGLLGFKADTVVAST
WYYTHMRDHTNSNGCFWNFISEEHGWQEK**

Fig. 8

AMINO ACID AND DESIGNED NUCLEOTIDE SEQUENCE OF BONTE(Hc)

FIGURE 9

A: BoNTF(H$_c$) synthetic gene SEQ ID NO: 15

GAATTCACGatgTCCTACACCAACGACAAGATCCTGATCTTGTACTTCAAC
AAGCTGTACAAGAAGATCAAGGACAACTCCATCTTGGACATGAGATACG
AAAACAATAAGTTCATCGACATCTCCGGTTACGGTTCCAACATCTCCATC
AACGGTGACGTCTACATCTACTCCACCAATAGAAACCAGTTCGGAATCT
ACTCCTCCAAGCCTTCCGAGGTCAACATCGCTCAGAACAACGACATCAT
CTACAACGGAAGATACCAGAACTTCTCCATCTCCTTCTGGGTCCGTATCC
CAAAGTACTTCAACAAGGTCAACCTGAATAACGAGTACACCATCATCGA
CTGCATCCGTAACAATAACTCCGGATGGAAGATCTCCCTGAACTACAAC
AAGATCATCTGGACCCTGCAGGACACCGCCGGTAACAATCAGAAGTTGG
TCTTCAACTACACCCAGATGATCTCCATCTCCGACTACATCAACAAGTGG
ATCTTCGTCACCATCACCAATAACCGTTTGGGAAACTCCAGAATCTACAT
CAACGGTAACTTGATCGACGAGAAGTCCATCTCCAACTTGGGTGACATC
CACGTCTCCGACAACATTTTGTTCAAGATCGTCGGTTGTAACGACACCCG
TTACGTCGGGATCCGTTACTTCAAAGTCTTCGACACTGAGTTGGGTAAGA
CCGAGATCGAGACCTTGTACTCCGACGAGCCTGACCCATCCATCCTGAA
GGACTTCTGGGGTAACTACCTGCTGTACAACAAACGTTACTACTTGCTGA
ACTTGTTGCGTACCGACAAGTCCATCACCCAGAACTCCAACTTCTTGAAC
ATCAACCAGCAGAGAGGTGTCTACCAGAAGCCAAACATCTTCTCCAACA
CCAGATTGTACACCGGAGTCGAGGTCATTATCAGAAAGAACGGATCTAC
TGATATTTCCAACACCGATAACTTCGTCAGAAAGAACGATCTGGCTTACA
TCAACGTTGTCGACAGAGATGTCGAATACCGTCTGTACGCCGATATCTCT
ATCGCCAAACCTGAAAAGATCATCAAGCTGATCCGTACCTCTAACTCTA
ACAACTCTCTGGGACAAATCATCGTCATGGACTCCATCGGTAATAACTGT
ACCATGAACTTCCAGAACAACAACGGTGGAAACATCGGTTTGTTGGGTT
CCACTCCAACAACTTGGTCGCTTCCTCCTGGTACTACAACAACATCCGT
AAGAACACCTCCTCCAACGGTTGCTTCTGGTCCTTCATCTCCAAGGAGCA
CGGTTGGCAGGAGAACtaatagGAATTC

B: BoNTF(H$_c$) encoded protein SEQ ID NO: 16

MSYTNDKILILYFNKLYKKIKDNSILDMRYENNKFIDISGYGSNISINGDVYIY
STNRNQFGIYSSKPSEVNIAQNNDIIYNGRYQNFSISFWVRIPKYFNKVNLNN
EYTIIDCIRNNNSGWKISLNYNKIIWTLQDTAGNNQKLVFNYTQMISISDYIN
KWIFVTITNNRLGNSRIYINGNLIDEKSISNLGDIHVSDNILFKIVGCNDTRYV
GIRYFKVFDTELGKTEIETLYSDEPDPSILKDFWGNYLLYNKRYYLLNLLRT
DKSITQNSNFLNINQQRGVYQKPNIFSNTRLYTGVEVIIRKNGSTDISNTDNF
VRKNDLAYINVVDRDVEYRLYADISIAKPEKIIKLIRTSNSNNSLGQIIVMDSI
GNNCTMNFQNNNGGNIGLLGFHSNNLVASSWYYNNIRKNTSSNGCFWSFIS
KEHGWQEN**

FIGURE 10

A: BoNTG(H$_C$) synthetic gene SEQ ID NO: 17

GAATTCACGatgAAGGACACCATCCTGATCCAGGTCTTCAACAACTACATC
TCCAACATCTCCTCCAACGCCATCCTGTCCCTGTCCTACCGTGGTGGTCG
TCTGATCGACTCCTCCGGTTACGGAGCCACCATGAACGTCGGTTCCGACG
TCATCTTCAACGACATCGGTAACGGTCAGTTCAAGCTGAACAACTCCGA
GAACTCCAACATCACCGCCCACCAGTCCAAGTTCGTCGTCTACGACTCCA
TGTTCGACAACTTCTCCATCAACTTCTGGGTCCGTACCCCAAAGTACAAC
AACAACGACATCCAGACCTACCTGCAGAACGAGTACACCATCATCTCCT
GTATCAAGAACGACTCCGGTTGGAAGGTCTCCATCAAGGGAAACCGTAT
CATCTGGACCCTGATCGACGTCAACGCCAAGTCCAAGTCCATCTTCTTCG
AGTACTCCATCAAGGACAACATCTCCGACTACATCAACAAGTGGTTCTCC
ATCACCATCACCAACGACCGTCTGGGTAACGCCAACATCTACATCAACG
GTTCCCTGAAGAAGTCCGAGAAGATCCTGAACCTGGACCGTATCAACTC
CTCCAACGACATCGACTTCAAGCTGATCAACTGTACCGACACCACCAAG
TTCGTCTGGATCAAGGACTTCAACATCTTCGGTCGTGAGCTGAACGCCAC
CGAGGTCTCCTCCCTGTACTGGATCCAGTCCTCCACCAACACCCTGAAGG
ACTTCTGGGGAAACCCACTGCGTTACGACACCCAGTACTACCTGTTCAAC
CAGGGTATGCAGAACATCTACATCAAGTACTTCTCCAAGGCCTCCATGG
GTGAGACCGCCCCTCGTACCAACTTCAACAACGCCGCCATCAACTACCA
GAACCTGTACCTGGGTCTGCGTTTCATCATCAAGAAGGCCTCCAACTCCC
GTAACATCAACAACGACAACATCGTCCGTGAGGGTGACTACATCTACCT
GAACATCGACAACATCTCCGACGAGTCCTACCGTGTCTACGTCCTGGTCA
ACTCCAAGGAGATCCAGACCCAGCTGTTCCTGGCCCCAATCAACGACGA
CCCTACCTTCTACGACGTCCTGCAGATCAAGAAGTACTACGAGAAGACC
ACCTACAACTGTCAGATCCTGTGCGAGAAGGACACCAAGACCTTCGGAC
TGTTCGGTATCGGTAAGTTCGTCAAGGACTACGGTTACGTCTGGGACACC
TACGACAACTACTTCTGTATCTCCCAGTGGTACCTGCGTCGTATCTCCGA
GAACATCAACAAGCTGCGTCTGGGATGTAACTGGCAGTTCATCCCAGTC
GACGAGGGTTGGACCGAGtaatagGAATTC B: BoNTG(H$_C$) encoded protein SEQ ID NO: 18

MKDTILIQVFNNYISNISSNAILSLSYRGGRLIDSSGYGATMNVGSDVIFNDIG
NGQFKLNNSENSNITAHQSKFVVYDSMFDNFSINFWVRTPKYNNNDIQTYL
QNEYTIISCIKNDSGWKVSIKGNRIIWTLIDVNAKSKSIFFEYSIKDNISDYINK
WFSITITNDRLGNANIYINGSLKKSEKILNLDRINSSNDIDFKLINCTDTTKFV
WIKDFNIFGRELNATEVSSLYWIQSSTNTLKDFWGNPLRYDTQYYLFNQGM
QNIYIKYFSKASMGETAPRTNFNNAAINYQNLYLGLRFIIKKASNSRNINNDN
IVREGDYIYLNIDNISDESYRVYVLVNSKEIQTQLFLAPINDDPTFYDVLQIKK
YYEKTTYNCQILCEKDTKTFGLFGIGKFVKDYGYVWDTYDNYFCISQWYLR
RISENINKLRLGCNWQFIPVDEGWTE**

FIGURE 11

A: BoNTA(H$_N$) synthetic gene SEQ ID NO: 19 atgGCTCTGAACGACCTGTGCATCAAAGTTAACAACTGGGACCTGTTCTTC
TCCCCGTCTGAAGACAACTTCACTAACGACCTGAACAAAGGCGAAGAAA
TCACCTCCGACACTAACATCGAAGCTGCTGAAGAAAACATCTCTCTGGA
CCTGATCCAGCAGTACTACCTGACTTTCAACTTCGACAACGAACCGGAA
AACATCTCCATCGAAAACCTGTCTTCCGACATCATCGGTCAGCTGGAACT
GATGCCGAACATCGAACGCTTCCCGAACGGCAAGAAATACGAACTGGAC
AAATACACCATGTTCCACTACCTGCGTGCTCAGGAATTCGAACACGGTA
AATCTCGTATCGCTCTGACTAACTCCGTTAACGAAGCTCTGCTGAACCCG
TCTCGCGTTTACACCTTCTTCTCTTCCGACTACGTTAAGAAAGTTAACAA
AGCTACTGAAGCTGCTATGTTCCTGGGTTGGGTTGAACAGCTGGTTTACG
ACTTCACCGACGAAACTTCTGAAGTTTCCACCACTGACAAAATCGCTGAC
ATCACTATCATCATCCCGTACATCGGCCCGGCTCTGAACATCGGTAACAT
GCTGTACAAAGACGACTTCGTTGGTGCTCTGATCTTCTCTGGCGCTGTTA
TCCTGCTGGAATTCATCCCGGAAATCGCTATCCCGGTTCTGGGTACCTTC
GCTCTGGTTTCCTACATCGCTAACAAAGTTCTGACTGTTCAGACCATCGA
CAACGCTCTGTCTAAACGTAACGAAAAATGGGACGAAGTTTACAAATAC
ATCGTTACTAACTGGCTGGCTAAAGTTAACACTCAGATCGACCTGATCCG
TAAGAAGATGAAAGAAGCTCTGGAAAACCAGGCTGAAGCTACTAAAGC
TATCATCAACTACCAGTACAACCAGTACACCGAAGAAGAAAAGAACAAC
ATCAACTTCAACATCGATGACCTGTCCTCTAAACTGAACGAATCCATCAA
CAAAGCTATGATCAACATCAACAAATTCCTGAACCAGTGCTCTGTTTCCT
ACCTGATGAACTCTATGATCCCGTACGGCGTTAAACGCCTGGAAGACTTC
GACGCTTCCCTGAAAGACGCTCTGCTGAAATACATCCGTGACAACTACG
GTACTCTGATCGGCCAGGTTGACCGTCTGAAAGACAAGGTTAACAACAC
CCTGTCTACTGACATCCCGTTCCAGCTGTCCAAATACGTTGACAACCAGta
a B: BoNTA(H$_N$) encoded protein SEQ ID NO: 20

MALNDLCIKVNNWDLFFSPSEDNFTNDLNKGEEITSDTNIEAAEENISLDLIQ
QYYLTFNFDNEPENISIENLSSDIIGQLELMPNIERFPNGKKYELDKYTMFHY
LRAQEFEHGKSRIALTNSVNEALLNPSRVYTFFSSDYVKKVNKATEAAMFL
GWVEQLVYDFTDETSEVSTTDKIADITIIIPYIGPALNIGNMLYKDDFVGALIF
SGAVILLEFIPEIAIPVLGTFALVSYIANKVLTVQTIDNALSKRNEKWDEVYK
YIVTNWLAKVNTQIDLIRKKMKEALENQAEATKAIINYQYNQYTEEEKNNI
NFNIDDLSSKLNESINKAMININKFLNQCSVSYLMNSMIPYGVKRLEDFDASL
KDALLKYIRDNYGTLIGQVDRLKDKVNNTLSTDIPFQLSKYVDNQ*

FIGURE 12

A: BoNTB(H$_N$) synthetic gene SEQ ID NO: 21 atgGCTCCAGGAATCTGTATCGACGTCGACAACGAGGACTTGTTCTTCATC
GCTGACAAGAACTCCTTCTCCGACGACTTGTCCAAGAACGAGAGAATCG
AGTACAACACCCAGTCCAACTACATCGAGAACGACTTCCCAATCAACGA
GTTGATCTTGGACACCGACTTGATCTCCAAGATCGAGTTGCCATCCGAGA
ACACCGAGTCCTTGACTGACTTCAACGTCGACGTCCCAGTCTACGAGAA
GCAACCAGCTATCAAGAAGATTTTCACCGACGAGAACACCATCTTCCAA
TACCTGTACTCTCAGACCTTCCCTTTGGACATCAGAGACATCTCCTTGAC
CTCTTCCTTCGACGACGCCCTGCTGTTCTCCAACAAGGTCTACTCCTTCTT
CTCCATGGACTACATCAAGACTGCTAACAAGGTCGTCGAGGCCGGTTTG
TTCGCTGGTTGGGTCAAGCAGATCGTCAACGATTTCGTCATCGAGGCTAA
CAAGTCCAACACCATGGACAAGATTGCCGACATCTCCTTGATTGTCCCAT
ACATCGGTTTGGCCTTGAACGTCGGTAACGAGACCGCCAAGGGTAACTT
CGAGAACGCTTTCGAGATCGCTGGTGCCTCCATCTTGTTGGAGTTCATCC
CAGAGTTGTTGATCCCAGTCGTCGGTGCCTTCTTGTTGGAGTCCTACATC
GACAACAAGAACAAGATCATCAAGACCATCGACAACGCTTTGACCAAGA
GAAACGAGAAGTGGTCCGACATGTACGGTTTGATCGTCGCCCAATGGTT
GTCCACCGTCAACACCCAATTCTACACCATCAAGGAGGGTATGTACAAG
GCCTTGAACTACCAGGCCCAAGCTTTGGAGGAGATCATCAAGTACAGAT
ACAACATCTACTCCGAGAAGGAGAAGTCCAACATTAACATCGACTTCAA
CGACATCAACTCCAAGCTGAACGAGGGTATTAACCAGGCCATCGACAAC
ATCAACAACTTCATCAACGGTTGTTCCGTCTCCTACTTGATGAAGAAGAT
GATTCCATTGGCCGTCGAGAAGTTGTTGGACTTCGACAACACCCTGAAG
AAGAACTTGTTGAACTACATCGACGAGAACAAGTTGTACTTGATCGGTT
CCGCTGAGTACGAGAAGTCCAAGGTCAACAAGTACTTGAAGACCATCAT
GCCATTCGACTTGTCCATCTACACCAACGACACCATCTTGATCGAGATGT
TCtaa

B: BoNTB(H$_N$) encoded protein SEQ ID NO: 22

MAPGICIDVDNEDLFFIADKNSFSDDLSKNERIEYNTQSNYIENDFPINELILD
TDLISKIELPSENTESLTDFNVDVPVYEKQPAIKKIFTDENTIFQYLYSQTFPLD
IRDISLTSSFDDALLFSNKVYSFFSMDYIKTANKVVEAGLFAGWVKQIVNDF
VIEANKSNTMDKIADISLIVPYIGLALNVGNETAKGNFENAFEIAGASILLEFI
PELLIPVVGAFLLESYIDNKNKIIKTIDNALTKRNEKWSDMYGLIVAQWLST
VNTQFYTIKEGMYKALNYQAQALEEIIKYRYNIYSEKEKSNINIDFNDINSKL
NEGINQAIDNINNFINGCSVSYLMKKMIPLAVEKLLDFDNTLKKNLLNYIDE
NKLYLIGSAEYEKSKVNKYLKTIMPFDLSIYTNDTILIEMF*

FIGURE 13

A: BoNTC$_1$(H$_N$) synthetic gene SEQ ID NO: 23 atgTCCCTGTACAACAAGACCCTTGACTGTAGAGAGCTGCTGGTGAAGAA
CACTGACCTGCCATTCATCGGTGACATCAGTGACGTGAAGACTGACATCT
TCCTGCGTAAGGACATCAACGAGGAGACTGAGGTGATCTACTACCCAGA
CAACGTGTCAGTAGACCAAGTGATCCTCAGTAAGAACACCTCCGAGCAT
GGACAACTAGACCTGCTCTACCCTAGTATCGACAGTGAGAGTGAGATCC
TGCCAGGGGAGAATCAAGTCTTCTACGACAACCGTACCCAGAACGTGGA
CTACCTGAACTCCTACTACTACCTAGAGTCTCAGAAGCTGAGTGACAAC
GTGGAGGACTTCACTTTCACGCGTTCAATCGAGGAGGCTCTGGACAACA
GTGCAAAGGTGTACACTTACTTCCCTACCCTGGCTAACAAGGTGAATGCC
GGTGTGCAAGGTGGTCTGTTCCTGATGTGGGCAAACGACGTGGTTGAGG
ACTTCACTACCAACATCCTGCGTAAGGACACACTGGACAAGATCTCAGA
TGTGTCAGCTATCATCCCCTACATCGGACCCGCACTGAACATCTCCAACT
CTGTGCGTCGTGGAAACTTCACTGAGGCATTCGCAGTCACTGGTGTCACC
ATCCTGCTGGAGGCATTCCCTGAGTTCACAATCCCTGCTCTGGGTGCATT
CGTGATCTACAGTAAGGTCCAGGAGCGAAACGAGATCATCAAGACCATC
GACAACTGTCTGGAGCAGAGGATCAAGAGATGGAAGGACTCCTACGAGT
GGATGATGGGAACGTGGTTGTCCAGGATCATCACCCAGTTCAACAACAT
CTCCTACCAGATGTACGACTCCCTGAACTACCAGGCAGGTGCAATCAAG
GCTAAGATCGACCTGGAGTACAAGAAGTACTCCGGAAGCGACAAGGAG
AACATCAAGAGCCAGGTTGAGAACCTGAAGAACAGTCTGGACGTCAAG
ATCTCGGAGGCAATGAACAACATCAACAAGTTCATCCGAGAGTGCTCCG
TCACCTACCTGTTCAAGAACATGCTGCCTAAGGTCATCGACGAGCTGAA
CGAGTTCGACCGAAACACCAAGGCAAAGCTGATCAACCTGATCGACTCC
CATAACATCATCCTGGTCGGTGAGGTCGACAAGCTGAAGGCAAAGGTAA
ACAACAGCTTCCAGAACtaa B: BoNTC$_1$(H$_N$) encoded protein SEQ ID NO: 24

MSLYNKTLDCRELLVKNTDLPFIGDISDVKTDIFLRKDINEETEVIYYPDNVS
VDQVILSKNTSEHGQLDLLYPSIDSESEILPGENQVFYDNRTQNVDYLNSYY
YLESQKLSDNVEDFTFTRSIEEALDNSAKVYTYFPTLANKVNAGVQGGLFL
MWANDVVEDFTTNILRKDTLDKISDVSAIIPYIGPALNISNSVRRGNFTEAFA
VTGVTILLEAFPEFTIPALGAFVIYSKVQERNEIIKTIDNCLEQRIKRWKDSYE
WMMGTWLSRIITQFNNISYQMYDSLNYQAGAIKAKIDLEYKKYSGSDKENI
KSQVENLKNSLDVKISEAMNNINKFIRECSVTYLFKNMLPKVIDELNEFDRN
TKAKLINLIDSHNIILVGEVDKLKAKVNNSFQN*

FIGURE 14

A: BoNTD(H$_N$) synthetic gene SEQ ID NO: 25 atggccAACTCCCGTGACGACTCCACCTGCATCAAGGTCAAGAACAACAGA
CTGCCATACGTTGCCGACAAGGACTCCATCTCCCAGGAGATCTTCGAGA
ACAAGATCATCACCGACGAGACCAACGTTCAAAACTACTCCGACAAGTT
CTCTTTGGACGAGTCCATCCTGGACGGTCAGGTCCCAATCAACCCAGAG
ATCGTCGACCCACTGTTGCCAAACGTCAACATGGAGCCATTGAACTTGCC
AGGTGAGGAGATCGTCTTCTACGACGACATCACCAAGTACGTCGACTAC
TTGAACTCCTACTACTACTTGGAGTCTCAAAAGTTGTCTAACAACGTCGA
GAACATCACCTTGACCACCTCCGTCGAGGAGGCCTTGGGTTACTCTAACA
AGATCTACACCTTCCTGCCATCCTTGGCTGAGAAGGTTAACAAGGGTGTT
CAAGCTGGTTTGTTCCTGAACTGGGCCAACGAGGTCGTCGAGGACTTCA
CCACCAACATCATGAAGAAGGACACCCTGGACAAGATCTCCGACGTCTC
CGTCATCATCCCATACATCGGTCCAGCCTTGAACATCGGTAACTCCGCCC
TGAGAGGTAACTTCAACCAGGCCTTCGCCACCGCCGGTGTCGCCTTCCTG
CTGGAGGGTTTCCCAGAGTTCACCATCCCAGCCCTGGGTGTCTTCACCTT
CTACTCCTCCATCCAGGAGAGAGAGAAGATCATCAAGACCATCGAGAAC
TGCTTGGAGCAGAGAGTCAAGAGATGGAAGGACTCCTACCAGTGGATGG
TTTCCAACTGGCTGTCCAGAATCACCACCCAATTCAACCACATCAACTAC
CAGATGTACGACTCCCTGTCCTACCAGGCCGACGCCATCAAGGCCAAGA
TCGACCTGGAGTACAAGAAGTACTCCGGTTCCGACAAGGAGAACATCAA
GTCCCAGGTCGAGAACCTGAAGAACTCCTTGGACGTCAAGATCTCCGAG
GCCATGAACAACATCAACAAGTTCATCCGTGAGTGTTCCGTCACCTACCT
GTTCAAGAACATGCTGCCAAAGGTCATCGACGAGCTGAACAAGTTCGAC
CTGAGAACCAAGACCGAGCTGATCAACCTGATCGACTCCCACAACATCA
TCCTGGTTGGTGAGGTTGACtaa B: BoNTD(H$_N$) encoded protein SEQ ID NO: 26

MANSRDDSTCIKVKNNRLPYVADKDSISQEIFENKIITDETNVQNYSDKFSLD
ESILDGQVPINPEIVDPLLPNVNMEPLNLPGEEIVFYDDITKYVDYLNSYYYL
ESQKLSNNVENITLTTSVEEALGYSNKIYTFLPSLAEKVNKGVQAGLFLNWA
NEVVEDFTTNIMKKDTLDKISDVSVIIPYIGPALNIGNSALRGNFNQAFATAG
VAFLLEGFPEFTIPALGVFTFYSSIQEREKIIKTIENCLEQRVKRWKDSYQWM
VSNWLSRITTQFNHINYQMYDSLSYQADAIKAKIDLEYKKYSGSDKENIKSQ
VENLKNSLDVKISEAMNNINKFIRECSVTYLFKNMLPKVIDELNKFDLRTKT
ELINLIDSHNIILVGEVD*

FIGURE 15

A: BoNTE(H$_N$) synthetic gene SEQ ID NO: 27 atgTCCATCTGCATCGAGATCAACAACGGTGAGCTGTTCTTCGTGGCTTCC
GAGAACAGTTACAACGATGACAACATCAACACTCCTAAGGAGATTGACG
ACACCGTCACTTCTAACAACAACTACGAAAACGACCTGGACCAGGTCAT
CCTAAACTTCAACTCCGAGTCCGCCCCTGGTCTGTCCGACGAGAAGCTGA
ACCTGACCATCCAGAACGACGCTTACATCCCAAAGTACGACTCCAACGG
TACATCCGATATCGAGCAGCATGACGTTAACGAGCTTAACGTCTTCTTCT
ACTTAGACGCTCAGAAGGTGCCCGAGGGTGAGAACAACGTCAATCTCAC
CTCTTCAATTGACACAGCCTTGTTGGAGCAGCCTAAGATCTACACCTTCT
TCTCCTCCGAGTTCATCAACAACGTCAACAAGCCTGTGCAGGCCGCATTG
TTCGTAAGCTGGATTCAGCAGGTGTTAGTAGACTTCACTACTGAGGCTAA
CCAGAAGTCCACTGTTGACAAGATCGCTGACATCTCCATCGTCGTCCCAT
ACATCGGTCTGGCTCTGAACATCGGCAACGAGGCACAGAAGGGCAACTT
CAAGGATGCCCTTGAGTTGTTGGGTGCCGGTATTTGTTGGAGTTCGAAC
CCGAGCTGCTGATCCCTACCATCCTGGTCTTCACGATCAAGTCCTTCCTG
GGTTCCTCCGACAACAAGAACAAGGTCATTAAGGCCATCAACAACGCCC
TGAAGGAGCGTGACGAGAAGTGGAAGGAAGTCTATTCCTTCATCGTCTC
GAACTGGATGACCAAGATCAACACCCAGTTCAACAAGCGAAAGGAGCA
GATGTACCAGGCTCTGCAGAACCAGGTCAACGCCATCAAGACCATCATC
GAGTCCAAGTACAACTCCTACACCCTGGAGGAGAAGAACGAGCTTACCA
ACAAGTACGATATCAAGCAGATCGAGAACGAGCTGAACCAGAAGGTCTC
CATCGCCATGAACAACATCGACAGGTTCCTGACCGAGTCCTCCATCTCCT
ACCTGATGAAGCTCATCAACGAGGTCAAGATCAACAAGCTGCGAGAGTA
CGACGAGAATGTCAAGACGTACCTGCTGAACTACATCATCCAGCACGGA
TCCATCCTGtaa B: BoNTE(H$_N$) encoded protein SEQ ID NO: 28

MSICIEINNGELFFVASENSYNDDNINTPKEIDDTVTSNNNYENDLDQVILNF
NSESAPGLSDEKLNLTIQNDAYIPKYDSNGTSDIEQHDVNELNVFFYLDAQK
VPEGENNVNLTSSIDTALLEQPKIYTFFSSEFINNVNKPVQAALFVSWIQQVL
VDFTTEANQKSTVDKIADISIVVPYIGLALNIGNEAQKGNFKDALELLGAGIL
LEFEPELLIPTILVFTIKSFLGSSDNKNKVIKAINNALKERDEKWKEVYSFIVS
NWMTKINTQFNKRKEQMYQALQNQVNAIKTIIESKYNSYTLEEKNELTNKY
DIKQIENELNQKVSIAMNNIDRFLTESSISYLMKLINEVKINKLREYDENVKT
YLLNYIIQHGSIL*

FIGURE 16

A: BoNTF(H_N) synthetic gene SEQ ID NO: 29 atgGCCCCACCACGTCTGTGTATTAGAGTCAACAACTCAGAATTATTCTTT
GTCGCTTCCGAGTCAAGCTACAACGAGAACGATATTAACACACCTAAAG
AGATTGACGATACTACCAACCTAAACAACAACTACCGGAACAACTTGGA
TGAGGTTATTTTGGATTACAACTCACAGACCATCCCTCAAATTTCCAACC
GTACCTTAAACACTCTTGTCCAAGACAACTCCTACGTTCCAAGATACGAT
TCTAACGGTACCTCAGAGATCGAGGAGTATGATGTTGTTGACTTTAACGT
CTTTTTCTATTTGCATGCCCAGAAGGTGCCAGAAGGTGAAACCAACATCT
CATTGACTTCTTCCATTGATACCGCCTTGTTGGAAGAGTCCAAGGATATC
TTCTTTTCTTCGGAGTTTATCGATACTATCAACAAGCCTGTCAACGCCGC
TCTGTTCATTGATTGGATTAGCAAGGTCATCAGAGATTTTACCACTGAAG
CTACTCAAAAGTCCACTGTTGATAAGATTGCTGACATCTCTTTGATTGTC
CCCTATGTCGGTCTTGCTTTGAACATCATTATTGAGGCAGAAAAGGGTAA
CTTTGAGGAGGCTTTTGAATTGTTGGGAGTTGGTATTTTGTTGGAGTTTG
TTCCAGAACTTACCATTCCTGTCATTTTAGTTTTTACGATCAAGTCCTACA
TCGATTCATACGAGAACAAGAATAAAGCAATTAAAGCTATTAACAACTC
CTTGATCGAAAGAGAGGCTAAGTGGAAGGAAATCTACTCATGGATTGTA
TCAAACTGGCTTACTAGAATTAACACTCAATTTAACAAGAGAAAGGAGC
AAATGTACCAGGCTCTGCAAAACCAAGTCGATGCTATCAAGACTGCAAT
TGAATACAAGTACAACAACTATACTTCCGATGAGAAGAACAGACTTGAA
TCTGAATACAATATCAACAACATTGAAGAAGAGTTGAACAAGAAAGTTT
CTTTGGCTATGAAGAATATCGAAAGATTTATGACCGAATCCTCTATCTCT
TACTTGATGAAGTTGATCAATGAGGCCAAGGTTGGTAAGTTGAAGAAGT
ACGATAACCACGTTAAGAGCGATCTGCTGAACTACATTCTCGACCACAG
ATCAATCCTGGGAGAGCAGACAAACGAGCTGAGTGATTTGGTTACTTCC
ACTTTGAACTCCTCCATTCCATTTGAGCTTTCTtaa B: BoNTF(H_N) encoded protein SEQ ID NO: 30

MAPPRLCIRVNNSELFFVASESSYNENDINTPKEIDDTTNLNNNYRNNLDEVI
LDYNSQTIPQISNRTLNTLVQDNSYVPRYDSNGTSEIEEYDVVDFNVFFYLH
AQKVPEGETNISLTSSIDTALLEESKDIFFSSEFIDTINKPVNAALFIDWISKVIR
DFTTEATQKSTVDKIADISLIVPYVGLALNIIIEAEKGNFEEAFELLGVGILLEF
VPELTIPVILVFTIKSYIDSYENKNKAIKAINNSLIEREAKWKEIYSWIVSNWL
TRINTQFNKRKEQMYQALQNQVDAIKTAIEYKYNNYTSDEKNRLESEYNIN
NIEEELNKKVSLAMKNIERFMTESSISYLMKLINEAKVGKLKKYDNHVKSDL
LNYILDHRSILGEQTNELSDLVTSTLNSSIPFELS*

FIGURE 17

A: BoNTG(H$_N$) synthetic gene SEQ ID NO: 31 atggccAAAAATACCGGTAAATCTGAACAGTGTATTATTGTTAATAATGAG
GATTTATTTTTCATAGCTAATAAAGATAGTTTTTCAAAAGATTTAGCTAA
AGCAGAAACTATAGCATATAATACACAAAATAATACTATAGAAAATAAT
TTTTCTATAGATCAGTTGATTTTAGATAATGATTTAAGCAGTGGCATAGA
CTTACCAAATGAAACACAGAACCATTTACAAATTTTGACGACATAGAT
ATCCCTGTGTATATTAAACAATCTGCTTTAAAAAAAATTTTTGTGGATGG
AGATAGCCTTTTTGAATATTTACATGCTCAAACATTTCCTTCTAATATAG
AAAATCTACAACTAACGAATTCATTAAATGATGCTTTAAGAAATAATAA
TAAAGTCTATACTTTTTTTCTACAAACCTTGTTGAAAAAGCTAATACAG
TTGTAGGTGCTTCACTTTTTGTAAACTGGGTAAAAGGAGTAATAGATGAT
TTTACATCTGAATCCACACAAAAAGTACTATAGATAAAGTTTCAGATGT
ATCCATAATTATTCCCTATATAGGACCTGCTTTGAATGTAGGAAATGAAA
CAGCTAAAGAAATTTTAAAAATGCTTTTGAAATAGGTGGAGCCGCTAT
CTTAATGGAGTTTATTCCAGAACTTATTGTACCTATAGTTGGATTTTTAC
ATTAGAATCATATGTAGGAAATAAAGGGCATATTATTATGACGATATCC
AATGCTTTAAAGAAAAGGGATCAAAAATGGACAGATATGTATGGTTTGA
TAGTATCGCAGTGGCTCTCAACGGTTAATACTCAATTTTATACAATAAAA
GAAAGAATGTACAATGCTTTAAATAATCAATCACAAGCAATAGAAAAA
TAATAGAAGATCAATATAATAGATATAGTGAAGAAGATAAAATGAATAT
TAACATTGATTTTAATGATATAGATTTTAAACTTAATCAAAGTATAAATT
TAGCAATAAACAATATAGATGATTTTATAAACCAATGTTCTATATCATAT
CTAATGAATAGAATGATTCCATTAGCTGTAAAAAAGTTAAAAGACTTTG
ATGATAATCTTAAGAGAGATTTATTGGAGTATATAGATACAAATGAACT
ATATTTACTTGATGAAGTAAATATTCTAAAATCAAAAGTAAATAGACAC
CTAAAAGACAGTATACCATTTGATCTTTCACTATATACCtaa B: BoNTG(H$_N$) encoded protein SEQ ID NO: 32

MAKNTGKSEQCIIVNNEDLFFIANKDSFSKDLAKAETIAYNTQNNTIENNFSI
DQLILDNDLSSGIDLPNENTEPFTNFDDIDIPVYIKQSALKKIFVDGDSLFEYL
HAQTFPSNIENLQLTNSLNDALRNNNKVYTFFSTNLVEKANTVVGASLFVN
WVKGVIDDFTSESTQKSTIDKVSDVSIIIPYIGPALNVGNETAKENFKNAFEIG
GAAILMEFIPELIVPIVGFFTLESYVGNKGHIIMTISNALKKRDQKWTDMYGL
IVSQWLSTVNTQFYTIKERMYNALNNQSQAIEKIIEDQYNRYSEEDKMNINI
DFNDIDFKLNQSINLAINNIDDFINQCSISYLMNRMIPLAVKKLKDFDDNLKR
DLLEYIDTNELYLLDEVNILKSKVNRHLKDSIPFDLSLYT*

FIGURE 18

A: First BoNTF(Hc) gene: SEQ ID NO: 33

GAATTCACGatgTCTTACACTAACGACAAAATCCTGATCCTGTACTTCAAC
AAACTGTACAAAAAAATCAAAGACAACTCTATCCTGGACATGCGTTACG
AAAACAACAAATTCATCGACATCTCTGGCTATGGTTCTAACATCTCTATC
AACGGTGACGTCTACATCTACTCTACTAACCGCAACCAGTTCGGTATCTA
CTCTTCTAAACCGTCTGAAGTAAACATCGCTCAGAACAACGACATCATCT
ACAACGGTCGTTACCAGAACTTCTCTATCTCTTTCTGGGTTCGTATCCCG
AAATACTTCAACAAAGTTAACCTGAACAACGAATACACTATCATCGACT
GCATCCGTAACAACAACTCTGGTTGGAAATCTCTCTGAACTACAACAA
AATCATCTGGACTCTGCAGGACACTGCTGGTAACAACCAGAAACTGGTT
TTCAACTACACTCAGATGATCTCTATCTCTGACTACATTAATAAATGGAT
CTTCGTTACTATCACTAACAACCGTCTGGGTAACTCTCGTATCTACATCA
ACGGTAACCTGATCGATGAAAAATCTATCTCTAACCTGGGTGACATCCA
CGTTTCTGACAACATCCTGTTCAAAATCGTTGGTTGCAACGACACGCGTT
ACGTTGGTATCCGTTACTTCAAAGTTTTCGACACTGAACTGGGTAAAACT
GAAATCGAAACTCTGTACTCTGACGAACCGGACCCGTCTATCCTGAAAG
ACTTCTGGGGTAACTACCTGCTGTACAACAAACGTTACTACCTGCTGAAC
CTGCTCCGGACTGACAAATCTATCACTCAGAACTCTAACTTCCTGAACAT
CAACCAGCAGCGTGGTGTTTATCAGAAACCTAATATCTTCTCTAACACTC
GTCTGTACACTGGTGTTGAAGTTATCATCCGTAAAAACGGTTCTACTGAC
ATCTCTAACACTGACAACTTCGTACGTAAAAACGACCTGGCTTACATCAA
CGTTGTTGACCGTGACGTTGAATACCGTCTGTACGCTGACATCTCTATCG
CTAAACCGGAAAAAATCATCAAACTGATCCGTACTTCTAACTCTAACAA
CTCTCTGGGTCAGATCATCGTTATGGACTCGATCGGTAACAACTGCACTA
TGAACTTCCAGAACAACAACGGTGGTAACATCGGTCTGCTGGGTTTCCA
CTCTAACAACCTGGTTGCTTCTTCATGGTACTACAACAACATCCGTAAAA
ACACTTCTTCTAACGGTTGCTTCTGGTCTTTCATCTCTAAAGAACACGGTT
GGCAGGAAAACtaaGAATTC

B: BoNTF(Hc) #1 encoded protein: SEQ ID NO: 34

MSYTNDKILILYFNKLYKKIKDNSILDMRYENNKFIDISGYGSNISINGDVYIY
STNRNQFGIYSSKPSEVNIAQNNDIIYNGRYQNFSISFWVRIPKYFNKVNLNN
EYTIIDCIRNNNSGWKISLNYNKIIWTLQDTAGNNQKLVFNYTQMISISDYIN
KWIFVTITNNRLGNSRIYINGNLIDEKSISNLGDIHVSDNILFKIVGCNDTRYV
GIRYFKVFDTELGKTEIETLYSDEPDPSILKDFWGNYLLYNKRYYLLNLLRT
DKSITQNSNFLNINQQRGVYQKPNIFSNTRLYTGVEVIIRKNGSTDISNTDNF
VRKNDLAYINVVDRDVEYRLYADISIAKPEKIIKLIRTSNSNNSLGQIIVMDSI
GNNCTMNFQNNNGGNIGLLGFHSNNLVASSWYYNNIRKNTSSNGCFWSFIS
KEHGWQEN*

A: Natural BoNTF(Hc) Gene

B: First BoNTF(Hc) Synthetic Gene

C: Second BoNTF(Hc) Synthetic Gene

Fig 19

SEQUENCE LISTING

<160> NUMBER OF SEQ ID NOS: 34

<210> SEQ ID NO 1
<211> LENGTH: 1332
<212> TYPE: DNA
<213> ORGANISM: Artificial Sequence
<220> FEATURE:
<223> OTHER INFORMATION: Synthetic construct based on Clostridium botulinum sequence
<221> NAME/KEY: CDS
<222> LOCATION: (13)...(1326)

<400> SEQUENCE: 1

```
gaattcgaaa cg atg cgt ctg ctg tct acc ttc act gaa tac atc aag aac      51
              Met Arg Leu Leu Ser Thr Phe Thr Glu Tyr Ile Lys Asn
                1               5                  10 atc atc aat acc tcc atc ctg aac ctg cgc tac gaa tcc aat cac ctg        99
Ile Ile Asn Thr Ser Ile Leu Asn Leu Arg Tyr Glu Ser Asn His Leu
 15              20                  25 atc gac ctg tct cgc tac gct tcc aaa atc aac atc ggt tct aaa gtt       147
Ile Asp Leu Ser Arg Tyr Ala Ser Lys Ile Asn Ile Gly Ser Lys Val
 30              35                  40                  45 aac ttc gat ccg atc gac aag aat cag atc cag ctg ttc aat ctg gaa       195
Asn Phe Asp Pro Ile Asp Lys Asn Gln Ile Gln Leu Phe Asn Leu Glu
                 50                  55                  60 tct tcc aaa atc gaa gtt atc ctg aag aat gct atc gta tac aac tct       243
Ser Ser Lys Ile Glu Val Ile Leu Lys Asn Ala Ile Val Tyr Asn Ser
                 65                  70                  75 atg tac gaa aac ttc tcc acc tcc ttc tgg atc cgt atc ccg aaa tac       291
Met Tyr Glu Asn Phe Ser Thr Ser Phe Trp Ile Arg Ile Pro Lys Tyr
         80                  85                  90 ttc aac tcc atc tct ctg aac aat gaa tac acc atc atc aac tgc atg       339
Phe Asn Ser Ile Ser Leu Asn Asn Glu Tyr Thr Ile Ile Asn Cys Met
         95                  100                 105 gaa aac aat tct ggt tgg aaa gta tct ctg aac tac ggt gaa atc atc       387
Glu Asn Asn Ser Gly Trp Lys Val Ser Leu Asn Tyr Gly Glu Ile Ile
110                 115                 120                 125 tgg act ctg cag gac act cag gaa atc aaa cag cgt gtt gta ttc aaa       435
Trp Thr Leu Gln Asp Thr Gln Glu Ile Lys Gln Arg Val Val Phe Lys
                130                 135                 140 tac tct cag atg atc aac atc tct gac tac atc aat cgc tgg atc ttc       483
Tyr Ser Gln Met Ile Asn Ile Ser Asp Tyr Ile Asn Arg Trp Ile Phe
                145                 150                 155 gtt acc atc acc aac aat cgt ctg aat aac tcc aaa atc tac atc aac       531
Val Thr Ile Thr Asn Asn Arg Leu Asn Asn Ser Lys Ile Tyr Ile Asn
                160                 165                 170 ggc cgt ctg atc gac cag aaa ccg atc tcc aat ctg ggt aac atc cac       579
Gly Arg Leu Ile Asp Gln Lys Pro Ile Ser Asn Leu Gly Asn Ile His
175                 180                 185 gct tct aat aac atc atg ttc aaa ctg gac ggt tgt cgt gac act cac       627
Ala Ser Asn Asn Ile Met Phe Lys Leu Asp Gly Cys Arg Asp Thr His
190                 195                 200                 205 cgc tac atc tgg atc aaa tac ttc aat ctg ttc gac aaa gaa ctg aac       675
Arg Tyr Ile Trp Ile Lys Tyr Phe Asn Leu Phe Asp Lys Glu Leu Asn
                210                 215                 220 gaa aaa gaa atc aaa gac ctg tac gac aac cag tcc aat tct ggt atc       723
Glu Lys Glu Ile Lys Asp Leu Tyr Asp Asn Gln Ser Asn Ser Gly Ile
                225                 230                 235 ctg aaa gac ttc tgg ggt gac tac ctg cag tac gac aaa ccg tac tac       771
Leu Lys Asp Phe Trp Gly Asp Tyr Leu Gln Tyr Asp Lys Pro Tyr Tyr
```

-continued

```
                    240                 245                 250
atg ctg aat ctg tac gat ccg aac aaa tac gtt gac gtc aac aat gta      819
Met Leu Asn Leu Tyr Asp Pro Asn Lys Tyr Val Asp Val Asn Asn Val
    255                 260                 265 ggt atc cgc ggt tac atg tac ctg aaa ggt ccg cgt ggt tct gtt atg      867
Gly Ile Arg Gly Tyr Met Tyr Leu Lys Gly Pro Arg Gly Ser Val Met
270                 275                 280                 285 act acc aac atc tac ctg aac tct tcc ctg tac cgt ggt acc aaa ttc      915
Thr Thr Asn Ile Tyr Leu Asn Ser Ser Leu Tyr Arg Gly Thr Lys Phe
                290                 295                 300 atc atc aag aaa tac gcg tct ggt aac aag gac aat atc gtt cgc aac      963
Ile Ile Lys Lys Tyr Ala Ser Gly Asn Lys Asp Asn Ile Val Arg Asn
            305                 310                 315 aat gat cgt gta tac atc aat gtt gta gtt aag aac aaa gaa tac cgt     1011
Asn Asp Arg Val Tyr Ile Asn Val Val Val Lys Asn Lys Glu Tyr Arg
        320                 325                 330 ctg gct acc aat gct tct cag gct ggt gta gaa aag atc ttg tct gct     1059
Leu Ala Thr Asn Ala Ser Gln Ala Gly Val Glu Lys Ile Leu Ser Ala
    335                 340                 345 ctg gaa atc ccg gac gtt ggt aat ctg tct cag gta gtt gta atg aaa     1107
Leu Glu Ile Pro Asp Val Gly Asn Leu Ser Gln Val Val Val Met Lys
350                 355                 360                 365 tcc aag aac gac cag ggt atc act aac aaa tgc aaa atg aat ctg cag     1155
Ser Lys Asn Asp Gln Gly Ile Thr Asn Lys Cys Lys Met Asn Leu Gln
                370                 375                 380 gac aac aat ggt aac gat atc ggt ttc atc ggt ttc cac cag ttc aac     1203
Asp Asn Asn Gly Asn Asp Ile Gly Phe Ile Gly Phe His Gln Phe Asn
            385                 390                 395 aat atc gct aaa ctg gtt gct tcc aac tgg tac aat cgt cag atc gaa     1251
Asn Ile Ala Lys Leu Val Ala Ser Asn Trp Tyr Asn Arg Gln Ile Glu
        400                 405                 410 cgt tcc tct cgc act ctg ggt tgc tct tgg gag ttc atc ccg gtt gat     1299
Arg Ser Ser Arg Thr Leu Gly Cys Ser Trp Glu Phe Ile Pro Val Asp
    415                 420                 425 gac ggt tgg ggt gaa cgt ccg ctg taa gaattc                          1332
Asp Gly Trp Gly Glu Arg Pro Leu  *
430                 435
```

<210> SEQ ID NO 2
<211> LENGTH: 437
<212> TYPE: PRT
<213> ORGANISM: Artificial Sequence
<220> FEATURE:
<223> OTHER INFORMATION: Synthetic construct based on Clostridium botulinum sequence

<400> SEQUENCE: 2

```
Met Arg Leu Leu Ser Thr Phe Thr Glu Tyr Ile Lys Asn Ile Ile Asn
1               5                   10                  15

Thr Ser Ile Leu Asn Leu Arg Tyr Glu Ser Asn His Leu Ile Asp Leu
            20                  25                  30

Ser Arg Tyr Ala Ser Lys Ile Asn Ile Gly Ser Lys Val Asn Phe Asp
        35                  40                  45

Pro Ile Asp Lys Asn Gln Ile Gln Leu Phe Asn Leu Glu Ser Ser Lys
    50                  55                  60

Ile Glu Val Ile Leu Lys Asn Ala Ile Val Tyr Asn Ser Met Tyr Glu
65                  70                  75                  80

Asn Phe Ser Thr Ser Phe Trp Ile Arg Ile Pro Lys Tyr Phe Asn Ser
                85                  90                  95
```

```
Ile Ser Leu Asn Asn Glu Tyr Thr Ile Ile Asn Cys Met Glu Asn Asn
            100                 105                 110
Ser Gly Trp Lys Val Ser Leu Asn Tyr Gly Glu Ile Ile Trp Thr Leu
        115                 120                 125
Gln Asp Thr Gln Glu Ile Lys Gln Arg Val Val Phe Lys Tyr Ser Gln
    130                 135                 140
Met Ile Asn Ile Ser Asp Tyr Ile Asn Arg Trp Ile Phe Val Thr Ile
145                 150                 155                 160
Thr Asn Asn Arg Leu Asn Asn Ser Lys Ile Tyr Ile Asn Gly Arg Leu
                165                 170                 175
Ile Asp Gln Lys Pro Ile Ser Asn Leu Gly Asn Ile His Ala Ser Asn
            180                 185                 190
Asn Ile Met Phe Lys Leu Asp Gly Cys Arg Asp Thr His Arg Tyr Ile
        195                 200                 205
Trp Ile Lys Tyr Phe Asn Leu Phe Asp Lys Glu Leu Asn Glu Lys Glu
    210                 215                 220
Ile Lys Asp Leu Tyr Asp Asn Gln Ser Asn Ser Gly Ile Leu Lys Asp
225                 230                 235                 240
Phe Trp Gly Asp Tyr Leu Gln Tyr Asp Lys Pro Tyr Tyr Met Leu Asn
                245                 250                 255
Leu Tyr Asp Pro Asn Lys Tyr Val Asp Val Asn Asn Val Gly Ile Arg
            260                 265                 270
Gly Tyr Met Tyr Leu Lys Gly Pro Arg Gly Ser Val Met Thr Thr Asn
        275                 280                 285
Ile Tyr Leu Asn Ser Ser Leu Tyr Arg Gly Thr Lys Phe Ile Ile Lys
    290                 295                 300
Lys Tyr Ala Ser Gly Asn Lys Asp Asn Ile Val Arg Asn Asn Asp Arg
305                 310                 315                 320
Val Tyr Ile Asn Val Val Val Lys Asn Lys Glu Tyr Arg Leu Ala Thr
                325                 330                 335
Asn Ala Ser Gln Ala Gly Val Glu Lys Ile Leu Ser Ala Leu Glu Ile
            340                 345                 350
Pro Asp Val Gly Asn Leu Ser Gln Val Val Val Met Lys Ser Lys Asn
        355                 360                 365
Asp Gln Gly Ile Thr Asn Lys Cys Lys Met Asn Leu Gln Asp Asn Asn
    370                 375                 380
Gly Asn Asp Ile Gly Phe Ile Gly Phe His Gln Phe Asn Asn Ile Ala
385                 390                 395                 400
Lys Leu Val Ala Ser Asn Trp Tyr Asn Arg Gln Ile Glu Arg Ser Ser
                405                 410                 415
Arg Thr Leu Gly Cys Ser Trp Glu Phe Ile Pro Val Asp Asp Gly Trp
            420                 425                 430
Gly Glu Arg Pro Leu
        435

<210> SEQ ID NO 3
<211> LENGTH: 1323
<212> TYPE: DNA
<213> ORGANISM: Artificial Sequence
<220> FEATURE:
<223> OTHER INFORMATION: Synthetic construct based on Clostridium
      botulinum sequence
<221> NAME/KEY: CDS
<222> LOCATION: (13)...(1314)
<223> OTHER INFORMATION: Synthetic Construct

<400> SEQUENCE: 3
```

```
gaattcgaaa cg atg tct acc ttc act gaa tac atc aag aac atc atc aat        51
              Met Ser Thr Phe Thr Glu Tyr Ile Lys Asn Ile Ile Asn
                1               5                  10 acc tcc atc ctg aac ctg cgc tac gaa tcc aat cac ctg atc gac ctg          99
Thr Ser Ile Leu Asn Leu Arg Tyr Glu Ser Asn His Leu Ile Asp Leu
 15                  20                  25 tct cgc tac gct tcc aaa atc aac atc ggt tct aaa gtt aac ttc gat         147
Ser Arg Tyr Ala Ser Lys Ile Asn Ile Gly Ser Lys Val Asn Phe Asp
 30                  35                  40                  45 ccg atc gac aag aat cag atc cag ctg ttc aat ctg gaa tct tcc aaa         195
Pro Ile Asp Lys Asn Gln Ile Gln Leu Phe Asn Leu Glu Ser Ser Lys
                 50                  55                  60 atc gaa gtt atc ctg aag aat gct atc gta tac aac tct atg tac gaa         243
Ile Glu Val Ile Leu Lys Asn Ala Ile Val Tyr Asn Ser Met Tyr Glu
                     65                  70                  75 aac ttc tcc acc tcc ttc tgg atc cgt atc ccg aaa tac ttc aac tcc         291
Asn Phe Ser Thr Ser Phe Trp Ile Arg Ile Pro Lys Tyr Phe Asn Ser
         80                  85                  90 atc tct ctg aac aat gaa tac acc atc atc aac tgc atg gaa aac aat         339
Ile Ser Leu Asn Asn Glu Tyr Thr Ile Ile Asn Cys Met Glu Asn Asn
 95                 100                 105 tct ggt tgg aaa gta tct ctg aac tac ggt gaa atc atc tgg act ctg         387
Ser Gly Trp Lys Val Ser Leu Asn Tyr Gly Glu Ile Ile Trp Thr Leu
110                 115                 120                 125 cag gac act cag gaa atc aaa cag cgt gtt gta ttc aaa tac tct cag         435
Gln Asp Thr Gln Glu Ile Lys Gln Arg Val Val Phe Lys Tyr Ser Gln
                130                 135                 140 atg atc aac atc tct gac tac atc aat cgc tgg atc ttc gtt acc atc         483
Met Ile Asn Ile Ser Asp Tyr Ile Asn Arg Trp Ile Phe Val Thr Ile
                145                 150                 155 acc aac aat cgt ctg aat aac tcc aaa atc tac atc aac ggc cgt ctg         531
Thr Asn Asn Arg Leu Asn Asn Ser Lys Ile Tyr Ile Asn Gly Arg Leu
        160                 165                 170 atc gac cag aaa ccg atc tcc aat ctg ggt aac atc cac gct tct aat         579
Ile Asp Gln Lys Pro Ile Ser Asn Leu Gly Asn Ile His Ala Ser Asn
175                 180                 185 aac atc atg ttc aaa ctg gac ggt tgt cgt gac act cac cgc tac atc         627
Asn Ile Met Phe Lys Leu Asp Gly Cys Arg Asp Thr His Arg Tyr Ile
190                 195                 200                 205 tgg atc aaa tac ttc aat ctg ttc gac aaa gaa ctg aac gaa aaa gaa         675
Trp Ile Lys Tyr Phe Asn Leu Phe Asp Lys Glu Leu Asn Glu Lys Glu
                210                 215                 220 atc aaa gac ctg tac gac aac cag tcc aat tct ggt atc ctg aaa gac         723
Ile Lys Asp Leu Tyr Asp Asn Gln Ser Asn Ser Gly Ile Leu Lys Asp
                225                 230                 235 ttc tgg ggt gac tac ctg cag tac gac aaa ccg tac tac atg ctg aat         771
Phe Trp Gly Asp Tyr Leu Gln Tyr Asp Lys Pro Tyr Tyr Met Leu Asn
                240                 245                 250 ctg tac gat ccg aac aaa tac gtt gac gtc aac aat gta ggt atc cgc         819
Leu Tyr Asp Pro Asn Lys Tyr Val Asp Val Asn Asn Val Gly Ile Arg
        255                 260                 265 ggt tac atg tac ctg aaa ggt ccg cgt ggt tct gtt atg act acc aac         867
Gly Tyr Met Tyr Leu Lys Gly Pro Arg Gly Ser Val Met Thr Thr Asn
270                 275                 280                 285 atc tac ctg aac tct tcc ctg tac cgt ggt acc aaa ttc atc atc aag         915
Ile Tyr Leu Asn Ser Ser Leu Tyr Arg Gly Thr Lys Phe Ile Ile Lys
                290                 295                 300
```

```
aaa tac gcg tct ggt aac aag gac aat atc gtt cgc aac aat gat cgt    963
Lys Tyr Ala Ser Gly Asn Lys Asp Asn Ile Val Arg Asn Asn Asp Arg
            305                 310                 315 gta tac atc aat gtt gta gtt aag aac aaa gaa tac cgt ctg gct acc   1011
Val Tyr Ile Asn Val Val Val Lys Asn Lys Glu Tyr Arg Leu Ala Thr
        320                 325                 330 aat gct tct cag gct ggt gta gaa aag atc ttg tct gct ctg gaa atc   1059
Asn Ala Ser Gln Ala Gly Val Glu Lys Ile Leu Ser Ala Leu Glu Ile
    335                 340                 345 ccg gac gtt ggt aat ctg tct cag gta gtt gta atg aaa tcc aag aac   1107
Pro Asp Val Gly Asn Leu Ser Gln Val Val Val Met Lys Ser Lys Asn
350                 355                 360                 365 gac cag ggt atc act aac aaa tgc aaa atg aat ctg cag gac aac aat   1155
Asp Gln Gly Ile Thr Asn Lys Cys Lys Met Asn Leu Gln Asp Asn Asn
                370                 375                 380 ggt aac gat atc ggt ttc atc ggt ttc cac cag ttc aac aat atc gct   1203
Gly Asn Asp Ile Gly Phe Ile Gly Phe His Gln Phe Asn Asn Ile Ala
            385                 390                 395 aaa ctg gtt gct tcc aac tgg tac aat cgt cag atc gaa cgt tcc tct   1251
Lys Leu Val Ala Ser Asn Trp Tyr Asn Arg Gln Ile Glu Arg Ser Ser
        400                 405                 410 cgc act ctg ggt tgc tct tgg gag ttc atc ccg gtt gat gac ggt tgg   1299
Arg Thr Leu Gly Cys Ser Trp Glu Phe Ile Pro Val Asp Asp Gly Trp
    415                 420                 425 ggt gaa cgt ccg ctg taagaattc                                     1323
Gly Glu Arg Pro Leu
430
```

<210> SEQ ID NO 4
<211> LENGTH: 434
<212> TYPE: PRT
<213> ORGANISM: Artificial Sequence
<220> FEATURE:
<223> OTHER INFORMATION: Synthetic construct based on Clostridium
      botulinum sequence

<400> SEQUENCE: 4

Met Ser Thr Phe Thr Glu Tyr Ile Lys Asn Ile Ile Asn Thr Ser Ile
1               5                   10                  15

Leu Asn Leu Arg Tyr Glu Ser Asn His Leu Ile Asp Leu Ser Arg Tyr
            20                  25                  30

Ala Ser Lys Ile Asn Ile Gly Ser Lys Val Asn Phe Asp Pro Ile Asp
        35                  40                  45

Lys Asn Gln Ile Gln Leu Phe Asn Leu Glu Ser Ser Lys Ile Glu Val
    50                  55                  60

Ile Leu Lys Asn Ala Ile Val Tyr Asn Ser Met Tyr Glu Asn Phe Ser
65                  70                  75                  80

Thr Ser Phe Trp Ile Arg Ile Pro Lys Tyr Phe Asn Ser Ile Ser Leu
                85                  90                  95

Asn Asn Glu Tyr Thr Ile Ile Asn Cys Met Glu Asn Asn Ser Gly Trp
            100                 105                 110

Lys Val Ser Leu Asn Tyr Gly Glu Ile Ile Trp Thr Leu Gln Asp Thr
        115                 120                 125

Gln Glu Ile Lys Gln Arg Val Val Phe Lys Tyr Ser Gln Met Ile Asn
    130                 135                 140

Ile Ser Asp Tyr Ile Asn Arg Trp Ile Phe Val Thr Ile Thr Asn Asn
145                 150                 155                 160

```
Arg Leu Asn Asn Ser Lys Ile Tyr Ile Asn Gly Arg Leu Ile Asp Gln
                165                 170                 175

Lys Pro Ile Ser Asn Leu Gly Asn Ile His Ala Ser Asn Asn Ile Met
            180                 185                 190

Phe Lys Leu Asp Gly Cys Arg Asp Thr His Arg Tyr Ile Trp Ile Lys
        195                 200                 205

Tyr Phe Asn Leu Phe Asp Lys Glu Leu Asn Glu Lys Glu Ile Lys Asp
    210                 215                 220

Leu Tyr Asp Asn Gln Ser Asn Ser Gly Ile Leu Lys Asp Phe Trp Gly
225                 230                 235                 240

Asp Tyr Leu Gln Tyr Asp Lys Pro Tyr Tyr Met Leu Asn Leu Tyr Asp
                245                 250                 255

Pro Asn Lys Tyr Val Asp Val Asn Asn Val Gly Ile Arg Gly Tyr Met
            260                 265                 270

Tyr Leu Lys Gly Pro Arg Gly Ser Val Met Thr Thr Asn Ile Tyr Leu
        275                 280                 285

Asn Ser Ser Leu Tyr Arg Gly Thr Lys Phe Ile Ile Lys Lys Tyr Ala
    290                 295                 300

Ser Gly Asn Lys Asp Asn Ile Val Arg Asn Asn Asp Arg Val Tyr Ile
305                 310                 315                 320

Asn Val Val Val Lys Asn Lys Glu Tyr Arg Leu Ala Thr Asn Ala Ser
                325                 330                 335

Gln Ala Gly Val Glu Lys Ile Leu Ser Ala Leu Glu Ile Pro Asp Val
            340                 345                 350

Gly Asn Leu Ser Gln Val Val Val Met Lys Ser Lys Asn Asp Gln Gly
        355                 360                 365

Ile Thr Asn Lys Cys Lys Met Asn Leu Gln Asp Asn Asn Gly Asn Asp
    370                 375                 380

Ile Gly Phe Ile Gly Phe His Gln Phe Asn Asn Ile Ala Lys Leu Val
385                 390                 395                 400

Ala Ser Asn Trp Tyr Asn Arg Gln Ile Glu Arg Ser Ser Arg Thr Leu
                405                 410                 415

Gly Cys Ser Trp Glu Phe Ile Pro Val Asp Asp Gly Trp Gly Glu Arg
            420                 425                 430

Pro Leu

<210> SEQ ID NO 5
<211> LENGTH: 1326
<212> TYPE: DNA
<213> ORGANISM: Artificial Sequence
<220> FEATURE:
<223> OTHER INFORMATION: Synthetic construct based on Clostridium
      botulinum sequence
<221> NAME/KEY: CDS
<222> LOCATION: (13)...(1317)

<400> SEQUENCE: 5
gaattcgaaa cg atg gcc tct acc ttc act gaa tac atc aag aac atc atc     51
              Met Ala Ser Thr Phe Thr Glu Tyr Ile Lys Asn Ile Ile
                1               5                   10 aat acc tcc atc ctg aac ctg cgc tac gaa tcc aat cac ctg atc gac     99
Asn Thr Ser Ile Leu Asn Leu Arg Tyr Glu Ser Asn His Leu Ile Asp
 15                  20                  25 ctg tct cgc tac gct tcc aaa atc aac atc ggt tct aaa gtt aac ttc    147
Leu Ser Arg Tyr Ala Ser Lys Ile Asn Ile Gly Ser Lys Val Asn Phe
 30                  35                  40                  45
```

```
gat ccg atc gac aag aat cag atc cag ctg ttc aat ctg gaa tct tcc      195
Asp Pro Ile Asp Lys Asn Gln Ile Gln Leu Phe Asn Leu Glu Ser Ser
             50                  55                  60 aaa atc gaa gtt atc ctg aag aat gct atc gta tac aac tct atg tac      243
Lys Ile Glu Val Ile Leu Lys Asn Ala Ile Val Tyr Asn Ser Met Tyr
         65                  70                  75 gaa aac ttc tcc acc tcc ttc tgg atc cgt atc ccg aaa tac ttc aac      291
Glu Asn Phe Ser Thr Ser Phe Trp Ile Arg Ile Pro Lys Tyr Phe Asn
     80                  85                  90 tcc atc tct ctg aac aat gaa tac acc atc atc aac tgc atg gaa aac      339
Ser Ile Ser Leu Asn Asn Glu Tyr Thr Ile Ile Asn Cys Met Glu Asn
 95                 100                 105 aat tct ggt tgg aaa gta tct ctg aac tac ggt gaa atc atc tgg act      387
Asn Ser Gly Trp Lys Val Ser Leu Asn Tyr Gly Glu Ile Ile Trp Thr
110                 115                 120                 125 ctg cag gac act cag gaa atc aaa cag cgt gtt gta ttc aaa tac tct      435
Leu Gln Asp Thr Gln Glu Ile Lys Gln Arg Val Val Phe Lys Tyr Ser
            130                 135                 140 cag atg atc aac atc tct gac tac atc aat cgc tgg atc ttc gtt acc      483
Gln Met Ile Asn Ile Ser Asp Tyr Ile Asn Arg Trp Ile Phe Val Thr
        145                 150                 155 atc acc aac aat cgt ctg aat aac tcc aaa atc tac atc aac ggc cgt      531
Ile Thr Asn Asn Arg Leu Asn Asn Ser Lys Ile Tyr Ile Asn Gly Arg
    160                 165                 170 ctg atc gac cag aaa ccg atc tcc aat ctg ggt aac atc cac gct tct      579
Leu Ile Asp Gln Lys Pro Ile Ser Asn Leu Gly Asn Ile His Ala Ser
175                 180                 185 aat aac atc atg ttc aaa ctg gac ggt tgt cgt gac act cac cgc tac      627
Asn Asn Ile Met Phe Lys Leu Asp Gly Cys Arg Asp Thr His Arg Tyr
190                 195                 200                 205 atc tgg atc aaa tac ttc aat ctg ttc gac aaa gaa ctg aac gaa aaa      675
Ile Trp Ile Lys Tyr Phe Asn Leu Phe Asp Lys Glu Leu Asn Glu Lys
            210                 215                 220 gaa atc aaa gac ctg tac gac aac cag tcc aat tct ggt atc ctg aaa      723
Glu Ile Lys Asp Leu Tyr Asp Asn Gln Ser Asn Ser Gly Ile Leu Lys
        225                 230                 235 gac ttc tgg ggt gac tac ctg cag tac gac aaa ccg tac tac atg ctg      771
Asp Phe Trp Gly Asp Tyr Leu Gln Tyr Asp Lys Pro Tyr Tyr Met Leu
    240                 245                 250 aat ctg tac gat ccg aac aaa tac gtt gac gtc aac aat gta ggt atc      819
Asn Leu Tyr Asp Pro Asn Lys Tyr Val Asp Val Asn Asn Val Gly Ile
255                 260                 265 cgc ggt tac atg tac ctg aaa ggt ccg cgt ggt tct gtt atg act acc      867
Arg Gly Tyr Met Tyr Leu Lys Gly Pro Arg Gly Ser Val Met Thr Thr
270                 275                 280                 285 aac atc tac ctg aac tct tcc ctg tac cgt ggt acc aaa ttc atc atc      915
Asn Ile Tyr Leu Asn Ser Ser Leu Tyr Arg Gly Thr Lys Phe Ile Ile
            290                 295                 300 aag aaa tac gcg tct ggt aac aag gac aat atc gtt cgc aac aat gat      963
Lys Lys Tyr Ala Ser Gly Asn Lys Asp Asn Ile Val Arg Asn Asn Asp
        305                 310                 315 cgt gta tac atc aat gtt gta gtt aag aac aaa gaa tac cgt ctg gct     1011
Arg Val Tyr Ile Asn Val Val Val Lys Asn Lys Glu Tyr Arg Leu Ala
    320                 325                 330 acc aat gct tct cag gct ggt gta gaa aag atc ttg tct gct ctg gaa     1059
Thr Asn Ala Ser Gln Ala Gly Val Glu Lys Ile Leu Ser Ala Leu Glu
335                 340                 345 atc ccg gac gtt ggt aat ctg tct cag gta gtt gta atg aaa tcc aag     1107
Ile Pro Asp Val Gly Asn Leu Ser Gln Val Val Val Met Lys Ser Lys
350                 355                 360                 365
```

```
aac gac cag ggt atc act aac aaa tgc aaa atg aat ctg cag gac aac    1155
Asn Asp Gln Gly Ile Thr Asn Lys Cys Lys Met Asn Leu Gln Asp Asn
                370                 375                 380 aat ggt aac gat atc ggt ttc atc ggt ttc cac cag ttc aac aat atc    1203
Asn Gly Asn Asp Ile Gly Phe Ile Gly Phe His Gln Phe Asn Asn Ile
            385                 390                 395 gct aaa ctg gtt gct tcc aac tgg tac aat cgt cag atc gaa cgt tcc    1251
Ala Lys Leu Val Ala Ser Asn Trp Tyr Asn Arg Gln Ile Glu Arg Ser
        400                 405                 410 tct cgc act ctg ggt tgc tct tgg gag ttc atc ccg gtt gat gac ggt    1299
Ser Arg Thr Leu Gly Cys Ser Trp Glu Phe Ile Pro Val Asp Asp Gly
    415                 420                 425 tgg ggt gaa cgt ccg ctg taagaattc                                  1326
Trp Gly Glu Arg Pro Leu
430             435

<210> SEQ ID NO 6
<211> LENGTH: 435
<212> TYPE: PRT
<213> ORGANISM: Artificial Sequence
<220> FEATURE:
<223> OTHER INFORMATION: Synthetic construct based on Clostridium
      botulinum sequence

<400> SEQUENCE: 6

Met Ala Ser Thr Phe Thr Glu Tyr Ile Lys Asn Ile Ile Asn Thr Ser
1               5                   10                  15

Ile Leu Asn Leu Arg Tyr Glu Ser Asn His Leu Ile Asp Leu Ser Arg
            20                  25                  30

Tyr Ala Ser Lys Ile Asn Ile Gly Ser Lys Val Asn Phe Asp Pro Ile
        35                  40                  45

Asp Lys Asn Gln Ile Gln Leu Phe Asn Leu Glu Ser Ser Lys Ile Glu
    50                  55                  60

Val Ile Leu Lys Asn Ala Ile Val Tyr Asn Ser Met Tyr Glu Asn Phe
65                  70                  75                  80

Ser Thr Ser Phe Trp Ile Arg Ile Pro Lys Tyr Phe Asn Ser Ile Ser
                85                  90                  95

Leu Asn Asn Glu Tyr Thr Ile Ile Asn Cys Met Glu Asn Asn Ser Gly
            100                 105                 110

Trp Lys Val Ser Leu Asn Tyr Gly Glu Ile Ile Trp Thr Leu Gln Asp
        115                 120                 125

Thr Gln Glu Ile Lys Gln Arg Val Val Phe Lys Tyr Ser Gln Met Ile
    130                 135                 140

Asn Ile Ser Asp Tyr Ile Asn Arg Trp Ile Phe Val Thr Ile Thr Asn
145                 150                 155                 160

Asn Arg Leu Asn Asn Ser Lys Ile Tyr Ile Asn Gly Arg Leu Ile Asp
                165                 170                 175

Gln Lys Pro Ile Ser Asn Leu Gly Asn Ile His Ala Ser Asn Asn Ile
            180                 185                 190

Met Phe Lys Leu Asp Gly Cys Arg Asp Thr His Arg Tyr Ile Trp Ile
        195                 200                 205

Lys Tyr Phe Asn Leu Phe Asp Lys Glu Leu Asn Glu Lys Glu Ile Lys
    210                 215                 220

Asp Leu Tyr Asp Asn Gln Ser Asn Ser Gly Ile Leu Lys Asp Phe Trp
225                 230                 235                 240

Gly Asp Tyr Leu Gln Tyr Asp Lys Pro Tyr Tyr Met Leu Asn Leu Tyr
                245                 250                 255
```

```
Asp Pro Asn Lys Tyr Val Asp Val Asn Val Gly Ile Arg Gly Tyr
            260                 265                 270

Met Tyr Leu Lys Gly Pro Arg Gly Ser Val Met Thr Thr Asn Ile Tyr
        275                 280                 285

Leu Asn Ser Ser Leu Tyr Arg Gly Thr Lys Phe Ile Ile Lys Lys Tyr
    290                 295                 300

Ala Ser Gly Asn Lys Asp Asn Ile Val Arg Asn Asn Asp Arg Val Tyr
305                 310                 315                 320

Ile Asn Val Val Lys Asn Lys Glu Tyr Arg Leu Ala Thr Asn Ala
                325                 330                 335

Ser Gln Ala Gly Val Glu Lys Ile Leu Ser Ala Leu Glu Ile Pro Asp
            340                 345                 350

Val Gly Asn Leu Ser Gln Val Val Met Lys Ser Lys Asn Asp Gln
                355                 360                 365

Gly Ile Thr Asn Lys Cys Lys Met Asn Leu Gln Asp Asn Asn Gly Asn
            370                 375                 380

Asp Ile Gly Phe Ile Gly Phe His Gln Phe Asn Asn Ile Ala Lys Leu
385                 390                 395                 400

Val Ala Ser Asn Trp Tyr Asn Arg Gln Ile Glu Arg Ser Ser Arg Thr
                405                 410                 415

Leu Gly Cys Ser Trp Glu Phe Ile Pro Val Asp Asp Gly Trp Gly Glu
            420                 425                 430

Arg Pro Leu
        435

<210> SEQ ID NO 7
<211> LENGTH: 1341
<212> TYPE: DNA
<213> ORGANISM: Artificial Sequence
<220> FEATURE:
<223> OTHER INFORMATION: Synthetic construct based on Clostridium
      botulinum sequence
<221> NAME/KEY: CDS
<222> LOCATION: (10)...(1329)

<400> SEQUENCE: 7 gaattcacg atg gcc aac aaa tac aat tcc gaa atc ctg aac aat atc atc        51
          Met Ala Asn Lys Tyr Asn Ser Glu Ile Leu Asn Asn Ile Ile
            1               5                  10 ctg aac ctg cgt tac aaa gac aac aat ctg atc gat ctg tct ggt tac         99
Leu Asn Leu Arg Tyr Lys Asp Asn Asn Leu Ile Asp Leu Ser Gly Tyr
 15                  20                  25                  30 ggt gct aaa gtt gaa gta tac gac ggt gtt gaa ctg aat gac aag aac        147
Gly Ala Lys Val Glu Val Tyr Asp Gly Val Glu Leu Asn Asp Lys Asn
                 35                  40                  45 cag ttc aaa ctg acc tct tcc gct aac tct aag atc cgt gtt act cag        195
Gln Phe Lys Leu Thr Ser Ser Ala Asn Ser Lys Ile Arg Val Thr Gln
             50                  55                  60 aat cag aac atc atc ttc aac tcc gta ttc ctg gac ttc tct gtt tcc        243
Asn Gln Asn Ile Ile Phe Asn Ser Val Phe Leu Asp Phe Ser Val Ser
         65                  70                  75 ttc tgg att cgt atc ccg aaa tac aag aac gac ggt atc cag aat tac        291
Phe Trp Ile Arg Ile Pro Lys Tyr Lys Asn Asp Gly Ile Gln Asn Tyr
     80                  85                  90 atc cac aat gaa tac acc atc atc aac tgc atg aag aat aac tct ggt        339
Ile His Asn Glu Tyr Thr Ile Ile Asn Cys Met Lys Asn Asn Ser Gly
 95                 100                 105                 110
```

-continued

| | | |
|---|---|---|
| tgg aag atc tcc atc cgc ggt aac cgt atc atc tgg act ctg atc gat<br>Trp Lys Ile Ser Ile Arg Gly Asn Arg Ile Ile Trp Thr Leu Ile Asp<br>                115                          120                          125 | 387 |
| atc aac ggt aag acc aaa tct gta ttc ttc gaa tac aac atc cgt gaa<br>Ile Asn Gly Lys Thr Lys Ser Val Phe Phe Glu Tyr Asn Ile Arg Glu<br>130                        135                        140 | 435 |
| gac atc tct gaa tac atc aat cgc tgg ttc ttc gtt acc atc acc aat<br>Asp Ile Ser Glu Tyr Ile Asn Arg Trp Phe Phe Val Thr Ile Thr Asn<br>        145                      150                        155 | 483 |
| aac ctg aac aat gct aaa atc tac atc aac ggt aaa ctg gaa tct aat<br>Asn Leu Asn Asn Ala Lys Ile Tyr Ile Asn Gly Lys Leu Glu Ser Asn<br>160                        165                        170 | 531 |
| acc gac atc aaa gac atc cgt gaa gtt atc gct aac ggt gaa atc atc<br>Thr Asp Ile Lys Asp Ile Arg Glu Val Ile Ala Asn Gly Glu Ile Ile<br>175                        180                        185                        190 | 579 |
| ttc aaa ctg gac ggt gac atc gat cgt acc cag ttc atc tgg atg aaa<br>Phe Lys Leu Asp Gly Asp Ile Asp Arg Thr Gln Phe Ile Trp Met Lys<br>                        195                        200                        205 | 627 |
| tac ttc tcc atc ttc aac acc gaa ctg tct cag tcc aat atc gaa gaa<br>Tyr Phe Ser Ile Phe Asn Thr Glu Leu Ser Gln Ser Asn Ile Glu Glu<br>                210                        215                        220 | 675 |
| cgg tac aag atc cag tct tac tcc gaa tac ctg aaa gac ttc tgg ggt<br>Arg Tyr Lys Ile Gln Ser Tyr Ser Glu Tyr Leu Lys Asp Phe Trp Gly<br>        225                      230                        235 | 723 |
| aat ccg ctg atg tac aac aaa gaa tac tat atg ttc aat gct ggt aac<br>Asn Pro Leu Met Tyr Asn Lys Glu Tyr Tyr Met Phe Asn Ala Gly Asn<br>240                        245                        250 | 771 |
| aag aac tct tac atc aaa ctg aag aaa gac tct ccg gtt ggt gaa atc<br>Lys Asn Ser Tyr Ile Lys Leu Lys Lys Asp Ser Pro Val Gly Glu Ile<br>255                        260                        265                        270 | 819 |
| ctg act cgt tcc aaa tac aac cag aac tct aaa tac atc aac tac cgc<br>Leu Thr Arg Ser Lys Tyr Asn Gln Asn Ser Lys Tyr Ile Asn Tyr Arg<br>                        275                        280                        285 | 867 |
| gac ctg tac atc ggt gaa aag ttc atc atc cgt cgc aaa tct aac tct<br>Asp Leu Tyr Ile Gly Glu Lys Phe Ile Ile Arg Arg Lys Ser Asn Ser<br>                290                        295                        300 | 915 |
| cag tcc atc aat gat gac atc gta cgt aaa gaa gac tac atc tac ctg<br>Gln Ser Ile Asn Asp Asp Ile Val Arg Lys Glu Asp Tyr Ile Tyr Leu<br>        305                      310                        315 | 963 |
| gac ttc ttc aac ctg aat cag gaa tgg cgt gta tac acc tac aag tac<br>Asp Phe Phe Asn Leu Asn Gln Glu Trp Arg Val Tyr Thr Tyr Lys Tyr<br>320                        325                        330 | 1011 |
| ttc aag aaa gaa gaa gaa aag ctt ttc ctg gct ccg atc tct gat tcc<br>Phe Lys Lys Glu Glu Glu Lys Leu Phe Leu Ala Pro Ile Ser Asp Ser<br>335                        340                        345                        350 | 1059 |
| gac gaa ctc tac aac acc atc cag atc aaa gaa tac gac gaa cag ccg<br>Asp Glu Leu Tyr Asn Thr Ile Gln Ile Lys Glu Tyr Asp Glu Gln Pro<br>                        355                        360                        365 | 1107 |
| acc tac tct tgc cag ctg ctg ttc aag aaa gat gaa gaa tct act gac<br>Thr Tyr Ser Cys Gln Leu Leu Phe Lys Lys Asp Glu Glu Ser Thr Asp<br>                370                        375                        380 | 1155 |
| gaa atc ggt ctg atc ggt atc cac cgt ttc tac gaa tct ggt atc gta<br>Glu Ile Gly Leu Ile Gly Ile His Arg Phe Tyr Glu Ser Gly Ile Val<br>        385                      390                        395 | 1203 |
| ttc gaa gaa tac aaa gac tac ttc tgc atc tcc aaa tgg tac ctg aag<br>Phe Glu Glu Tyr Lys Asp Tyr Phe Cys Ile Ser Lys Trp Tyr Leu Lys<br>400                        405                        410 | 1251 |
| gaa gtt aaa cgc aaa ccg tac aac ctg aaa ctg ggt tgc aat tgg cag<br>Glu Val Lys Arg Lys Pro Tyr Asn Leu Lys Leu Gly Cys Asn Trp Gln<br>415                        420                        425                        430 | 1299 |

```
ttc atc ccg aaa gac gaa ggt tgg acc gaa tagtaagaat tc        1341
Phe Ile Pro Lys Asp Glu Gly Trp Thr Glu
            435                 440

<210> SEQ ID NO 8
<211> LENGTH: 440
<212> TYPE: PRT
<213> ORGANISM: Artificial Sequence
<220> FEATURE:
<223> OTHER INFORMATION: Synthetic construct based on Clostridium
      botulinum sequence

<400> SEQUENCE: 8

Met Ala Asn Lys Tyr Asn Ser Glu Ile Leu Asn Asn Ile Ile Leu Asn
1               5                   10                  15

Leu Arg Tyr Lys Asp Asn Leu Ile Asp Leu Ser Gly Tyr Gly Ala
            20                  25                  30

Lys Val Glu Val Tyr Asp Gly Val Glu Leu Asn Asp Lys Asn Gln Phe
            35                  40                  45

Lys Leu Thr Ser Ser Ala Asn Ser Lys Ile Arg Val Thr Gln Asn Gln
    50                  55                  60

Asn Ile Ile Phe Asn Ser Val Phe Leu Asp Phe Ser Val Ser Phe Trp
65                  70                  75                  80

Ile Arg Ile Pro Lys Tyr Lys Asn Asp Gly Ile Gln Asn Tyr Ile His
                85                  90                  95

Asn Glu Tyr Thr Ile Ile Asn Cys Met Lys Asn Asn Ser Gly Trp Lys
            100                 105                 110

Ile Ser Ile Arg Gly Asn Arg Ile Ile Trp Thr Leu Ile Asp Ile Asn
        115                 120                 125

Gly Lys Thr Lys Ser Val Phe Phe Glu Tyr Asn Ile Arg Glu Asp Ile
    130                 135                 140

Ser Glu Tyr Ile Asn Arg Trp Phe Phe Val Thr Ile Thr Asn Asn Leu
145                 150                 155                 160

Asn Asn Ala Lys Ile Tyr Ile Asn Gly Lys Leu Glu Ser Asn Thr Asp
                165                 170                 175

Ile Lys Asp Ile Arg Glu Val Ile Ala Asn Gly Glu Ile Ile Phe Lys
            180                 185                 190

Leu Asp Gly Asp Ile Asp Arg Thr Gln Phe Ile Trp Met Lys Tyr Phe
        195                 200                 205

Ser Ile Phe Asn Thr Glu Leu Ser Gln Ser Asn Ile Glu Glu Arg Tyr
    210                 215                 220

Lys Ile Gln Ser Tyr Ser Glu Tyr Leu Lys Asp Phe Trp Gly Asn Pro
225                 230                 235                 240

Leu Met Tyr Asn Lys Glu Tyr Tyr Met Phe Asn Ala Gly Asn Lys Asn
                245                 250                 255

Ser Tyr Ile Lys Leu Lys Lys Asp Ser Pro Val Gly Glu Ile Leu Thr
            260                 265                 270

Arg Ser Lys Tyr Asn Gln Asn Ser Lys Tyr Ile Asn Tyr Arg Asp Leu
        275                 280                 285

Tyr Ile Gly Glu Lys Phe Ile Ile Arg Arg Lys Ser Asn Ser Gln Ser
    290                 295                 300

Ile Asn Asp Asp Ile Val Arg Lys Glu Asp Tyr Ile Tyr Leu Asp Phe
305                 310                 315                 320

Phe Asn Leu Asn Gln Glu Trp Arg Val Tyr Thr Tyr Lys Tyr Phe Lys
                325                 330                 335
```

```
Lys Glu Glu Lys Leu Phe Leu Ala Pro Ile Ser Asp Ser Asp Glu
            340                 345                 350

Leu Tyr Asn Thr Ile Gln Ile Lys Glu Tyr Asp Glu Gln Pro Thr Tyr
            355                 360                 365

Ser Cys Gln Leu Leu Phe Lys Lys Asp Glu Ser Thr Asp Glu Ile
    370                 375                 380

Gly Leu Ile Gly Ile His Arg Phe Tyr Glu Ser Gly Ile Val Phe Glu
385                 390                 395                 400

Glu Tyr Lys Asp Tyr Phe Cys Ile Ser Lys Trp Tyr Leu Lys Glu Val
                405                 410                 415

Lys Arg Lys Pro Tyr Asn Leu Lys Leu Gly Cys Asn Trp Gln Phe Ile
                420                 425                 430

Pro Lys Asp Glu Gly Trp Thr Glu
            435                 440
```

<210> SEQ ID NO 9
<211> LENGTH: 1371
<212> TYPE: DNA
<213> ORGANISM: Artificial Sequence
<220> FEATURE:
<223> OTHER INFORMATION: Synthetic construct based on Clostridium botulinum sequence
<221> NAME/KEY: CDS
<222> LOCATION: (10)...(1359)

<400> SEQUENCE: 9

```
gaattcacg atg acc atc cca ttc aac atc ttc tcc tac acc aac aac tcc      51
          Met Thr Ile Pro Phe Asn Ile Phe Ser Tyr Thr Asn Asn Ser
           1               5                   10 ctg ttg aag gac atc atc aac gag tac ttc aac aac atc aac gac tcc        99
Leu Leu Lys Asp Ile Ile Asn Glu Tyr Phe Asn Asn Ile Asn Asp Ser
 15                  20                  25                  30 aag atc ctg tcc ctg cag aac cgt aag aac acc ttg gtc gac acc tcc       147
Lys Ile Leu Ser Leu Gln Asn Arg Lys Asn Thr Leu Val Asp Thr Ser
                 35                  40                  45 ggt tac aac gcc gag gtc tcc gag gag ggt gac gtc cag ctg aac cca       195
Gly Tyr Asn Ala Glu Val Ser Glu Glu Gly Asp Val Gln Leu Asn Pro
             50                  55                  60 atc ttc cca ttc gac ttc aag ctg ggt tcc tcc ggt gag gac aga ggt       243
Ile Phe Pro Phe Asp Phe Lys Leu Gly Ser Ser Gly Glu Asp Arg Gly
         65                  70                  75 aag gtc atc gtc acc cag aac gag aac atc gtc tac aac tcc atg tac       291
Lys Val Ile Val Thr Gln Asn Glu Asn Ile Val Tyr Asn Ser Met Tyr
     80                  85                  90 gag tcc ttc tcc atc tcc ttc tgg atc aga atc aac aag tgg gtc tcc       339
Glu Ser Phe Ser Ile Ser Phe Trp Ile Arg Ile Asn Lys Trp Val Ser
 95                 100                 105                 110 aac ttg cca ggt tac acc atc atc gac tcc gtc aag aac aac tcc ggt       387
Asn Leu Pro Gly Tyr Thr Ile Ile Asp Ser Val Lys Asn Asn Ser Gly
                115                 120                 125 tgg tcc atc ggt atc atc tcc aac ttc ctg gtc ttc acc ctg aag cag       435
Trp Ser Ile Gly Ile Ile Ser Asn Phe Leu Val Phe Thr Leu Lys Gln
            130                 135                 140 aac gag gac tcc gag cag tcc atc aac ttc tcc tac gac atc tcc aac       483
Asn Glu Asp Ser Glu Gln Ser Ile Asn Phe Ser Tyr Asp Ile Ser Asn
        145                 150                 155 aac gct cct ggt tac aac aag tgg ttc ttc gtc acc gtc acc aac aac       531
Asn Ala Pro Gly Tyr Asn Lys Trp Phe Phe Val Thr Val Thr Asn Asn
    160                 165                 170 atg atg ggt aac atg aag atc tac atc aac ggt aag ctg atc gac acc       579
```

-continued

| | | |
|---|---|---|
| Met Met Gly Asn Met Lys Ile Tyr Ile Asn Gly Lys Leu Ile Asp Thr<br>175                   180                   185                   190 | | |
| atc aag gtc aag gag ttg acc ggt atc aac ttc tcc aag acc atc acc<br>Ile Lys Val Lys Glu Leu Thr Gly Ile Asn Phe Ser Lys Thr Ile Thr<br>                    195                   200                 205 | 627 | |
| ttc gag atc aac aag atc cca gac acc ggt ctg atc acc tcc gac tcc<br>Phe Glu Ile Asn Lys Ile Pro Asp Thr Gly Leu Ile Thr Ser Asp Ser<br>             210                   215                220 | 675 | |
| gac aac atc aac atg tgg atc cgt gac ttc tac atc ttc gcc aag gag<br>Asp Asn Ile Asn Met Trp Ile Arg Asp Phe Tyr Ile Phe Ala Lys Glu<br>225                   230                   235 | 723 | |
| ttg gac ggt aag gac atc aac atc ctg ttc aac tcc ttg cag tac acc<br>Leu Asp Gly Lys Asp Ile Asn Ile Leu Phe Asn Ser Leu Gln Tyr Thr<br>240                   245                 250 | 771 | |
| aac gtc gtc aag gac tac tgg ggt aac gac ctg aga tac aac aag gag<br>Asn Val Val Lys Asp Tyr Trp Gly Asn Asp Leu Arg Tyr Asn Lys Glu<br>255                   260                 265                 270 | 819 | |
| tac tac atg gtc aac atc gac tac ttg aac aga tac atg tac gcc aac<br>Tyr Tyr Met Val Asn Ile Asp Tyr Leu Asn Arg Tyr Met Tyr Ala Asn<br>                   275                 280                285 | 867 | |
| tcc aga cag atc gtc ttc aac acc aga cgt aac aac aac gac ttc aac<br>Ser Arg Gln Ile Val Phe Asn Thr Arg Arg Asn Asn Asn Asp Phe Asn<br>             290                   295                300 | 915 | |
| gag ggt tac aag atc atc atc aag cgt atc aga ggt aac acc aac gac<br>Glu Gly Tyr Lys Ile Ile Ile Lys Arg Ile Arg Gly Asn Thr Asn Asp<br>                   305                 310                315 | 963 | |
| acc aga gtc aga ggt ggt gac atc ctg tac ttc gac atg act atc aac<br>Thr Arg Val Arg Gly Gly Asp Ile Leu Tyr Phe Asp Met Thr Ile Asn<br>320                   325                   330 | 1011 | |
| aac aag gcc tac aac ctg ttc atg aag aac gag acc atg tac gcc gac<br>Asn Lys Ala Tyr Asn Leu Phe Met Lys Asn Glu Thr Met Tyr Ala Asp<br>335                   340                 345                350 | 1059 | |
| aac cac tcc acc gag gac atc tac gcc atc ggt ctg cgt gag cag acc<br>Asn His Ser Thr Glu Asp Ile Tyr Ala Ile Gly Leu Arg Glu Gln Thr<br>                   355                 360                365 | 1107 | |
| aag gac atc aac gac aac atc atc ttc cag atc cag cca atg aac aac<br>Lys Asp Ile Asn Asp Asn Ile Ile Phe Gln Ile Gln Pro Met Asn Asn<br>             370                   375                380 | 1155 | |
| act tac tac tac gct tcc cag atc ttc aag tcc aac ttc aac ggt gag<br>Thr Tyr Tyr Tyr Ala Ser Gln Ile Phe Lys Ser Asn Phe Asn Gly Glu<br>385                   390                 395 | 1203 | |
| aac atc tcc ggt atc tgt tcc atc ggt acc tac aga ttc cgt ctg ggt<br>Asn Ile Ser Gly Ile Cys Ser Ile Gly Thr Tyr Arg Phe Arg Leu Gly<br>400                   405                 410 | 1251 | |
| ggt gac tgg tac aga cac aac tac ttg gtt cca act gtc aag cag ggt<br>Gly Asp Trp Tyr Arg His Asn Tyr Leu Val Pro Thr Val Lys Gln Gly<br>415                   420                 425                430 | 1299 | |
| aac tac gcc tcc ttg ctg gag tcc act tcc acc cac tgg gga ttc gtc<br>Asn Tyr Ala Ser Leu Leu Glu Ser Thr Ser Thr His Trp Gly Phe Val<br>                   435                 440                445 | 1347 | |
| cca gtc tcc gag taataggaat tc<br>Pro Val Ser Glu<br>             450 | 1371 | |

<210> SEQ ID NO 10
<211> LENGTH: 450
<212> TYPE: PRT
<213> ORGANISM: Artificial Sequence
<220> FEATURE:
<223> OTHER INFORMATION: Synthetic construct based on Clostridium
    botulinum sequence -continued

```
<400> SEQUENCE: 10

Met Thr Ile Pro Phe Asn Ile Phe Ser Tyr Thr Asn Asn Ser Leu Leu
1               5                   10                  15

Lys Asp Ile Ile Asn Glu Tyr Phe Asn Asn Ile Asn Asp Ser Lys Ile
            20                  25                  30

Leu Ser Leu Gln Asn Arg Lys Asn Thr Leu Val Asp Thr Ser Gly Tyr
        35                  40                  45

Asn Ala Glu Val Ser Glu Gly Asp Val Gln Leu Asn Pro Ile Phe
    50                  55                  60

Pro Phe Asp Phe Lys Leu Gly Ser Ser Gly Glu Asp Arg Gly Lys Val
65                  70                  75                  80

Ile Val Thr Gln Asn Glu Asn Ile Val Tyr Asn Ser Met Tyr Glu Ser
                85                  90                  95

Phe Ser Ile Ser Phe Trp Ile Arg Ile Asn Lys Trp Val Ser Asn Leu
            100                 105                 110

Pro Gly Tyr Thr Ile Ile Asp Ser Val Lys Asn Asn Ser Gly Trp Ser
        115                 120                 125

Ile Gly Ile Ile Ser Asn Phe Leu Val Phe Thr Leu Lys Gln Asn Glu
130                 135                 140

Asp Ser Glu Gln Ser Ile Asn Phe Ser Tyr Asp Ile Ser Asn Asn Ala
145                 150                 155                 160

Pro Gly Tyr Asn Lys Trp Phe Phe Val Thr Val Thr Asn Asn Met Met
                165                 170                 175

Gly Asn Met Lys Ile Tyr Ile Asn Gly Lys Leu Ile Asp Thr Ile Lys
            180                 185                 190

Val Lys Glu Leu Thr Gly Ile Asn Phe Ser Lys Thr Ile Thr Phe Glu
        195                 200                 205

Ile Asn Lys Ile Pro Asp Thr Gly Leu Ile Thr Ser Asp Ser Asp Asn
    210                 215                 220

Ile Asn Met Trp Ile Arg Asp Phe Tyr Ile Phe Ala Lys Glu Leu Asp
225                 230                 235                 240

Gly Lys Asp Ile Asn Ile Leu Phe Asn Ser Leu Gln Tyr Thr Asn Val
                245                 250                 255

Val Lys Asp Tyr Trp Gly Asn Asp Leu Arg Tyr Asn Lys Glu Tyr Tyr
            260                 265                 270

Met Val Asn Ile Asp Tyr Leu Asn Arg Tyr Met Tyr Ala Asn Ser Arg
        275                 280                 285

Gln Ile Val Phe Asn Thr Arg Arg Asn Asn Asn Asp Phe Asn Glu Gly
    290                 295                 300

Tyr Lys Ile Ile Ile Lys Arg Ile Arg Gly Asn Thr Asn Asp Thr Arg
305                 310                 315                 320

Val Arg Gly Gly Asp Ile Leu Tyr Phe Asp Met Thr Ile Asn Asn Lys
                325                 330                 335

Ala Tyr Asn Leu Phe Met Lys Asn Glu Thr Met Tyr Ala Asp Asn His
            340                 345                 350

Ser Thr Glu Asp Ile Tyr Ala Ile Gly Leu Arg Glu Gln Thr Lys Asp
        355                 360                 365

Ile Asn Asp Asn Ile Ile Phe Gln Ile Gln Pro Met Asn Asn Thr Tyr
    370                 375                 380

Tyr Tyr Ala Ser Gln Ile Phe Lys Ser Asn Phe Asn Gly Glu Asn Ile
385                 390                 395                 400

Ser Gly Ile Cys Ser Ile Gly Thr Tyr Arg Phe Arg Leu Gly Gly Asp
```

```
                      405                 410                 415
Trp Tyr Arg His Asn Tyr Leu Val Pro Thr Val Lys Gln Gly Asn Tyr
            420                 425                 430

Ala Ser Leu Leu Glu Ser Thr Ser Thr His Trp Gly Phe Val Pro Val
        435                 440                 445

Ser Glu
    450

<210> SEQ ID NO 11
<211> LENGTH: 1374
<212> TYPE: DNA
<213> ORGANISM: Artificial Sequence
<220> FEATURE:
<223> OTHER INFORMATION: Synthetic construct based on Clostridium
      botulinum sequence
<221> NAME/KEY: CDS
<222> LOCATION: (10)...(1362)

<400> SEQUENCE: 11 gaattcacg atg cgt ttg aag gct aag gtc aac gag tcc ttc gag aac acc       51
          Met Arg Leu Lys Ala Lys Val Asn Glu Ser Phe Glu Asn Thr
            1               5                  10 atg cca ttc aac atc ttc tcc tac acc aac aac tcc ttg ttg aag gac        99
Met Pro Phe Asn Ile Phe Ser Tyr Thr Asn Asn Ser Leu Leu Lys Asp
 15                  20                  25                  30 atc atc aac gag tac ttc aac tcc atc aac gac tcc aag atc ttg tcc       147
Ile Ile Asn Glu Tyr Phe Asn Ser Ile Asn Asp Ser Lys Ile Leu Ser
                 35                  40                  45 ttg cag aac aag aag aac gcc ttg gtc gac acc tcc ggt tac aac gcc       195
Leu Gln Asn Lys Lys Asn Ala Leu Val Asp Thr Ser Gly Tyr Asn Ala
             50                  55                  60 gag gtc aga gtc ggt gac aac gtc cag ttg aac acc atc tac acc aac       243
Glu Val Arg Val Gly Asp Asn Val Gln Leu Asn Thr Ile Tyr Thr Asn
         65                  70                  75 gac ttc aag ttg tcc tct tcc ggt gac aag atc atc gtc aac ttg aac       291
Asp Phe Lys Leu Ser Ser Ser Gly Asp Lys Ile Ile Val Asn Leu Asn
     80                  85                  90 aac aac atc ttg tac tcc gcc atc tac gag aac tcc tct gtc tcc ttc       339
Asn Asn Ile Leu Tyr Ser Ala Ile Tyr Glu Asn Ser Ser Val Ser Phe
 95                 100                 105                 110 tgg atc aag atc tcc aag gac ttg acc aac tcc cac aac gag tac acc       387
Trp Ile Lys Ile Ser Lys Asp Leu Thr Asn Ser His Asn Glu Tyr Thr
                115                 120                 125 atc atc aac tcc atc gag cag aac tcc ggt tgg aag ttg tgt atc cgt       435
Ile Ile Asn Ser Ile Glu Gln Asn Ser Gly Trp Lys Leu Cys Ile Arg
            130                 135                 140 aac ggt aac atc gag tgg atc ttg cag gac gtc aac cgt aag tac aag       483
Asn Gly Asn Ile Glu Trp Ile Leu Gln Asp Val Asn Arg Lys Tyr Lys
        145                 150                 155 tcc ttg atc ttc gac tac tcc gag tcc ttg tcc cac acc ggt tac acc       531
Ser Leu Ile Phe Asp Tyr Ser Glu Ser Leu Ser His Thr Gly Tyr Thr
    160                 165                 170 aac aag tgg ttc ttc gtc acc atc acc aac aac atc atg ggt tac atg       579
Asn Lys Trp Phe Phe Val Thr Ile Thr Asn Asn Ile Met Gly Tyr Met
175                 180                 185                 190 aag ttg tac atc aac ggt gag ttg aag cag tcc cag aag atc gag gac       627
Lys Leu Tyr Ile Asn Gly Glu Leu Lys Gln Ser Gln Lys Ile Glu Asp
                195                 200                 205 ctg gac gag gtc aag ctg gac aag acc atc gtc ttc ggt atc gac gag       675
Leu Asp Glu Val Lys Leu Asp Lys Thr Ile Val Phe Gly Ile Asp Glu
            210                 215                 220
```

```
aac atc gac gag aac cag atg ttg tgg att cgt gac ttc aac atc ttc      723
Asn Ile Asp Glu Asn Gln Met Leu Trp Ile Arg Asp Phe Asn Ile Phe
            225                 230                 235 tcc aag gag ctg tcc aac gag gac atc aac atc gtc tac gag ggt cag      771
Ser Lys Glu Leu Ser Asn Glu Asp Ile Asn Ile Val Tyr Glu Gly Gln
        240                 245                 250 atc ctg agg aac gtc atc aag gac tac tgg ggt aac cca ctg aag ttc      819
Ile Leu Arg Asn Val Ile Lys Asp Tyr Trp Gly Asn Pro Leu Lys Phe
255                 260                 265                 270 gac acc gag tac tac atc atc aac gac aac tac atc gac cgt tac atc      867
Asp Thr Glu Tyr Tyr Ile Ile Asn Asp Asn Tyr Ile Asp Arg Tyr Ile
                275                 280                 285 gcc cca gag tcc aac gtc ctg gtc ctg gtc cag tac cct gac ctg tcc      915
Ala Pro Glu Ser Asn Val Leu Val Leu Val Gln Tyr Pro Asp Leu Ser
            290                 295                 300 aag ctg tac acc ggt aac cct atc acc atc aag tcc gtc tcc gac aag      963
Lys Leu Tyr Thr Gly Asn Pro Ile Thr Ile Lys Ser Val Ser Asp Lys
        305                 310                 315 aac cct tac tcc cgt atc ctg aac ggt gac aac atc atc ctg cac atg     1011
Asn Pro Tyr Ser Arg Ile Leu Asn Gly Asp Asn Ile Ile Leu His Met
320                 325                 330 ctg tac aac tcc cgt aag tac atg atc atc cgt gac acc gac acc atc     1059
Leu Tyr Asn Ser Arg Lys Tyr Met Ile Ile Arg Asp Thr Asp Thr Ile
335                 340                 345                 350 tac gcc acc cag ggt ggt gag tgt tcc cag aac tgt gtc tac gcc ctg     1107
Tyr Ala Thr Gln Gly Gly Glu Cys Ser Gln Asn Cys Val Tyr Ala Leu
                355                 360                 365 aag ctg cag tcc aac ctg ggt aac tac ggt atc ggt atc ttc tcc atc     1155
Lys Leu Gln Ser Asn Leu Gly Asn Tyr Gly Ile Gly Ile Phe Ser Ile
            370                 375                 380 aag aac atc gtc tcc aag aac aag tac tgc tcc cag atc ttc tcc tcc     1203
Lys Asn Ile Val Ser Lys Asn Lys Tyr Cys Ser Gln Ile Phe Ser Ser
        385                 390                 395 ttc cgt gag aac acc atg ctg ctg gcc gac atc tac aag cct tgg cgt     1251
Phe Arg Glu Asn Thr Met Leu Leu Ala Asp Ile Tyr Lys Pro Trp Arg
400                 405                 410 ttc tcc ttc aag aac gcc tac act cct gtc gcc gtc acc aac tac gag     1299
Phe Ser Phe Lys Asn Ala Tyr Thr Pro Val Ala Val Thr Asn Tyr Glu
415                 420                 425                 430 acc aag ctg ctg tcc acc tcc tcc ttc tgg aag ttc atc tcc cgt gac     1347
Thr Lys Leu Leu Ser Thr Ser Ser Phe Trp Lys Phe Ile Ser Arg Asp
                435                 440                 445 cca ggt tgg gtc gag taataggaat tc                                   1374
Pro Gly Trp Val Glu
            450
```

<210> SEQ ID NO 12
<211> LENGTH: 451
<212> TYPE: PRT
<213> ORGANISM: Artificial Sequence
<220> FEATURE:
<223> OTHER INFORMATION: Synthetic Construct

<400> SEQUENCE: 12

```
Met Arg Leu Lys Ala Lys Val Asn Glu Ser Phe Glu Asn Thr Met Pro
1               5                   10                  15

Phe Asn Ile Phe Ser Tyr Thr Asn Asn Ser Leu Leu Lys Asp Ile Ile
            20                  25                  30

Asn Glu Tyr Phe Asn Ser Ile Asn Asp Ser Lys Ile Leu Ser Leu Gln
        35                  40                  45
```

```
Asn Lys Lys Asn Ala Leu Val Asp Thr Ser Gly Tyr Asn Ala Glu Val
 50                  55                  60

Arg Val Gly Asp Asn Val Gln Leu Asn Thr Ile Tyr Thr Asn Asp Phe
 65                  70                  75                  80

Lys Leu Ser Ser Gly Asp Lys Ile Ile Val Asn Leu Asn Asn Asn
                 85                  90                  95

Ile Leu Tyr Ser Ala Ile Tyr Glu Asn Ser Ser Val Ser Phe Trp Ile
             100                 105                 110

Lys Ile Ser Lys Asp Leu Thr Asn Ser His Asn Glu Tyr Thr Ile Ile
         115                 120                 125

Asn Ser Ile Glu Gln Asn Ser Gly Trp Lys Leu Cys Ile Arg Asn Gly
     130                 135                 140

Asn Ile Glu Trp Ile Leu Gln Asp Val Asn Arg Lys Tyr Lys Ser Leu
145                 150                 155                 160

Ile Phe Asp Tyr Ser Glu Ser Leu Ser His Thr Gly Tyr Thr Asn Lys
                 165                 170                 175

Trp Phe Phe Val Thr Ile Thr Asn Asn Ile Met Gly Tyr Met Lys Leu
             180                 185                 190

Tyr Ile Asn Gly Glu Leu Lys Gln Ser Gln Lys Ile Glu Asp Leu Asp
         195                 200                 205

Glu Val Lys Leu Asp Lys Thr Ile Val Phe Gly Ile Asp Glu Asn Ile
    210                 215                 220

Asp Glu Asn Gln Met Leu Trp Ile Arg Asp Phe Asn Ile Phe Ser Lys
225                 230                 235                 240

Glu Leu Ser Asn Glu Asp Ile Asn Ile Val Tyr Glu Gly Gln Ile Leu
                245                 250                 255

Arg Asn Val Ile Lys Asp Tyr Trp Gly Asn Pro Leu Lys Phe Asp Thr
            260                 265                 270

Glu Tyr Tyr Ile Ile Asn Asp Asn Tyr Ile Asp Arg Tyr Ile Ala Pro
        275                 280                 285

Glu Ser Asn Val Leu Val Leu Val Gln Tyr Pro Asp Leu Ser Lys Leu
    290                 295                 300

Tyr Thr Gly Asn Pro Ile Thr Ile Lys Ser Val Ser Asp Lys Asn Pro
305                 310                 315                 320

Tyr Ser Arg Ile Leu Asn Gly Asp Asn Ile Ile Leu His Met Leu Tyr
                325                 330                 335

Asn Ser Arg Lys Tyr Met Ile Ile Arg Asp Thr Asp Thr Ile Tyr Ala
            340                 345                 350

Thr Gln Gly Gly Glu Cys Ser Gln Asn Cys Val Tyr Ala Leu Lys Leu
        355                 360                 365

Gln Ser Asn Leu Gly Asn Tyr Gly Ile Gly Ile Phe Ser Ile Lys Asn
    370                 375                 380

Ile Val Ser Lys Asn Lys Tyr Cys Ser Gln Ile Phe Ser Ser Phe Arg
385                 390                 395                 400

Glu Asn Thr Met Leu Leu Ala Asp Ile Tyr Lys Pro Trp Arg Phe Ser
                405                 410                 415

Phe Lys Asn Ala Tyr Thr Pro Val Ala Val Thr Asn Tyr Glu Thr Lys
            420                 425                 430

Leu Leu Ser Thr Ser Ser Phe Trp Lys Phe Ile Ser Arg Asp Pro Gly
        435                 440                 445

Trp Val Glu
450
```

-continued

```
<210> SEQ ID NO 13
<211> LENGTH: 1400
<212> TYPE: DNA
<213> ORGANISM: Artificial Sequence
<220> FEATURE:
<223> OTHER INFORMATION: Synthetic construct based on Clostridium
      botulinum sequence
<221> NAME/KEY: CDS
<222> LOCATION: (10)...(1356)

<400> SEQUENCE: 13 gaattcacc atg gga gag agt cag caa gaa cta aat tct atg gta act gat      51
          Met Gly Glu Ser Gln Gln Glu Leu Asn Ser Met Val Thr Asp
            1               5                  10 acc cta aat aat agt att cct ttt aag ctt tct tct tat aca gat gat        99
Thr Leu Asn Asn Ser Ile Pro Phe Lys Leu Ser Ser Tyr Thr Asp Asp
 15                  20                  25                  30 aaa att tta att tcc tac ttc aac aag ttc ttc aag aga att aag tct       147
Lys Ile Leu Ile Ser Tyr Phe Asn Lys Phe Phe Lys Arg Ile Lys Ser
                 35                  40                  45 tct tcc gtt tta aac atg aga tac aag aat gat aaa tac gtc gac act       195
Ser Ser Val Leu Asn Met Arg Tyr Lys Asn Asp Lys Tyr Val Asp Thr
             50                  55                  60 tcc ggt tac gac tcc aat atc aac att aac ggt gac gtg tac aag tac       243
Ser Gly Tyr Asp Ser Asn Ile Asn Ile Asn Gly Asp Val Tyr Lys Tyr
         65                  70                  75 cca act aac aaa aac caa ttc ggt atc tac aac gac aag ctt tcc gag       291
Pro Thr Asn Lys Asn Gln Phe Gly Ile Tyr Asn Asp Lys Leu Ser Glu
     80                  85                  90 gtc aac atc tct caa aac gac tac att atc tac gac aac aag tac aag       339
Val Asn Ile Ser Gln Asn Asp Tyr Ile Ile Tyr Asp Asn Lys Tyr Lys
 95                 100                 105                 110 aac ttc tct att tct ttc tgg gtc agg att cct aac tac gac aac aag       387
Asn Phe Ser Ile Ser Phe Trp Val Arg Ile Pro Asn Tyr Asp Asn Lys
                115                 120                 125 atc gtc aac gtt aac aac gag tac act atc atc aac tgt atg aga gac       435
Ile Val Asn Val Asn Asn Glu Tyr Thr Ile Ile Asn Cys Met Arg Asp
            130                 135                 140 aac aac tcc ggt tgg aag gtc tct ctt aac cac aac gag atc att tgg       483
Asn Asn Ser Gly Trp Lys Val Ser Leu Asn His Asn Glu Ile Ile Trp
        145                 150                 155 acc ttg caa gac aac gca ggt att aac caa aag tta gca ttc aac tac       531
Thr Leu Gln Asp Asn Ala Gly Ile Asn Gln Lys Leu Ala Phe Asn Tyr
    160                 165                 170 ggt aac gca aac ggt att tct gac tac atc aac aag tgg att ttc gtc       579
Gly Asn Ala Asn Gly Ile Ser Asp Tyr Ile Asn Lys Trp Ile Phe Val
175                 180                 185                 190 act atc act aac gac aga tta ggt gac tct aag ctt tac att aac ggt       627
Thr Ile Thr Asn Asp Arg Leu Gly Asp Ser Lys Leu Tyr Ile Asn Gly
                195                 200                 205 aac tta atc gac caa aag tcc att tta aac tta ggt aac att cac gtt       675
Asn Leu Ile Asp Gln Lys Ser Ile Leu Asn Leu Gly Asn Ile His Val
            210                 215                 220 tct gac aac atc tta ttc aag atc gtt aac tgc agt tac acc aga tac       723
Ser Asp Asn Ile Leu Phe Lys Ile Val Asn Cys Ser Tyr Thr Arg Tyr
        225                 230                 235 att ggc att aga tac ttc aac att ttc gac aag gag tta gac gag acc       771
Ile Gly Ile Arg Tyr Phe Asn Ile Phe Asp Lys Glu Leu Asp Glu Thr
    240                 245                 250 gag att caa act tta tac agc aac gaa cct aac acc aat att ttg aag       819
Glu Ile Gln Thr Leu Tyr Ser Asn Glu Pro Asn Thr Asn Ile Leu Lys
```

```
                255                 260                 265                 270
gac ttc tgg ggt aac tac ttg ctt tac gac aag gaa tac tac tta tta        867
Asp Phe Trp Gly Asn Tyr Leu Leu Tyr Asp Lys Glu Tyr Tyr Leu Leu
                    275                 280                 285 aac gtg tta aag cca aac aac ttc att gat agg aga aag gat tct act        915
Asn Val Leu Lys Pro Asn Asn Phe Ile Asp Arg Arg Lys Asp Ser Thr
            290                 295                 300 tta agc att aac aac atc aga agc act att ctt tta gct aac aga tta        963
Leu Ser Ile Asn Asn Ile Arg Ser Thr Ile Leu Leu Ala Asn Arg Leu
        305                 310                 315 tac tct ggt atc aag gtt aag atc caa aga gtt aac aac tct tct act       1011
Tyr Ser Gly Ile Lys Val Lys Ile Gln Arg Val Asn Asn Ser Ser Thr
    320                 325                 330 aac gat aac ctt gtt aga aag aac gat cag gtc tat att aac ttc gtc       1059
Asn Asp Asn Leu Val Arg Lys Asn Asp Gln Val Tyr Ile Asn Phe Val
335                 340                 345                 350 gct agc aag act cac tta ttc cca tta tat gct gat acc gct acc acc       1107
Ala Ser Lys Thr His Leu Phe Pro Leu Tyr Ala Asp Thr Ala Thr Thr
                    355                 360                 365 aac aag gag aag acc atc aag atc tcc tcc tct ggc aac aga ttt aac       1155
Asn Lys Glu Lys Thr Ile Lys Ile Ser Ser Ser Gly Asn Arg Phe Asn
            370                 375                 380 caa gtc gtc gtt atg aac tcc gtc ggt aac aac tgt acc atg aac ttt       1203
Gln Val Val Val Met Asn Ser Val Gly Asn Asn Cys Thr Met Asn Phe
        385                 390                 395 aaa aat aat aat gga aat aat att ggg ttg tta ggt ttc aag gca gat       1251
Lys Asn Asn Asn Gly Asn Asn Ile Gly Leu Leu Gly Phe Lys Ala Asp
    400                 405                 410 act gta gtt gct agt act tgg tat tat acc cac atg aga gat cac acc       1299
Thr Val Val Ala Ser Thr Trp Tyr Tyr Thr His Met Arg Asp His Thr
415                 420                 425                 430 aac agc aat gga tgt ttt tgg aac ttt att tct gaa gaa cat gga tgg       1347
Asn Ser Asn Gly Cys Phe Trp Asn Phe Ile Ser Glu Glu His Gly Trp
                    435                 440                 445 caa gaa aaa taatagggat ccgcggccgc acgcgtcccg ggactagtga              1396
Gln Glu Lys attc                                                                   1400

<210> SEQ ID NO 14
<211> LENGTH: 449
<212> TYPE: PRT
<213> ORGANISM: Artificial Sequence
<220> FEATURE:
<223> OTHER INFORMATION: Synthetic Construct

<400> SEQUENCE: 14

Met Gly Glu Ser Gln Gln Glu Leu Asn Ser Met Val Thr Asp Thr Leu
 1               5                  10                  15

Asn Asn Ser Ile Pro Phe Lys Leu Ser Ser Tyr Thr Asp Asp Lys Ile
                20                  25                  30

Leu Ile Ser Tyr Phe Asn Lys Phe Phe Lys Arg Ile Lys Ser Ser Ser
            35                  40                  45

Val Leu Asn Met Arg Tyr Lys Asn Asp Lys Tyr Val Asp Thr Ser Gly
        50                  55                  60

Tyr Asp Ser Asn Ile Asn Ile Asn Gly Asp Val Tyr Lys Tyr Pro Thr
65                  70                  75                  80

Asn Lys Asn Gln Phe Gly Ile Tyr Asn Asp Lys Leu Ser Glu Val Asn
                85                  90                  95
```

Ile Ser Gln Asn Asp Tyr Ile Ile Tyr Asp Asn Lys Tyr Lys Asn Phe
             100                 105                 110

Ser Ile Ser Phe Trp Val Arg Ile Pro Asn Tyr Asp Asn Lys Ile Val
         115                 120                 125

Asn Val Asn Asn Glu Tyr Thr Ile Ile Asn Cys Met Arg Asp Asn Asn
     130                 135                 140

Ser Gly Trp Lys Val Ser Leu Asn His Asn Glu Ile Ile Trp Thr Leu
145                 150                 155                 160

Gln Asp Asn Ala Gly Ile Asn Gln Lys Leu Ala Phe Asn Tyr Gly Asn
                 165                 170                 175

Ala Asn Gly Ile Ser Asp Tyr Ile Asn Lys Trp Ile Phe Val Thr Ile
             180                 185                 190

Thr Asn Asp Arg Leu Gly Asp Ser Lys Leu Tyr Ile Asn Gly Asn Leu
         195                 200                 205

Ile Asp Gln Lys Ser Ile Leu Asn Leu Gly Asn Ile His Val Ser Asp
     210                 215                 220

Asn Ile Leu Phe Lys Ile Val Asn Cys Ser Tyr Thr Arg Tyr Ile Gly
225                 230                 235                 240

Ile Arg Tyr Phe Asn Ile Phe Asp Lys Glu Leu Asp Glu Thr Glu Ile
                 245                 250                 255

Gln Thr Leu Tyr Ser Asn Glu Pro Asn Thr Asn Ile Leu Lys Asp Phe
             260                 265                 270

Trp Gly Asn Tyr Leu Leu Tyr Asp Lys Glu Tyr Tyr Leu Leu Asn Val
         275                 280                 285

Leu Lys Pro Asn Asn Phe Ile Asp Arg Arg Lys Asp Ser Thr Leu Ser
     290                 295                 300

Ile Asn Asn Ile Arg Ser Thr Ile Leu Leu Ala Asn Arg Leu Tyr Ser
305                 310                 315                 320

Gly Ile Lys Val Lys Ile Gln Arg Val Asn Asn Ser Ser Thr Asn Asp
                 325                 330                 335

Asn Leu Val Arg Lys Asn Asp Gln Val Tyr Ile Asn Phe Val Ala Ser
             340                 345                 350

Lys Thr His Leu Phe Pro Leu Tyr Ala Asp Thr Ala Thr Thr Asn Lys
         355                 360                 365

Glu Lys Thr Ile Lys Ile Ser Ser Ser Gly Asn Arg Phe Asn Gln Val
     370                 375                 380

Val Val Met Asn Ser Val Gly Asn Asn Cys Thr Met Asn Phe Lys Asn
385                 390                 395                 400

Asn Asn Gly Asn Asn Ile Gly Leu Leu Gly Phe Lys Ala Asp Thr Val
                 405                 410                 415

Val Ala Ser Thr Trp Tyr Tyr Thr His Met Arg Asp His Thr Asn Ser
             420                 425                 430

Asn Gly Cys Phe Trp Asn Phe Ile Ser Glu Glu His Gly Trp Gln Glu
         435                 440                 445

Lys

<210> SEQ ID NO 15
<211> LENGTH: 1317
<212> TYPE: DNA
<213> ORGANISM: Artificial Sequence
<220> FEATURE:
<223> OTHER INFORMATION: Synthetic Construct
<221> NAME/KEY: CDS
<222> LOCATION: (10)...(1305)

<400> SEQUENCE: 15

-continued

```
gaattcacg atg tcc tac acc aac gac aag atc ctg atc ttg tac ttc aac        51
          Met Ser Tyr Thr Asn Asp Lys Ile Leu Ile Leu Tyr Phe Asn
          1               5                   10 aag ctg tac aag aag atc aag gac aac tcc atc ttg gac atg aga tac          99
Lys Leu Tyr Lys Lys Ile Lys Asp Asn Ser Ile Leu Asp Met Arg Tyr
15                  20                  25                  30 gaa aac aat aag ttc atc gac atc tcc ggt tac ggt tcc aac atc tcc         147
Glu Asn Asn Lys Phe Ile Asp Ile Ser Gly Tyr Gly Ser Asn Ile Ser
                35                  40                  45 atc aac ggt gac gtc tac atc tac tcc acc aat aga aac cag ttc gga         195
Ile Asn Gly Asp Val Tyr Ile Tyr Ser Thr Asn Arg Asn Gln Phe Gly
            50                  55                  60 atc tac tcc tcc aag cct tcc gag gtc aac atc gct cag aac aac gac         243
Ile Tyr Ser Ser Lys Pro Ser Glu Val Asn Ile Ala Gln Asn Asn Asp
        65                  70                  75 atc atc tac aac gga aga tac cag aac ttc tcc atc tcc ttc tgg gtc         291
Ile Ile Tyr Asn Gly Arg Tyr Gln Asn Phe Ser Ile Ser Phe Trp Val
    80                  85                  90 cgt atc cca aag tac ttc aac aag gtc aac ctg aat aac gag tac acc         339
Arg Ile Pro Lys Tyr Phe Asn Lys Val Asn Leu Asn Asn Glu Tyr Thr
95                  100                 105                 110 atc atc gac tgc atc cgt aac aat aac tcc gga tgg aag atc tcc ctg         387
Ile Ile Asp Cys Ile Arg Asn Asn Asn Ser Gly Trp Lys Ile Ser Leu
                115                 120                 125 aac tac aac aag atc atc tgg acc ctg cag gac acc gcc ggt aac aat         435
Asn Tyr Asn Lys Ile Ile Trp Thr Leu Gln Asp Thr Ala Gly Asn Asn
            130                 135                 140 cag aag ttg gtc ttc aac tac acc cag atg atc tcc atc tcc gac tac         483
Gln Lys Leu Val Phe Asn Tyr Thr Gln Met Ile Ser Ile Ser Asp Tyr
        145                 150                 155 atc aac aag tgg atc ttc gtc acc atc acc aat aac cgt ttg gga aac         531
Ile Asn Lys Trp Ile Phe Val Thr Ile Thr Asn Asn Arg Leu Gly Asn
    160                 165                 170 tcc aga atc tac atc aac ggt aac ttg atc gac gag aag tcc atc tcc         579
Ser Arg Ile Tyr Ile Asn Gly Asn Leu Ile Asp Glu Lys Ser Ile Ser
175                 180                 185                 190 aac ttg ggt gac atc cac gtc tcc gac aac att ttg ttc aag atc gtc         627
Asn Leu Gly Asp Ile His Val Ser Asp Asn Ile Leu Phe Lys Ile Val
                195                 200                 205 ggt tgt aac gac acc cgt tac gtc ggg atc cgt tac ttc aaa gtc ttc         675
Gly Cys Asn Asp Thr Arg Tyr Val Gly Ile Arg Tyr Phe Lys Val Phe
            210                 215                 220 gac act gag ttg ggt aag acc gag atc gag acc ttg tac tcc gac gag         723
Asp Thr Glu Leu Gly Lys Thr Glu Ile Glu Thr Leu Tyr Ser Asp Glu
        225                 230                 235 cct gac cca tcc atc ctg aag gac ttc tgg ggt aac tac ctg ctg tac         771
Pro Asp Pro Ser Ile Leu Lys Asp Phe Trp Gly Asn Tyr Leu Leu Tyr
    240                 245                 250 aac aaa cgt tac tac ttg ctg aac ttg ttg cgt acc gac aag tcc atc         819
Asn Lys Arg Tyr Tyr Leu Leu Asn Leu Leu Arg Thr Asp Lys Ser Ile
255                 260                 265                 270 acc cag aac tcc aac ttc ttg aac atc aac cag cag aga ggt gtc tac         867
Thr Gln Asn Ser Asn Phe Leu Asn Ile Asn Gln Gln Arg Gly Val Tyr
                275                 280                 285 cag aag cca aac atc ttc tcc aac acc aga ttg tac acc gga gtc gag         915
Gln Lys Pro Asn Ile Phe Ser Asn Thr Arg Leu Tyr Thr Gly Val Glu
            290                 295                 300 gtc att atc aga aag aac gga tct act gat att tcc aac acc gat aac         963
Val Ile Ile Arg Lys Asn Gly Ser Thr Asp Ile Ser Asn Thr Asp Asn
```

-continued

```
                        305                 310                 315
ttc gtc aga aag aac gat ctg gct tac atc aac gtt gtc gac aga gat    1011
Phe Val Arg Lys Asn Asp Leu Ala Tyr Ile Asn Val Val Asp Arg Asp
        320                 325                 330 gtc gaa tac cgt ctg tac gcc gat atc tct atc gcc aaa cct gaa aag    1059
Val Glu Tyr Arg Leu Tyr Ala Asp Ile Ser Ile Ala Lys Pro Glu Lys
335                 340                 345                 350 atc atc aag ctg atc cgt acc tct aac tct aac aac tct ctg gga caa    1107
Ile Ile Lys Leu Ile Arg Thr Ser Asn Ser Asn Asn Ser Leu Gly Gln
                355                 360                 365 atc atc gtc atg gac tcc atc ggt aat aac tgt acc atg aac ttc cag    1155
Ile Ile Val Met Asp Ser Ile Gly Asn Asn Cys Thr Met Asn Phe Gln
            370                 375                 380 aac aac aac ggt gga aac atc ggt ttg ttg ggt ttc cac tcc aac aac    1203
Asn Asn Asn Gly Gly Asn Ile Gly Leu Leu Gly Phe His Ser Asn Asn
        385                 390                 395 ttg gtc gct tcc tcc tgg tac tac aac aac atc cgt aag aac acc tcc    1251
Leu Val Ala Ser Ser Trp Tyr Tyr Asn Asn Ile Arg Lys Asn Thr Ser
    400                 405                 410 tcc aac ggt tgc ttc tgg tcc ttc atc tcc aag gag cac ggt tgg cag    1299
Ser Asn Gly Cys Phe Trp Ser Phe Ile Ser Lys Glu His Gly Trp Gln
415                 420                 425                 430 gag aac taataggaat tc                                              1317
Glu Asn
```

<210> SEQ ID NO 16
<211> LENGTH: 432
<212> TYPE: PRT
<213> ORGANISM: Artificial Sequence
<220> FEATURE:
<223> OTHER INFORMATION: Synthetic Construct

<400> SEQUENCE: 16

```
Met Ser Tyr Thr Asn Asp Lys Ile Leu Ile Leu Tyr Phe Asn Lys Leu
  1               5                  10                  15

Tyr Lys Lys Ile Lys Asp Asn Ser Ile Leu Asp Met Arg Tyr Glu Asn
             20                  25                  30

Asn Lys Phe Ile Asp Ile Ser Gly Tyr Gly Ser Asn Ile Ser Ile Asn
         35                  40                  45

Gly Asp Val Tyr Ile Tyr Ser Thr Asn Arg Asn Gln Phe Gly Ile Tyr
     50                  55                  60

Ser Ser Lys Pro Ser Glu Val Asn Ile Ala Gln Asn Asn Asp Ile Ile
 65                  70                  75                  80

Tyr Asn Gly Arg Tyr Gln Asn Phe Ser Ile Ser Phe Trp Val Arg Ile
                 85                  90                  95

Pro Lys Tyr Phe Asn Lys Val Asn Leu Asn Asn Glu Tyr Thr Ile Ile
            100                 105                 110

Asp Cys Ile Arg Asn Asn Asn Ser Gly Trp Lys Ile Ser Leu Asn Tyr
        115                 120                 125

Asn Lys Ile Ile Trp Thr Leu Gln Asp Thr Ala Gly Asn Asn Gln Lys
    130                 135                 140

Leu Val Phe Asn Tyr Thr Gln Met Ile Ser Ile Ser Asp Tyr Ile Asn
145                 150                 155                 160

Lys Trp Ile Phe Val Thr Ile Thr Asn Asn Arg Leu Gly Asn Ser Arg
                165                 170                 175

Ile Tyr Ile Asn Gly Asn Leu Ile Asp Glu Lys Ser Ile Ser Asn Leu
            180                 185                 190
```

-continued

```
Gly Asp Ile His Val Ser Asp Asn Ile Leu Phe Lys Ile Val Gly Cys
        195                 200                 205

Asn Asp Thr Arg Tyr Val Gly Ile Arg Tyr Phe Lys Val Phe Asp Thr
    210                 215                 220

Glu Leu Gly Lys Thr Glu Ile Glu Thr Leu Tyr Ser Asp Glu Pro Asp
225                 230                 235                 240

Pro Ser Ile Leu Lys Asp Phe Trp Gly Asn Tyr Leu Leu Tyr Asn Lys
                245                 250                 255

Arg Tyr Tyr Leu Leu Asn Leu Leu Arg Thr Asp Lys Ser Ile Thr Gln
            260                 265                 270

Asn Ser Asn Phe Leu Asn Ile Asn Gln Gln Arg Gly Val Tyr Gln Lys
        275                 280                 285

Pro Asn Ile Phe Ser Asn Thr Arg Leu Tyr Thr Gly Val Glu Val Ile
    290                 295                 300

Ile Arg Lys Asn Gly Ser Thr Asp Ile Ser Asn Thr Asp Asn Phe Val
305                 310                 315                 320

Arg Lys Asn Asp Leu Ala Tyr Ile Asn Val Val Asp Arg Asp Val Glu
                325                 330                 335

Tyr Arg Leu Tyr Ala Asp Ile Ser Ile Ala Lys Pro Glu Lys Ile Ile
            340                 345                 350

Lys Leu Ile Arg Thr Ser Asn Ser Asn Ser Leu Gly Gln Ile Ile
        355                 360                 365

Val Met Asp Ser Ile Gly Asn Asn Cys Thr Met Asn Phe Gln Asn Asn
    370                 375                 380

Asn Gly Gly Asn Ile Gly Leu Leu Gly Phe His Ser Asn Asn Leu Val
385                 390                 395                 400

Ala Ser Ser Trp Tyr Tyr Asn Asn Ile Arg Lys Asn Thr Ser Ser Asn
                405                 410                 415

Gly Cys Phe Trp Ser Phe Ile Ser Lys Glu His Gly Trp Gln Glu Asn
            420                 425                 430
```

<210> SEQ ID NO 17
<211> LENGTH: 1368
<212> TYPE: DNA
<213> ORGANISM: Artificial Sequence
<220> FEATURE:
<223> OTHER INFORMATION: Synthetic Construct
<221> NAME/KEY: CDS
<222> LOCATION: (10)...(1356)

<400> SEQUENCE: 17

```
gaattcacg atg aag gac acc atc ctg atc cag gtc ttc aac aac tac atc      51
          Met Lys Asp Thr Ile Leu Ile Gln Val Phe Asn Asn Tyr Ile
            1               5                   10 tcc aac atc tcc tcc aac gcc atc ctg tcc ctg tcc tac cgt ggt ggt        99
Ser Asn Ile Ser Ser Asn Ala Ile Leu Ser Leu Ser Tyr Arg Gly Gly
 15                  20                  25                  30 cgt ctg atc gac tcc tcc ggt tac gga gcc acc atg aac gtc ggt tcc       147
Arg Leu Ile Asp Ser Ser Gly Tyr Gly Ala Thr Met Asn Val Gly Ser
                 35                  40                  45 gac gtc atc ttc aac gac atc ggt aac ggt cag ttc aag ctg aac aac       195
Asp Val Ile Phe Asn Asp Ile Gly Asn Gly Gln Phe Lys Leu Asn Asn
             50                  55                  60 tcc gag aac tcc aac atc acc gcc cac cag tcc aag ttc gtc gtc tac       243
Ser Glu Asn Ser Asn Ile Thr Ala His Gln Ser Lys Phe Val Val Tyr
         65                  70                  75 gac tcc atg ttc gac aac ttc tcc atc aac ttc tgg gtc cgt acc cca       291
Asp Ser Met Phe Asp Asn Phe Ser Ile Asn Phe Trp Val Arg Thr Pro
```

-continued

```
            80                  85                  90
aag tac aac aac aac gac atc cag acc tac ctg cag aac gag tac acc      339
Lys Tyr Asn Asn Asn Asp Ile Gln Thr Tyr Leu Gln Asn Glu Tyr Thr
 95                 100                 105                 110 atc atc tcc tgt atc aag aac gac tcc ggt tgg aag gtc tcc atc aag      387
Ile Ile Ser Cys Ile Lys Asn Asp Ser Gly Trp Lys Val Ser Ile Lys
                115                 120                 125 gga aac cgt atc atc tgg acc ctg atc gac gtc aac gcc aag tcc aag      435
Gly Asn Arg Ile Ile Trp Thr Leu Ile Asp Val Asn Ala Lys Ser Lys
            130                 135                 140 tcc atc ttc ttc gag tac tcc atc aag gac aac atc tcc gac tac atc      483
Ser Ile Phe Phe Glu Tyr Ser Ile Lys Asp Asn Ile Ser Asp Tyr Ile
            145                 150                 155 aac aag tgg ttc tcc atc acc atc acc aac gac cgt ctg ggt aac gcc      531
Asn Lys Trp Phe Ser Ile Thr Ile Thr Asn Asp Arg Leu Gly Asn Ala
            160                 165                 170 aac atc tac atc aac ggt tcc ctg aag aag tcc gag aag atc ctg aac      579
Asn Ile Tyr Ile Asn Gly Ser Leu Lys Lys Ser Glu Lys Ile Leu Asn
175                 180                 185                 190 ctg gac cgt atc aac tcc tcc aac gac atc gac ttc aag ctg atc aac      627
Leu Asp Arg Ile Asn Ser Ser Asn Asp Ile Asp Phe Lys Leu Ile Asn
                195                 200                 205 tgt acc gac acc acc aag ttc gtc tgg atc aag gac ttc aac atc ttc      675
Cys Thr Asp Thr Thr Lys Phe Val Trp Ile Lys Asp Phe Asn Ile Phe
            210                 215                 220 ggt cgt gag ctg aac gcc acc gag gtc tcc tcc ctg tac tgg atc cag      723
Gly Arg Glu Leu Asn Ala Thr Glu Val Ser Ser Leu Tyr Trp Ile Gln
            225                 230                 235 tcc tcc acc aac acc ctg aag gac ttc tgg gga aac cca ctg cgt tac      771
Ser Ser Thr Asn Thr Leu Lys Asp Phe Trp Gly Asn Pro Leu Arg Tyr
            240                 245                 250 gac acc cag tac tac ctg ttc aac cag ggt atg cag aac atc tac atc      819
Asp Thr Gln Tyr Tyr Leu Phe Asn Gln Gly Met Gln Asn Ile Tyr Ile
255                 260                 265                 270 aag tac ttc tcc aag gcc tcc atg ggt gag acc gcc cct cgt acc aac      867
Lys Tyr Phe Ser Lys Ala Ser Met Gly Glu Thr Ala Pro Arg Thr Asn
                275                 280                 285 ttc aac aac gcc gcc atc aac tac cag aac ctg tac ctg ggt ctg cgt      915
Phe Asn Asn Ala Ala Ile Asn Tyr Gln Asn Leu Tyr Leu Gly Leu Arg
            290                 295                 300 ttc atc atc aag aag gcc tcc aac tcc cgt aac atc aac aac gac aac      963
Phe Ile Ile Lys Lys Ala Ser Asn Ser Arg Asn Ile Asn Asn Asp Asn
            305                 310                 315 atc gtc cgt gag ggt gac tac atc tac ctg aac atc gac aac atc tcc     1011
Ile Val Arg Glu Gly Asp Tyr Ile Tyr Leu Asn Ile Asp Asn Ile Ser
            320                 325                 330 gac gag tcc tac cgt gtc tac gtc ctg gtc aac tcc aag gag atc cag     1059
Asp Glu Ser Tyr Arg Val Tyr Val Leu Val Asn Ser Lys Glu Ile Gln
335                 340                 345                 350 acc cag ctg ttc ctg gcc cca atc aac gac gac cct acc ttc tac gac     1107
Thr Gln Leu Phe Leu Ala Pro Ile Asn Asp Asp Pro Thr Phe Tyr Asp
                355                 360                 365 gtc ctg cag atc aag aag tac tac gag aag acc acc tac aac tgt cag     1155
Val Leu Gln Ile Lys Lys Tyr Tyr Glu Lys Thr Thr Tyr Asn Cys Gln
            370                 375                 380 atc ctg tgc gag aag gac acc aag acc ttc gga ctg ttc ggt atc ggt     1203
Ile Leu Cys Glu Lys Asp Thr Lys Thr Phe Gly Leu Phe Gly Ile Gly
            385                 390                 395 aag ttc gtc aag gac tac ggt tac gtc tgg gac acc tac gac aac tac     1251
```

```
Lys Phe Val Lys Asp Tyr Gly Tyr Val Trp Asp Thr Tyr Asp Asn Tyr
            400                 405                 410 ttc tgt atc tcc cag tgg tac ctg cgt cgt atc tcc gag aac atc aac    1299
Phe Cys Ile Ser Gln Trp Tyr Leu Arg Arg Ile Ser Glu Asn Ile Asn
415                 420                 425                 430 aag ctg cgt ctg gga tgt aac tgg cag ttc atc cca gtc gac gag ggt    1347
Lys Leu Arg Leu Gly Cys Asn Trp Gln Phe Ile Pro Val Asp Glu Gly
                    435                 440                 445 tgg acc gag taataggaat tc                                          1368
Trp Thr Glu <210> SEQ ID NO 18
<211> LENGTH: 449
<212> TYPE: PRT
<213> ORGANISM: Artificial Sequence
<220> FEATURE:
<223> OTHER INFORMATION: Synthetic Construct

<400> SEQUENCE: 18

Met Lys Asp Thr Ile Leu Ile Gln Val Phe Asn Asn Tyr Ile Ser Asn
1               5                   10                  15

Ile Ser Ser Asn Ala Ile Leu Ser Leu Ser Tyr Arg Gly Gly Arg Leu
            20                  25                  30

Ile Asp Ser Ser Gly Tyr Gly Ala Thr Met Asn Val Gly Ser Asp Val
        35                  40                  45

Ile Phe Asn Asp Ile Gly Asn Gly Gln Phe Lys Leu Asn Asn Ser Glu
    50                  55                  60

Asn Ser Asn Ile Thr Ala His Gln Ser Lys Phe Val Val Tyr Asp Ser
65                  70                  75                  80

Met Phe Asp Asn Phe Ser Ile Asn Phe Trp Val Arg Thr Pro Lys Tyr
                85                  90                  95

Asn Asn Asn Asp Ile Gln Thr Tyr Leu Gln Asn Glu Tyr Thr Ile Ile
            100                 105                 110

Ser Cys Ile Lys Asn Asp Ser Gly Trp Lys Val Ser Ile Lys Gly Asn
        115                 120                 125

Arg Ile Ile Trp Thr Leu Ile Asp Val Asn Ala Lys Ser Lys Ser Ile
    130                 135                 140

Phe Phe Glu Tyr Ser Ile Lys Asp Asn Ile Ser Asp Tyr Ile Asn Lys
145                 150                 155                 160

Trp Phe Ser Ile Thr Ile Thr Asn Asp Arg Leu Gly Asn Ala Asn Ile
                165                 170                 175

Tyr Ile Asn Gly Ser Leu Lys Lys Ser Glu Lys Ile Leu Asn Leu Asp
            180                 185                 190

Arg Ile Asn Ser Ser Asn Asp Ile Asp Phe Lys Leu Ile Asn Cys Thr
        195                 200                 205

Asp Thr Thr Lys Phe Val Trp Ile Lys Asp Phe Asn Ile Phe Gly Arg
    210                 215                 220

Glu Leu Asn Ala Thr Glu Val Ser Ser Leu Tyr Trp Ile Gln Ser Ser
225                 230                 235                 240

Thr Asn Thr Leu Lys Asp Phe Trp Gly Asn Pro Leu Arg Tyr Asp Thr
                245                 250                 255

Gln Tyr Tyr Leu Phe Asn Gln Gly Met Gln Asn Ile Tyr Ile Lys Tyr
            260                 265                 270

Phe Ser Lys Ala Ser Met Gly Glu Thr Ala Pro Arg Thr Asn Phe Asn
        275                 280                 285

Asn Ala Ala Ile Asn Tyr Gln Asn Leu Tyr Leu Gly Leu Arg Phe Ile
```

```
                290                 295                 300
Ile Lys Lys Ala Ser Asn Ser Arg Asn Ile Asn Asn Asp Asn Ile Val
305                 310                 315                 320

Arg Glu Gly Asp Tyr Ile Tyr Leu Asn Ile Asp Asn Ile Ser Asp Glu
                325                 330                 335

Ser Tyr Arg Val Tyr Val Leu Val Asn Ser Lys Glu Ile Gln Thr Gln
                340                 345                 350

Leu Phe Leu Ala Pro Ile Asn Asp Asp Pro Thr Phe Tyr Asp Val Leu
                355                 360                 365

Gln Ile Lys Lys Tyr Tyr Glu Lys Thr Thr Tyr Asn Cys Gln Ile Leu
370                 375                 380

Cys Glu Lys Asp Thr Lys Thr Phe Gly Leu Phe Gly Ile Gly Lys Phe
385                 390                 395                 400

Val Lys Asp Tyr Gly Tyr Val Trp Asp Thr Tyr Asp Asn Tyr Phe Cys
                405                 410                 415

Ile Ser Gln Trp Tyr Leu Arg Arg Ile Ser Glu Asn Ile Asn Lys Leu
                420                 425                 430

Arg Leu Gly Cys Asn Trp Gln Phe Ile Pro Val Asp Glu Gly Trp Thr
                435                 440                 445

Glu

<210> SEQ ID NO 19
<211> LENGTH: 1242
<212> TYPE: DNA
<213> ORGANISM: Artificial Sequence
<220> FEATURE:
<223> OTHER INFORMATION: Synthetic Construct
<221> NAME/KEY: CDS
<222> LOCATION: (1)...(1239)

<400> SEQUENCE: 19 atg gct ctg aac gac ctg tgc atc aaa gtt aac aac tgg gac ctg ttc      48
Met Ala Leu Asn Asp Leu Cys Ile Lys Val Asn Asn Trp Asp Leu Phe
1               5                   10                  15 ttc tcc ccg tct gaa gac aac ttc act aac gac ctg aac aaa ggc gaa      96
Phe Ser Pro Ser Glu Asp Asn Phe Thr Asn Asp Leu Asn Lys Gly Glu
                20                  25                  30 gaa atc acc tcc gac act aac atc gaa gct gct gaa gaa aac atc tct     144
Glu Ile Thr Ser Asp Thr Asn Ile Glu Ala Ala Glu Glu Asn Ile Ser
            35                  40                  45 ctg gac ctg atc cag cag tac tac ctg act ttc aac ttc gac aac gaa     192
Leu Asp Leu Ile Gln Gln Tyr Tyr Leu Thr Phe Asn Phe Asp Asn Glu
        50                  55                  60 ccg gaa aac atc tcc atc gaa aac ctg tct tcc gac atc atc ggt cag     240
Pro Glu Asn Ile Ser Ile Glu Asn Leu Ser Ser Asp Ile Ile Gly Gln
65                  70                  75                  80 ctg gaa ctg atg ccg aac atc gaa cgc ttc ccg aac ggc aag aaa tac     288
Leu Glu Leu Met Pro Asn Ile Glu Arg Phe Pro Asn Gly Lys Lys Tyr
                85                  90                  95 gaa ctg gac aaa tac acc atg ttc cac tac ctg cgt gct cag gaa ttc     336
Glu Leu Asp Lys Tyr Thr Met Phe His Tyr Leu Arg Ala Gln Glu Phe
                100                 105                 110 gaa cac ggt aaa tct cgt atc gct ctg act aac tcc gtt aac gaa gct     384
Glu His Gly Lys Ser Arg Ile Ala Leu Thr Asn Ser Val Asn Glu Ala
            115                 120                 125 ctg ctg aac ccg tct cgc gtt tac acc ttc ttc tct tcc gac tac gtt     432
Leu Leu Asn Pro Ser Arg Val Tyr Thr Phe Phe Ser Ser Asp Tyr Val
        130                 135                 140
```

```
aag aaa gtt aac aaa gct act gaa gct gct atg ttc ctg ggt tgg gtt      480
Lys Lys Val Asn Lys Ala Thr Glu Ala Ala Met Phe Leu Gly Trp Val
145                 150                 155                 160 gaa cag ctg gtt tac gac ttc acc gac gaa act tct gaa gtt tcc acc      528
Glu Gln Leu Val Tyr Asp Phe Thr Asp Glu Thr Ser Glu Val Ser Thr
                165                 170                 175 act gac aaa atc gct gac atc act atc atc ccg tac atc ggc ccg          576
Thr Asp Lys Ile Ala Asp Ile Thr Ile Ile Pro Tyr Ile Gly Pro
            180                 185                 190 gct ctg aac atc ggt aac atg ctg tac aaa gac gac ttc gtt ggt gct      624
Ala Leu Asn Ile Gly Asn Met Leu Tyr Lys Asp Asp Phe Val Gly Ala
        195                 200                 205 ctg atc ttc tct ggc gct gtt atc ctg ctg gaa ttc atc ccg gaa atc      672
Leu Ile Phe Ser Gly Ala Val Ile Leu Leu Glu Phe Ile Pro Glu Ile
    210                 215                 220 gct atc ccg gtt ctg ggt acc ttc gct ctg gtt tcc tac atc gct aac      720
Ala Ile Pro Val Leu Gly Thr Phe Ala Leu Val Ser Tyr Ile Ala Asn
225                 230                 235                 240 aaa gtt ctg act gtt cag acc atc gac aac gct ctg tct aaa cgt aac      768
Lys Val Leu Thr Val Gln Thr Ile Asp Asn Ala Leu Ser Lys Arg Asn
                245                 250                 255 gaa aaa tgg gac gaa gtt tac aaa tac atc gtt act aac tgg ctg gct      816
Glu Lys Trp Asp Glu Val Tyr Lys Tyr Ile Val Thr Asn Trp Leu Ala
            260                 265                 270 aaa gtt aac act cag atc gac ctg atc cgt aag aag atg aaa gaa gct      864
Lys Val Asn Thr Gln Ile Asp Leu Ile Arg Lys Lys Met Lys Glu Ala
        275                 280                 285 ctg gaa aac cag gct gaa gct act aaa gct atc atc aac tac cag tac      912
Leu Glu Asn Gln Ala Glu Ala Thr Lys Ala Ile Ile Asn Tyr Gln Tyr
    290                 295                 300 aac cag tac acc gaa gaa gaa aag aac aac atc aac ttc aac atc gat      960
Asn Gln Tyr Thr Glu Glu Glu Lys Asn Asn Ile Asn Phe Asn Ile Asp
305                 310                 315                 320 gac ctg tcc tct aaa ctg aac gaa tcc atc aac aaa gct atg atc aac     1008
Asp Leu Ser Ser Lys Leu Asn Glu Ser Ile Asn Lys Ala Met Ile Asn
                325                 330                 335 atc aac aaa ttc ctg aac cag tgc tct gtt tcc tac ctg atg aac tct     1056
Ile Asn Lys Phe Leu Asn Gln Cys Ser Val Ser Tyr Leu Met Asn Ser
            340                 345                 350 atg atc ccg tac ggc gtt aaa cgc ctg gaa gac ttc gac gct tcc ctg     1104
Met Ile Pro Tyr Gly Val Lys Arg Leu Glu Asp Phe Asp Ala Ser Leu
        355                 360                 365 aaa gac gct ctg ctg aaa tac atc cgt gac aac tac ggt act ctg atc     1152
Lys Asp Ala Leu Leu Lys Tyr Ile Arg Asp Asn Tyr Gly Thr Leu Ile
    370                 375                 380 ggc cag gtt gac cgt ctg aaa gac aag gtt aac aac acc ctg tct act     1200
Gly Gln Val Asp Arg Leu Lys Asp Lys Val Asn Asn Thr Leu Ser Thr
385                 390                 395                 400 gac atc ccg ttc cag ctg tcc aaa tac gtt gac aac cag taa             1242
Asp Ile Pro Phe Gln Leu Ser Lys Tyr Val Asp Asn Gln
                405                 410
```

<210> SEQ ID NO 20
<211> LENGTH: 413
<212> TYPE: PRT
<213> ORGANISM: Artificial Sequence
<220> FEATURE:
<223> OTHER INFORMATION: Synthetic Construct

<400> SEQUENCE: 20

Met Ala Leu Asn Asp Leu Cys Ile Lys Val Asn Asn Trp Asp Leu Phe

-continued

```
  1               5                  10                 15

Phe Ser Pro Ser Glu Asp Asn Phe Thr Asn Asp Leu Asn Lys Gly Glu
            20                  25                  30

Glu Ile Thr Ser Asp Thr Asn Ile Glu Ala Ala Glu Glu Asn Ile Ser
            35                  40                  45

Leu Asp Leu Ile Gln Gln Tyr Tyr Leu Thr Phe Asn Phe Asp Asn Glu
50                      55                  60

Pro Glu Asn Ile Ser Ile Glu Asn Leu Ser Ser Asp Ile Ile Gly Gln
65                      70                  75                  80

Leu Glu Leu Met Pro Asn Ile Glu Arg Phe Pro Asn Gly Lys Lys Tyr
                    85                  90                  95

Glu Leu Asp Lys Tyr Thr Met Phe His Tyr Leu Arg Ala Gln Glu Phe
                    100                 105                 110

Glu His Gly Lys Ser Arg Ile Ala Leu Thr Asn Ser Val Asn Glu Ala
                    115                 120                 125

Leu Leu Asn Pro Ser Arg Val Tyr Thr Phe Phe Ser Ser Asp Tyr Val
            130                 135                 140

Lys Lys Val Asn Lys Ala Thr Glu Ala Ala Met Phe Leu Gly Trp Val
145                     150                 155                 160

Glu Gln Leu Val Tyr Asp Phe Thr Asp Glu Thr Ser Glu Val Ser Thr
                    165                 170                 175

Thr Asp Lys Ile Ala Asp Ile Thr Ile Ile Pro Tyr Ile Gly Pro
                    180                 185                 190

Ala Leu Asn Ile Gly Asn Met Leu Tyr Lys Asp Asp Phe Val Gly Ala
            195                 200                 205

Leu Ile Phe Ser Gly Ala Val Ile Leu Leu Glu Phe Ile Pro Glu Ile
    210                 215                 220

Ala Ile Pro Val Leu Gly Thr Phe Ala Leu Val Ser Tyr Ile Ala Asn
225                     230                 235                 240

Lys Val Leu Thr Val Gln Thr Ile Asp Asn Ala Leu Ser Lys Arg Asn
                    245                 250                 255

Glu Lys Trp Asp Glu Val Tyr Lys Tyr Ile Val Thr Asn Trp Leu Ala
                    260                 265                 270

Lys Val Asn Thr Gln Ile Asp Leu Ile Arg Lys Lys Met Lys Glu Ala
            275                 280                 285

Leu Glu Asn Gln Ala Glu Ala Thr Lys Ala Ile Ile Asn Tyr Gln Tyr
    290                 295                 300

Asn Gln Tyr Thr Glu Glu Glu Lys Asn Asn Ile Asn Phe Asn Ile Asp
305                     310                 315                 320

Asp Leu Ser Ser Lys Leu Asn Glu Ser Ile Asn Lys Ala Met Ile Asn
                    325                 330                 335

Ile Asn Lys Phe Leu Asn Gln Cys Ser Val Ser Tyr Leu Met Asn Ser
                    340                 345                 350

Met Ile Pro Tyr Gly Val Lys Arg Leu Glu Asp Phe Asp Ala Ser Leu
            355                 360                 365

Lys Asp Ala Leu Leu Lys Tyr Ile Arg Asp Asn Tyr Gly Thr Leu Ile
370                     375                 380

Gly Gln Val Asp Arg Leu Lys Asp Lys Val Asn Asn Thr Leu Ser Thr
385                     390                 395                 400

Asp Ile Pro Phe Gln Leu Ser Lys Tyr Val Asp Asn Gln
                    405                 410

<210> SEQ ID NO 21
```

-continued

```
<211> LENGTH: 1242
<212> TYPE: DNA
<213> ORGANISM: Artificial Sequence
<220> FEATURE:
<223> OTHER INFORMATION: Synthetic Construct
<221> NAME/KEY: CDS
<222> LOCATION: (1)...(1239)

<400> SEQUENCE: 21 atg gct cca gga atc tgt atc gac gtc gac aac gag gac ttg ttc ttc      48
Met Ala Pro Gly Ile Cys Ile Asp Val Asp Asn Glu Asp Leu Phe Phe
 1               5                  10                  15 atc gct gac aag aac tcc ttc tcc gac gac ttg tcc aag aac gag aga      96
Ile Ala Asp Lys Asn Ser Phe Ser Asp Asp Leu Ser Lys Asn Glu Arg
             20                  25                  30 atc gag tac aac acc cag tcc aac tac atc gag aac gac ttc cca atc     144
Ile Glu Tyr Asn Thr Gln Ser Asn Tyr Ile Glu Asn Asp Phe Pro Ile
         35                  40                  45 aac gag ttg atc ttg gac acc gac ttg atc tcc aag atc gag ttg cca     192
Asn Glu Leu Ile Leu Asp Thr Asp Leu Ile Ser Lys Ile Glu Leu Pro
     50                  55                  60 tcc gag aac acc gag tcc ttg act gac ttc aac gtc gac gtc cca gtc     240
Ser Glu Asn Thr Glu Ser Leu Thr Asp Phe Asn Val Asp Val Pro Val
 65                  70                  75                  80 tac gag aag caa cca gct atc aag aag att ttc acc gac gag aac acc     288
Tyr Glu Lys Gln Pro Ala Ile Lys Lys Ile Phe Thr Asp Glu Asn Thr
                 85                  90                  95 atc ttc caa tac ctg tac tct cag acc ttc cct ttg gac atc aga gac     336
Ile Phe Gln Tyr Leu Tyr Ser Gln Thr Phe Pro Leu Asp Ile Arg Asp
            100                 105                 110 atc tcc ttg acc tct tcc ttc gac gac gcc ctg ctg ttc tcc aac aag     384
Ile Ser Leu Thr Ser Ser Phe Asp Asp Ala Leu Leu Phe Ser Asn Lys
        115                 120                 125 gtc tac tcc ttc ttc tcc atg gac tac atc aag act gct aac aag gtc     432
Val Tyr Ser Phe Phe Ser Met Asp Tyr Ile Lys Thr Ala Asn Lys Val
    130                 135                 140 gtc gag gcc ggt ttg ttc gct ggt tgg gtc aag cag atc gtc aac gat     480
Val Glu Ala Gly Leu Phe Ala Gly Trp Val Lys Gln Ile Val Asn Asp
145                 150                 155                 160 ttc gtc atc gag gct aac aag tcc aac acc atg gac aag att gcc gac     528
Phe Val Ile Glu Ala Asn Lys Ser Asn Thr Met Asp Lys Ile Ala Asp
                165                 170                 175 atc tcc ttg att gtc cca tac atc ggt ttg gcc ttg aac gtc ggt aac     576
Ile Ser Leu Ile Val Pro Tyr Ile Gly Leu Ala Leu Asn Val Gly Asn
            180                 185                 190 gag acc gcc aag ggt aac ttc gag aac gct ttc gag atc gct ggt gcc     624
Glu Thr Ala Lys Gly Asn Phe Glu Asn Ala Phe Glu Ile Ala Gly Ala
        195                 200                 205 tcc atc ttg ttg gag ttc atc cca gag ttg ttg atc cca gtc gtc ggt     672
Ser Ile Leu Leu Glu Phe Ile Pro Glu Leu Leu Ile Pro Val Val Gly
    210                 215                 220 gcc ttc ttg ttg gag tcc tac atc gac aac aag aac aag atc atc aag     720
Ala Phe Leu Leu Glu Ser Tyr Ile Asp Asn Lys Asn Lys Ile Ile Lys
225                 230                 235                 240 acc atc gac aac gct ttg acc aag aga aac gag aag tgg tcc gac atg     768
Thr Ile Asp Asn Ala Leu Thr Lys Arg Asn Glu Lys Trp Ser Asp Met
                245                 250                 255 tac ggt ttg atc gtc gcc caa tgg ttg tcc acc gtc aac acc caa ttc     816
Tyr Gly Leu Ile Val Ala Gln Trp Leu Ser Thr Val Asn Thr Gln Phe
            260                 265                 270 tac acc atc aag gag ggt atg tac aag gcc ttg aac tac cag gcc caa     864
Tyr Thr Ile Lys Glu Gly Met Tyr Lys Ala Leu Asn Tyr Gln Ala Gln
```

```
Tyr Thr Ile Lys Glu Gly Met Tyr Lys Ala Leu Asn Tyr Gln Ala Gln
            275                 280                 285 gct ttg gag gag atc atc aag tac aga tac aac atc tac tcc gag aag      912
Ala Leu Glu Glu Ile Ile Lys Tyr Arg Tyr Asn Ile Tyr Ser Glu Lys
        290                 295                 300 gag aag tcc aac att aac atc gac ttc aac gac atc aac tcc aag ctg      960
Glu Lys Ser Asn Ile Asn Ile Asp Phe Asn Asp Ile Asn Ser Lys Leu
305                 310                 315                 320 aac gag ggt att aac cag gcc atc gac aac atc aac aac ttc atc aac     1008
Asn Glu Gly Ile Asn Gln Ala Ile Asp Asn Ile Asn Asn Phe Ile Asn
                325                 330                 335 ggt tgt tcc gtc tcc tac ttg atg aag aag atg att cca ttg gcc gtc     1056
Gly Cys Ser Val Ser Tyr Leu Met Lys Lys Met Ile Pro Leu Ala Val
            340                 345                 350 gag aag ttg ttg gac ttc gac aac acc ctg aag aag aac ttg ttg aac     1104
Glu Lys Leu Leu Asp Phe Asp Asn Thr Leu Lys Lys Asn Leu Leu Asn
        355                 360                 365 tac atc gac gag aac aag ttg tac ttg atc ggt tcc gct gag tac gag     1152
Tyr Ile Asp Glu Asn Lys Leu Tyr Leu Ile Gly Ser Ala Glu Tyr Glu
    370                 375                 380 aag tcc aag gtc aac aag tac ttg aag acc atc atg cca ttc gac ttg     1200
Lys Ser Lys Val Asn Lys Tyr Leu Lys Thr Ile Met Pro Phe Asp Leu
385                 390                 395                 400 tcc atc tac acc aac gac acc atc ttg atc gag atg ttc taa              1242
Ser Ile Tyr Thr Asn Asp Thr Ile Leu Ile Glu Met Phe
                405                 410

<210> SEQ ID NO 22
<211> LENGTH: 413
<212> TYPE: PRT
<213> ORGANISM: Artificial Sequence
<220> FEATURE:
<223> OTHER INFORMATION: Synthetic Construct

<400> SEQUENCE: 22

Met Ala Pro Gly Ile Cys Ile Asp Val Asp Asn Glu Asp Leu Phe Phe
1               5                   10                  15

Ile Ala Asp Lys Asn Ser Phe Ser Asp Leu Ser Lys Asn Glu Arg
            20                  25                  30

Ile Glu Tyr Asn Thr Gln Ser Asn Tyr Ile Glu Asn Asp Phe Pro Ile
        35                  40                  45

Asn Glu Leu Ile Leu Asp Thr Asp Leu Ile Ser Lys Ile Glu Leu Pro
    50                  55                  60

Ser Glu Asn Thr Glu Ser Leu Thr Asp Phe Asn Val Asp Val Pro Val
65                  70                  75                  80

Tyr Glu Lys Gln Pro Ala Ile Lys Lys Ile Phe Thr Asp Glu Asn Thr
                85                  90                  95

Ile Phe Gln Tyr Leu Tyr Ser Gln Thr Phe Pro Leu Asp Ile Arg Asp
            100                 105                 110

Ile Ser Leu Thr Ser Ser Phe Asp Asp Ala Leu Leu Phe Ser Asn Lys
        115                 120                 125

Val Tyr Ser Phe Phe Ser Met Asp Tyr Ile Lys Thr Ala Asn Lys Val
    130                 135                 140

Val Glu Ala Gly Leu Phe Ala Gly Trp Val Lys Gln Ile Val Asn Asp
145                 150                 155                 160

Phe Val Ile Glu Ala Asn Lys Ser Asn Thr Met Asp Lys Ile Ala Asp
                165                 170                 175

Ile Ser Leu Ile Val Pro Tyr Ile Gly Leu Ala Leu Asn Val Gly Asn
```

```
                    180                 185                 190
Glu Thr Ala Lys Gly Asn Phe Glu Asn Ala Phe Glu Ile Ala Gly Ala
                195                 200                 205

Ser Ile Leu Leu Glu Phe Ile Pro Glu Leu Leu Ile Pro Val Val Gly
210                 215                 220

Ala Phe Leu Leu Glu Ser Tyr Ile Asp Asn Lys Asn Lys Ile Ile Lys
225                 230                 235                 240

Thr Ile Asp Asn Ala Leu Thr Lys Arg Asn Glu Lys Trp Ser Asp Met
                245                 250                 255

Tyr Gly Leu Ile Val Ala Gln Trp Leu Ser Thr Val Asn Thr Gln Phe
                260                 265                 270

Tyr Thr Ile Lys Glu Gly Met Tyr Lys Ala Leu Asn Tyr Gln Ala Gln
                275                 280                 285

Ala Leu Glu Glu Ile Ile Lys Tyr Arg Tyr Asn Ile Tyr Ser Glu Lys
290                 295                 300

Glu Lys Ser Asn Ile Asn Ile Asp Phe Asn Asp Ile Asn Ser Lys Leu
305                 310                 315                 320

Asn Glu Gly Ile Asn Gln Ala Ile Asp Asn Ile Asn Asn Phe Ile Asn
                325                 330                 335

Gly Cys Ser Val Ser Tyr Leu Met Lys Lys Met Ile Pro Leu Ala Val
                340                 345                 350

Glu Lys Leu Leu Asp Phe Asp Asn Thr Leu Lys Lys Asn Leu Leu Asn
                355                 360                 365

Tyr Ile Asp Glu Asn Lys Leu Tyr Leu Ile Gly Ser Ala Glu Tyr Glu
370                 375                 380

Lys Ser Lys Val Asn Lys Tyr Leu Lys Thr Ile Met Pro Phe Asp Leu
385                 390                 395                 400

Ser Ile Tyr Thr Asn Asp Thr Ile Leu Ile Glu Met Phe
                405                 410

<210> SEQ ID NO 23
<211> LENGTH: 1200
<212> TYPE: DNA
<213> ORGANISM: Artificial Sequence
<220> FEATURE:
<223> OTHER INFORMATION: Synthetic Construct
<221> NAME/KEY: CDS
<222> LOCATION: (1)...(1197)

<400> SEQUENCE: 23 atg tcc ctg tac aac aag acc ctt gac tgt aga gag ctg ctg gtg aag      48
Met Ser Leu Tyr Asn Lys Thr Leu Asp Cys Arg Glu Leu Leu Val Lys
 1               5                  10                  15 aac act gac ctg cca ttc atc ggt gac atc agt gac gtg aag act gac      96
Asn Thr Asp Leu Pro Phe Ile Gly Asp Ile Ser Asp Val Lys Thr Asp
                 20                  25                  30 atc ttc ctg cgt aag gac atc aac gag gag act gag gtg atc tac tac     144
Ile Phe Leu Arg Lys Asp Ile Asn Glu Glu Thr Glu Val Ile Tyr Tyr
             35                  40                  45 cca gac aac gtg tca gta gac caa gtg atc ctc agt aag aac acc tcc     192
Pro Asp Asn Val Ser Val Asp Gln Val Ile Leu Ser Lys Asn Thr Ser
         50                  55                  60 gag cat gga caa cta gac ctg ctc tac cct agt atc gac agt gag agt     240
Glu His Gly Gln Leu Asp Leu Leu Tyr Pro Ser Ile Asp Ser Glu Ser
 65                  70                  75                  80 gag atc ctg cca ggg gag aat caa gtc ttc tac gac aac cgt acc cag     288
Glu Ile Leu Pro Gly Glu Asn Gln Val Phe Tyr Asp Asn Arg Thr Gln
                 85                  90                  95
```

```
aac gtg gac tac ctg aac tcc tac tac tac cta gag tct cag aag ctg    336
Asn Val Asp Tyr Leu Asn Ser Tyr Tyr Tyr Leu Glu Ser Gln Lys Leu
            100                 105                 110 agt gac aac gtg gag gac ttc act ttc acg cgt tca atc gag gag gct    384
Ser Asp Asn Val Glu Asp Phe Thr Phe Thr Arg Ser Ile Glu Glu Ala
            115                 120                 125 ctg gac aac agt gca aag gtg tac act tac ttc cct acc ctg gct aac    432
Leu Asp Asn Ser Ala Lys Val Tyr Thr Tyr Phe Pro Thr Leu Ala Asn
        130                 135                 140 aag gtg aat gcc ggt gtg caa ggt ggt ctg ttc ctg atg tgg gca aac    480
Lys Val Asn Ala Gly Val Gln Gly Gly Leu Phe Leu Met Trp Ala Asn
145                 150                 155                 160 gac gtg gtt gag gac ttc act acc aac atc ctg cgt aag gac aca ctg    528
Asp Val Val Glu Asp Phe Thr Thr Asn Ile Leu Arg Lys Asp Thr Leu
                165                 170                 175 gac aag atc tca gat gtg tca gct atc atc ccc tac atc gga ccc gca    576
Asp Lys Ile Ser Asp Val Ser Ala Ile Ile Pro Tyr Ile Gly Pro Ala
            180                 185                 190 ctg aac atc tcc aac tct gtg cgt cgt gga aac ttc act gag gca ttc    624
Leu Asn Ile Ser Asn Ser Val Arg Arg Gly Asn Phe Thr Glu Ala Phe
            195                 200                 205 gca gtc act ggt gtc acc atc ctg ctg gag gca ttc cct gag ttc aca    672
Ala Val Thr Gly Val Thr Ile Leu Leu Glu Ala Phe Pro Glu Phe Thr
210                 215                 220 atc cct gct ctg ggt gca ttc gtg atc tac agt aag gtc cag gag cga    720
Ile Pro Ala Leu Gly Ala Phe Val Ile Tyr Ser Lys Val Gln Glu Arg
225                 230                 235                 240 aac gag atc atc aag acc atc gac aac tgt ctg gag cag agg atc aag    768
Asn Glu Ile Ile Lys Thr Ile Asp Asn Cys Leu Glu Gln Arg Ile Lys
                245                 250                 255 aga tgg aag gac tcc tac gag tgg atg atg gga acg tgg ttg tcc agg    816
Arg Trp Lys Asp Ser Tyr Glu Trp Met Met Gly Thr Trp Leu Ser Arg
            260                 265                 270 atc atc acc cag ttc aac aac atc tcc tac cag atg tac gac tcc ctg    864
Ile Ile Thr Gln Phe Asn Asn Ile Ser Tyr Gln Met Tyr Asp Ser Leu
            275                 280                 285 aac tac cag gca ggt gca atc aag gct aag atc gac ctg gag tac aag    912
Asn Tyr Gln Ala Gly Ala Ile Lys Ala Lys Ile Asp Leu Glu Tyr Lys
        290                 295                 300 aag tac tcc gga agc gac aag gag aac atc aag agc cag gtt gag aac    960
Lys Tyr Ser Gly Ser Asp Lys Glu Asn Ile Lys Ser Gln Val Glu Asn
305                 310                 315                 320 ctg aag aac agt ctg gac gtc aag atc tcg gag gca atg aac aac atc    1008
Leu Lys Asn Ser Leu Asp Val Lys Ile Ser Glu Ala Met Asn Asn Ile
                325                 330                 335 aac aag ttc atc cga gag tgc tcc gtc acc tac ctg ttc aag aac atg    1056
Asn Lys Phe Ile Arg Glu Cys Ser Val Thr Tyr Leu Phe Lys Asn Met
            340                 345                 350 ctg cct aag gtc atc gac gag ctg aac gag ttc gac cga aac acc aag    1104
Leu Pro Lys Val Ile Asp Glu Leu Asn Glu Phe Asp Arg Asn Thr Lys
        355                 360                 365 gca aag ctg atc aac ctg atc gac tcc cat aac atc atc ctg gtc ggt    1152
Ala Lys Leu Ile Asn Leu Ile Asp Ser His Asn Ile Ile Leu Val Gly
370                 375                 380 gag gtc gac aag ctg aag gca aag gta aac aac agc ttc cag aac        1197
Glu Val Asp Lys Leu Lys Ala Lys Val Asn Asn Ser Phe Gln Asn
385                 390                 395 taa                                                                1200
```

```
<210> SEQ ID NO 24
<211> LENGTH: 399
<212> TYPE: PRT
<213> ORGANISM: Artificial Sequence
<220> FEATURE:
<223> OTHER INFORMATION: Synthetic Construct

<400> SEQUENCE: 24

Met Ser Leu Tyr Asn Lys Thr Leu Asp Cys Arg Glu Leu Leu Val Lys
 1               5                  10                  15

Asn Thr Asp Leu Pro Phe Ile Gly Asp Ile Ser Asp Val Lys Thr Asp
                20                  25                  30

Ile Phe Leu Arg Lys Asp Ile Asn Glu Glu Thr Glu Val Ile Tyr Tyr
            35                  40                  45

Pro Asp Asn Val Ser Val Asp Gln Val Ile Leu Ser Lys Asn Thr Ser
 50                  55                  60

Glu His Gly Gln Leu Asp Leu Leu Tyr Pro Ser Ile Asp Ser Glu Ser
 65                  70                  75                  80

Glu Ile Leu Pro Gly Glu Asn Gln Val Phe Tyr Asp Asn Arg Thr Gln
                85                  90                  95

Asn Val Asp Tyr Leu Asn Ser Tyr Tyr Tyr Leu Glu Ser Gln Lys Leu
               100                 105                 110

Ser Asp Asn Val Glu Asp Phe Thr Phe Thr Arg Ser Ile Glu Glu Ala
           115                 120                 125

Leu Asp Asn Ser Ala Lys Val Tyr Thr Tyr Phe Pro Thr Leu Ala Asn
       130                 135                 140

Lys Val Asn Ala Gly Val Gln Gly Gly Leu Phe Leu Met Trp Ala Asn
145                 150                 155                 160

Asp Val Val Glu Asp Phe Thr Thr Asn Ile Leu Arg Lys Asp Thr Leu
               165                 170                 175

Asp Lys Ile Ser Asp Val Ser Ala Ile Ile Pro Tyr Ile Gly Pro Ala
           180                 185                 190

Leu Asn Ile Ser Asn Ser Val Arg Arg Gly Asn Phe Thr Glu Ala Phe
       195                 200                 205

Ala Val Thr Gly Val Thr Ile Leu Leu Glu Ala Phe Pro Glu Phe Thr
210                 215                 220

Ile Pro Ala Leu Gly Ala Phe Val Ile Tyr Ser Lys Val Gln Glu Arg
225                 230                 235                 240

Asn Glu Ile Ile Lys Thr Ile Asp Asn Cys Leu Glu Gln Arg Ile Lys
               245                 250                 255

Arg Trp Lys Asp Ser Tyr Glu Trp Met Met Gly Thr Trp Leu Ser Arg
           260                 265                 270

Ile Ile Thr Gln Phe Asn Asn Ile Ser Tyr Gln Met Tyr Asp Ser Leu
       275                 280                 285

Asn Tyr Gln Ala Gly Ala Ile Lys Ala Lys Ile Asp Leu Glu Tyr Lys
   290                 295                 300

Lys Tyr Ser Gly Ser Asp Lys Glu Asn Ile Lys Ser Gln Val Glu Asn
305                 310                 315                 320

Leu Lys Asn Ser Leu Asp Val Lys Ile Ser Glu Ala Met Asn Asn Ile
               325                 330                 335

Asn Lys Phe Ile Arg Glu Cys Ser Val Thr Tyr Leu Phe Lys Asn Met
           340                 345                 350

Leu Pro Lys Val Ile Asp Glu Leu Asn Glu Phe Asp Arg Asn Thr Lys
       355                 360                 365
```

-continued

```
Ala Lys Leu Ile Asn Leu Ile Asp Ser His Asn Ile Ile Leu Val Gly
    370                 375                 380

Glu Val Asp Lys Leu Lys Ala Lys Val Asn Asn Ser Phe Gln Asn
385                 390                 395

<210> SEQ ID NO 25
<211> LENGTH: 1161
<212> TYPE: DNA
<213> ORGANISM: Artificial Sequence
<220> FEATURE:
<223> OTHER INFORMATION: Synthetic Construct
<221> NAME/KEY: CDS
<222> LOCATION: (1)...(1158)

<400> SEQUENCE: 25 atg gcc aac tcc cgt gac gac tcc acc tgc atc aag gtc aag aac aac      48
Met Ala Asn Ser Arg Asp Asp Ser Thr Cys Ile Lys Val Lys Asn Asn
  1               5                  10                  15 aga ctg cca tac gtt gcc gac aag gac tcc atc tcc cag gag atc ttc      96
Arg Leu Pro Tyr Val Ala Asp Lys Asp Ser Ile Ser Gln Glu Ile Phe
                 20                  25                  30 gag aac aag atc atc acc gac gag acc aac gtt caa aac tac tcc gac     144
Glu Asn Lys Ile Ile Thr Asp Glu Thr Asn Val Gln Asn Tyr Ser Asp
             35                  40                  45 aag ttc tct ttg gac gag tcc atc ctg gac ggt cag gtc cca atc aac     192
Lys Phe Ser Leu Asp Glu Ser Ile Leu Asp Gly Gln Val Pro Ile Asn
         50                  55                  60 cca gag atc gtc gac cca ctg ttg cca aac gtc aac atg gag cca ttg     240
Pro Glu Ile Val Asp Pro Leu Leu Pro Asn Val Asn Met Glu Pro Leu
 65                  70                  75                  80 aac ttg cca ggt gag gag atc gtc ttc tac gac gac atc acc aag tac     288
Asn Leu Pro Gly Glu Glu Ile Val Phe Tyr Asp Asp Ile Thr Lys Tyr
                 85                  90                  95 gtc gac tac ttg aac tcc tac tac ttg gag tct caa aag ttg tct         336
Val Asp Tyr Leu Asn Ser Tyr Tyr Leu Glu Ser Gln Lys Leu Ser
                100                 105                 110 aac aac gtc gag aac atc acc ttg acc acc tcc gtc gag gag gcc ttg     384
Asn Asn Val Glu Asn Ile Thr Leu Thr Thr Ser Val Glu Glu Ala Leu
            115                 120                 125 ggt tac tct aac aag atc tac acc ttc ctg cca tcc ttg gct gag aag     432
Gly Tyr Ser Asn Lys Ile Tyr Thr Phe Leu Pro Ser Leu Ala Glu Lys
        130                 135                 140 gtt aac aag ggt gtt caa gct ggt ttg ttc ctg aac tgg gcc aac gag     480
Val Asn Lys Gly Val Gln Ala Gly Leu Phe Leu Asn Trp Ala Asn Glu
145                 150                 155                 160 gtc gtc gag gac ttc acc acc aac atc atg aag aag gac acc ctg gac     528
Val Val Glu Asp Phe Thr Thr Asn Ile Met Lys Lys Asp Thr Leu Asp
                165                 170                 175 aag atc tcc gac gtc tcc gtc atc atc cca tac atc ggt cca gcc ttg     576
Lys Ile Ser Asp Val Ser Val Ile Ile Pro Tyr Ile Gly Pro Ala Leu
            180                 185                 190 aac atc ggt aac tcc gcc ctg aga ggt aac ttc aac cag gcc ttc gcc     624
Asn Ile Gly Asn Ser Ala Leu Arg Gly Asn Phe Asn Gln Ala Phe Ala
        195                 200                 205 acc gcc ggt gtc gcc ttc ctg ctg gag ggt ttc cca gag ttc acc atc     672
Thr Ala Gly Val Ala Phe Leu Leu Glu Gly Phe Pro Glu Phe Thr Ile
    210                 215                 220 cca gcc ctg ggt gtc ttc acc ttc tac tcc tcc atc cag gag aga gag     720
Pro Ala Leu Gly Val Phe Thr Phe Tyr Ser Ser Ile Gln Glu Arg Glu
225                 230                 235                 240 aag atc atc aag acc atc gag aac tgc ttg gag cag aga gtc aag aga     768
```

-continued

```
                    Lys Ile Ile Lys Thr Ile Glu Asn Cys Leu Glu Gln Arg Val Lys Arg
                                    245                 250                 255 tgg aag gac tcc tac cag tgg atg gtt tcc aac tgg ctg tcc aga atc        816
Trp Lys Asp Ser Tyr Gln Trp Met Val Ser Asn Trp Leu Ser Arg Ile
                260                 265                 270 acc acc caa ttc aac cac atc aac tac cag atg tac gac tcc ctg tcc        864
Thr Thr Gln Phe Asn His Ile Asn Tyr Gln Met Tyr Asp Ser Leu Ser
            275                 280                 285 tac cag gcc gac gcc atc aag gcc aag atc gac ctg gag tac aag aag        912
Tyr Gln Ala Asp Ala Ile Lys Ala Lys Ile Asp Leu Glu Tyr Lys Lys
        290                 295                 300 tac tcc ggt tcc gac aag gag aac atc aag tcc cag gtc gag aac ctg        960
Tyr Ser Gly Ser Asp Lys Glu Asn Ile Lys Ser Gln Val Glu Asn Leu
305                 310                 315                 320 aag aac tcc ttg gac gtc aag atc tcc gag gcc atg aac aac atc aac       1008
Lys Asn Ser Leu Asp Val Lys Ile Ser Glu Ala Met Asn Asn Ile Asn
                325                 330                 335 aag ttc atc cgt gag tgt tcc gtc acc tac ctg ttc aag aac atg ctg       1056
Lys Phe Ile Arg Glu Cys Ser Val Thr Tyr Leu Phe Lys Asn Met Leu
            340                 345                 350 cca aag gtc atc gac gag ctg aac aag ttc gac ctg aga acc aag acc       1104
Pro Lys Val Ile Asp Glu Leu Asn Lys Phe Asp Leu Arg Thr Lys Thr
        355                 360                 365 gag ctg atc aac ctg atc gac tcc cac aac atc atc ctg gtt ggt gag       1152
Glu Leu Ile Asn Leu Ile Asp Ser His Asn Ile Ile Leu Val Gly Glu
370                 375                 380 gtt gac taa                                                           1161
Val Asp
385
```

<210> SEQ ID NO 26
<211> LENGTH: 386
<212> TYPE: PRT
<213> ORGANISM: Artificial Sequence
<220> FEATURE:
<223> OTHER INFORMATION: Synthetic Construct

<400> SEQUENCE: 26

```
Met Ala Asn Ser Arg Asp Asp Ser Thr Cys Ile Lys Val Lys Asn Asn
 1               5                  10                  15

Arg Leu Pro Tyr Val Ala Asp Lys Asp Ser Ile Ser Gln Glu Ile Phe
             20                  25                  30

Glu Asn Lys Ile Ile Thr Asp Glu Thr Asn Val Gln Asn Tyr Ser Asp
         35                  40                  45

Lys Phe Ser Leu Asp Glu Ser Ile Leu Asp Gly Gln Val Pro Ile Asn
     50                  55                  60

Pro Glu Ile Val Asp Pro Leu Leu Pro Asn Val Asn Met Glu Pro Leu
 65                  70                  75                  80

Asn Leu Pro Gly Glu Glu Ile Val Phe Tyr Asp Asp Ile Thr Lys Tyr
                 85                  90                  95

Val Asp Tyr Leu Asn Ser Tyr Tyr Leu Glu Ser Gln Lys Leu Ser
             100                 105                 110

Asn Asn Val Glu Asn Ile Thr Leu Thr Thr Ser Val Glu Glu Ala Leu
         115                 120                 125

Gly Tyr Ser Asn Lys Ile Tyr Thr Phe Leu Pro Ser Leu Ala Glu Lys
     130                 135                 140

Val Asn Lys Gly Val Gln Ala Gly Leu Phe Leu Asn Trp Ala Asn Glu
145                 150                 155                 160
```

```
Val Val Glu Asp Phe Thr Thr Asn Ile Met Lys Lys Asp Thr Leu Asp
            165                 170                 175

Lys Ile Ser Asp Val Ser Val Ile Ile Pro Tyr Ile Gly Pro Ala Leu
            180                 185                 190

Asn Ile Gly Asn Ser Ala Leu Arg Gly Asn Phe Asn Gln Ala Phe Ala
            195                 200                 205

Thr Ala Gly Val Ala Phe Leu Leu Glu Gly Phe Pro Glu Phe Thr Ile
            210                 215                 220

Pro Ala Leu Gly Val Phe Thr Phe Tyr Ser Ser Ile Gln Glu Arg Glu
225                 230                 235                 240

Lys Ile Ile Lys Thr Ile Glu Asn Cys Leu Glu Gln Arg Val Lys Arg
                245                 250                 255

Trp Lys Asp Ser Tyr Gln Trp Met Val Ser Asn Trp Leu Ser Arg Ile
            260                 265                 270

Thr Thr Gln Phe Asn His Ile Asn Tyr Gln Met Tyr Asp Ser Leu Ser
            275                 280                 285

Tyr Gln Ala Asp Ala Ile Lys Ala Lys Ile Asp Leu Glu Tyr Lys Lys
            290                 295                 300

Tyr Ser Gly Ser Asp Lys Glu Asn Ile Lys Ser Gln Val Glu Asn Leu
305                 310                 315                 320

Lys Asn Ser Leu Asp Val Lys Ile Ser Glu Ala Met Asn Asn Ile Asn
                325                 330                 335

Lys Phe Ile Arg Glu Cys Ser Val Thr Tyr Leu Phe Lys Asn Met Leu
            340                 345                 350

Pro Lys Val Ile Asp Glu Leu Asn Lys Phe Asp Leu Arg Thr Lys Thr
            355                 360                 365

Glu Leu Ile Asn Leu Ile Asp Ser His Asn Ile Ile Leu Val Gly Glu
            370                 375                 380

Val Asp
385

<210> SEQ ID NO 27
<211> LENGTH: 1149
<212> TYPE: DNA
<213> ORGANISM: Artificial Sequence
<220> FEATURE:
<223> OTHER INFORMATION: Synthetic Construct
<221> NAME/KEY: CDS
<222> LOCATION: (1)...(1146)

<400> SEQUENCE: 27 atg tcc atc tgc atc gag atc aac aac ggt gag ctg ttc ttc gtg gct     48
Met Ser Ile Cys Ile Glu Ile Asn Asn Gly Glu Leu Phe Phe Val Ala
 1               5                  10                  15 tcc gag aac agt tac aac gat gac aac atc aac act cct aag gag att     96
Ser Glu Asn Ser Tyr Asn Asp Asp Asn Ile Asn Thr Pro Lys Glu Ile
                20                  25                  30 gac gac acc gtc act tct aac aac aac tac gaa aac gac ctg gac cag    144
Asp Asp Thr Val Thr Ser Asn Asn Asn Tyr Glu Asn Asp Leu Asp Gln
            35                  40                  45 gtc atc cta aac ttc aac tcc gag tcc gcc cct ggt ctg tcc gac gag    192
Val Ile Leu Asn Phe Asn Ser Glu Ser Ala Pro Gly Leu Ser Asp Glu
        50                  55                  60 aag ctg aac ctg acc atc cag aac gac gct tac atc cca aag tac gac    240
Lys Leu Asn Leu Thr Ile Gln Asn Asp Ala Tyr Ile Pro Lys Tyr Asp
 65                  70                  75                  80 tcc aac ggt aca tcc gat atc gag cag cat gac gtt aac gag ctt aac    288
Ser Asn Gly Thr Ser Asp Ile Glu Gln His Asp Val Asn Glu Leu Asn
```

-continued

|  |  |  |  |  |  |  |  |  |  |  |  |  |  |  |  |
|---|---|---|---|---|---|---|---|---|---|---|---|---|---|---|---|
|  |  | 85 |  |  |  | 90 |  |  |  | 95 |  |  |  |  |  |

```
gtc ttc ttc tac tta gac gct cag aag gtg ccc gag ggt gag aac aac      336
Val Phe Phe Tyr Leu Asp Ala Gln Lys Val Pro Glu Gly Glu Asn Asn
            100                 105                 110 gtc aat ctc acc tct tca att gac aca gcc ttg ttg gag cag cct aag      384
Val Asn Leu Thr Ser Ser Ile Asp Thr Ala Leu Leu Glu Gln Pro Lys
            115                 120                 125 atc tac acc ttc ttc tcc tcc gag ttc atc aac aac gtc aac aag cct      432
Ile Tyr Thr Phe Phe Ser Ser Glu Phe Ile Asn Asn Val Asn Lys Pro
        130                 135                 140 gtg cag gcc gca ttg ttc gta agc tgg att cag cag gtg tta gta gac      480
Val Gln Ala Ala Leu Phe Val Ser Trp Ile Gln Gln Val Leu Val Asp
145                 150                 155                 160 ttc act act gag gct aac cag aag tcc act gtt gac aag atc gct gac      528
Phe Thr Thr Glu Ala Asn Gln Lys Ser Thr Val Asp Lys Ile Ala Asp
                165                 170                 175 atc tcc atc gtc gtc cca tac atc ggt ctg gct ctg aac atc ggc aac      576
Ile Ser Ile Val Val Pro Tyr Ile Gly Leu Ala Leu Asn Ile Gly Asn
            180                 185                 190 gag gca cag aag ggc aac ttc aag gat gcc ctt gag ttg ttg ggt gcc      624
Glu Ala Gln Lys Gly Asn Phe Lys Asp Ala Leu Glu Leu Leu Gly Ala
        195                 200                 205 ggt att ttg ttg gag ttc gaa ccc gag ctg ctg atc cct acc atc ctg      672
Gly Ile Leu Leu Glu Phe Glu Pro Glu Leu Leu Ile Pro Thr Ile Leu
    210                 215                 220 gtc ttc acg atc aag tcc ttc ctg ggt tcc tcc gac aac aag aac aag      720
Val Phe Thr Ile Lys Ser Phe Leu Gly Ser Ser Asp Asn Lys Asn Lys
225                 230                 235                 240 gtc att aag gcc atc aac aac gcc ctg aag gag cgt gac gag aag tgg      768
Val Ile Lys Ala Ile Asn Asn Ala Leu Lys Glu Arg Asp Glu Lys Trp
                245                 250                 255 aag gaa gtc tat tcc ttc atc gtc tcg aac tgg atg acc aag atc aac      816
Lys Glu Val Tyr Ser Phe Ile Val Ser Asn Trp Met Thr Lys Ile Asn
            260                 265                 270 acc cag ttc aac aag cga aag gag cag atg tac cag gct ctg cag aac      864
Thr Gln Phe Asn Lys Arg Lys Glu Gln Met Tyr Gln Ala Leu Gln Asn
        275                 280                 285 cag gtc aac gcc atc aag acc atc atc gag tcc aag tac aac tcc tac      912
Gln Val Asn Ala Ile Lys Thr Ile Ile Glu Ser Lys Tyr Asn Ser Tyr
    290                 295                 300 acc ctg gag gag aag aac gag ctt acc aac aag tac gat atc aag cag      960
Thr Leu Glu Glu Lys Asn Glu Leu Thr Asn Lys Tyr Asp Ile Lys Gln
305                 310                 315                 320 atc gag aac gag ctg aac cag aag gtc tcc atc gcc atg aac aac atc      1008
Ile Glu Asn Glu Leu Asn Gln Lys Val Ser Ile Ala Met Asn Asn Ile
                325                 330                 335 gac agg ttc ctg acc gag tcc tcc atc tcc tac ctg atg aag ctc atc      1056
Asp Arg Phe Leu Thr Glu Ser Ser Ile Ser Tyr Leu Met Lys Leu Ile
            340                 345                 350 aac gag gtc aag atc aac aag ctg cga gag tac gac gag aat gtc aag      1104
Asn Glu Val Lys Ile Asn Lys Leu Arg Glu Tyr Asp Glu Asn Val Lys
        355                 360                 365 acg tac ctg ctg aac tac atc atc cag cac gga tcc atc ctg              1146
Thr Tyr Leu Leu Asn Tyr Ile Ile Gln His Gly Ser Ile Leu
    370                 375                 380 taa                                                                  1149
```

<210> SEQ ID NO 28
<211> LENGTH: 382

```
<212> TYPE: PRT
<213> ORGANISM: Artificial Sequence
<220> FEATURE:
<223> OTHER INFORMATION: Synthetic Construct

<400> SEQUENCE: 28

Met Ser Ile Cys Ile Glu Ile Asn Asn Gly Glu Leu Phe Phe Val Ala
1               5                   10                  15

Ser Glu Asn Ser Tyr Asn Asp Asp Asn Ile Asn Thr Pro Lys Glu Ile
            20                  25                  30

Asp Asp Thr Val Thr Ser Asn Asn Asn Tyr Glu Asn Asp Leu Asp Gln
        35                  40                  45

Val Ile Leu Asn Phe Asn Ser Glu Ser Ala Pro Gly Leu Ser Asp Glu
    50                  55                  60

Lys Leu Asn Leu Thr Ile Gln Asn Asp Ala Tyr Ile Pro Lys Tyr Asp
65                  70                  75                  80

Ser Asn Gly Thr Ser Asp Ile Glu Gln His Asp Val Asn Glu Leu Asn
                85                  90                  95

Val Phe Phe Tyr Leu Asp Ala Gln Lys Val Pro Glu Gly Glu Asn Asn
            100                 105                 110

Val Asn Leu Thr Ser Ser Ile Asp Thr Ala Leu Leu Glu Gln Pro Lys
        115                 120                 125

Ile Tyr Thr Phe Phe Ser Ser Glu Phe Ile Asn Asn Val Asn Lys Pro
    130                 135                 140

Val Gln Ala Ala Leu Phe Val Ser Trp Ile Gln Gln Val Leu Val Asp
145                 150                 155                 160

Phe Thr Thr Glu Ala Asn Gln Lys Ser Thr Val Asp Lys Ile Ala Asp
                165                 170                 175

Ile Ser Ile Val Val Pro Tyr Ile Gly Leu Ala Leu Asn Ile Gly Asn
            180                 185                 190

Glu Ala Gln Lys Gly Asn Phe Lys Asp Ala Leu Glu Leu Leu Gly Ala
        195                 200                 205

Gly Ile Leu Leu Glu Phe Glu Pro Glu Leu Leu Ile Pro Thr Ile Leu
    210                 215                 220

Val Phe Thr Ile Lys Ser Phe Leu Gly Ser Ser Asp Asn Lys Asn Lys
225                 230                 235                 240

Val Ile Lys Ala Ile Asn Asn Ala Leu Lys Glu Arg Asp Glu Lys Trp
                245                 250                 255

Lys Glu Val Tyr Ser Phe Ile Val Ser Asn Trp Met Thr Lys Ile Asn
            260                 265                 270

Thr Gln Phe Asn Lys Arg Lys Glu Gln Met Tyr Gln Ala Leu Gln Asn
        275                 280                 285

Gln Val Asn Ala Ile Lys Thr Ile Ile Glu Ser Lys Tyr Asn Ser Tyr
    290                 295                 300

Thr Leu Glu Glu Lys Asn Glu Leu Thr Asn Lys Tyr Asp Ile Lys Gln
305                 310                 315                 320

Ile Glu Asn Glu Leu Asn Gln Lys Val Ser Ile Ala Met Asn Asn Ile
                325                 330                 335

Asp Arg Phe Leu Thr Glu Ser Ser Ile Ser Tyr Leu Met Lys Leu Ile
            340                 345                 350

Asn Glu Val Lys Ile Asn Lys Leu Arg Glu Tyr Asp Glu Asn Val Lys
        355                 360                 365

Thr Tyr Leu Leu Asn Tyr Ile Ile Gln His Gly Ser Ile Leu
    370                 375                 380
```

```
<210> SEQ ID NO 29
<211> LENGTH: 1227
<212> TYPE: DNA
<213> ORGANISM: Artificial Sequence
<220> FEATURE:
<223> OTHER INFORMATION: Synthetic Construct
<221> NAME/KEY: CDS
<222> LOCATION: (1)...(1224)

<400> SEQUENCE: 29 atg gcc cca cca cgt ctg tgt att aga gtc aac aac tca gaa tta ttc      48
Met Ala Pro Pro Arg Leu Cys Ile Arg Val Asn Asn Ser Glu Leu Phe
1               5                   10                  15 ttt gtc gct tcc gag tca agc tac aac gag aac gat att aac aca cct      96
Phe Val Ala Ser Glu Ser Ser Tyr Asn Glu Asn Asp Ile Asn Thr Pro
            20                  25                  30 aaa gag att gac gat act acc aac cta aac aac aac tac cgg aac aac     144
Lys Glu Ile Asp Asp Thr Thr Asn Leu Asn Asn Asn Tyr Arg Asn Asn
        35                  40                  45 ttg gat gag gtt att ttg gat tac aac tca cag acc atc cct caa att     192
Leu Asp Glu Val Ile Leu Asp Tyr Asn Ser Gln Thr Ile Pro Gln Ile
    50                  55                  60 tcc aac cgt acc tta aac act ctt gtc caa gac aac tcc tac gtt cca     240
Ser Asn Arg Thr Leu Asn Thr Leu Val Gln Asp Asn Ser Tyr Val Pro
65                  70                  75                  80 aga tac gat tct aac ggt acc tca gag atc gag gag tat gat gtt gtt     288
Arg Tyr Asp Ser Asn Gly Thr Ser Glu Ile Glu Glu Tyr Asp Val Val
                85                  90                  95 gac ttt aac gtc ttt ttc tat ttg cat gcc cag aag gtg cca gaa ggt     336
Asp Phe Asn Val Phe Phe Tyr Leu His Ala Gln Lys Val Pro Glu Gly
            100                 105                 110 gaa acc aac atc tca ttg act tct tcc att gat acc gcc ttg ttg gaa     384
Glu Thr Asn Ile Ser Leu Thr Ser Ser Ile Asp Thr Ala Leu Leu Glu
        115                 120                 125 gag tcc aag gat atc ttc ttt tct tcg gag ttt atc gat act atc aac     432
Glu Ser Lys Asp Ile Phe Phe Ser Ser Glu Phe Ile Asp Thr Ile Asn
    130                 135                 140 aag cct gtc aac gcc gct ctg ttc att gat tgg att agc aag gtc atc     480
Lys Pro Val Asn Ala Ala Leu Phe Ile Asp Trp Ile Ser Lys Val Ile
145                 150                 155                 160 aga gat ttt acc act gaa gct act caa aag tcc act gtt gat aag att     528
Arg Asp Phe Thr Thr Glu Ala Thr Gln Lys Ser Thr Val Asp Lys Ile
                165                 170                 175 gct gac atc tct ttg att gtc ccc tat gtc ggt ctt gct ttg aac atc     576
Ala Asp Ile Ser Leu Ile Val Pro Tyr Val Gly Leu Ala Leu Asn Ile
            180                 185                 190 att att gag gca gaa aag ggt aac ttt gag gag gct ttt gaa ttg ttg     624
Ile Ile Glu Ala Glu Lys Gly Asn Phe Glu Glu Ala Phe Glu Leu Leu
        195                 200                 205 gga gtt ggt att ttg ttg gag ttt gtt cca gaa ctt acc att cct gtc     672
Gly Val Gly Ile Leu Leu Glu Phe Val Pro Glu Leu Thr Ile Pro Val
    210                 215                 220 att tta gtt ttt acg atc aag tcc tac atc gat tca tac gag aac aag     720
Ile Leu Val Phe Thr Ile Lys Ser Tyr Ile Asp Ser Tyr Glu Asn Lys
225                 230                 235                 240 aat aaa gca att aaa gct att aac aac tcc ttg atc gaa aga gag gct     768
Asn Lys Ala Ile Lys Ala Ile Asn Asn Ser Leu Ile Glu Arg Glu Ala
                245                 250                 255 aag tgg aag gaa atc tac tca tgg att gta tca aac tgg ctt act aga     816
Lys Trp Lys Glu Ile Tyr Ser Trp Ile Val Ser Asn Trp Leu Thr Arg
            260                 265                 270
```

```
att aac act caa ttt aac aag aga aag gag caa atg tac cag gct ctg       864
Ile Asn Thr Gln Phe Asn Lys Arg Lys Glu Gln Met Tyr Gln Ala Leu
        275                 280                 285 caa aac caa gtc gat gct atc aag act gca att gaa tac aag tac aac       912
Gln Asn Gln Val Asp Ala Ile Lys Thr Ala Ile Glu Tyr Lys Tyr Asn
290                 295                 300 aac tat act tcc gat gag aag aac aga ctt gaa tct gaa tac aat atc       960
Asn Tyr Thr Ser Asp Glu Lys Asn Arg Leu Glu Ser Glu Tyr Asn Ile
305                 310                 315                 320 aac aac att gaa gaa gag ttg aac aag aaa gtt tct ttg gct atg aag      1008
Asn Asn Ile Glu Glu Glu Leu Asn Lys Lys Val Ser Leu Ala Met Lys
                325                 330                 335 aat atc gaa aga ttt atg acc gaa tcc tct atc tct tac ttg atg aag      1056
Asn Ile Glu Arg Phe Met Thr Glu Ser Ser Ile Ser Tyr Leu Met Lys
            340                 345                 350 ttg atc aat gag gcc aag gtt ggt aag ttg aag aag tac gat aac cac      1104
Leu Ile Asn Glu Ala Lys Val Gly Lys Leu Lys Lys Tyr Asp Asn His
        355                 360                 365 gtt aag agc gat ctg ctg aac tac att ctc gac cac aga tca atc ctg      1152
Val Lys Ser Asp Leu Leu Asn Tyr Ile Leu Asp His Arg Ser Ile Leu
370                 375                 380 gga gag cag aca aac gag ctg agt gat ttg gtt act tcc act ttg aac      1200
Gly Glu Gln Thr Asn Glu Leu Ser Asp Leu Val Thr Ser Thr Leu Asn
385                 390                 395                 400 tcc tcc att cca ttt gag ctt tct taa                                  1227
Ser Ser Ile Pro Phe Glu Leu Ser
                405
```

<210> SEQ ID NO 30
<211> LENGTH: 408
<212> TYPE: PRT
<213> ORGANISM: Artificial Sequence
<220> FEATURE:
<223> OTHER INFORMATION: Synthetic Construct

<400> SEQUENCE: 30

```
Met Ala Pro Pro Arg Leu Cys Ile Arg Val Asn Asn Ser Glu Leu Phe
1               5                   10                  15

Phe Val Ala Ser Glu Ser Ser Tyr Asn Glu Asn Asp Ile Asn Thr Pro
            20                  25                  30

Lys Glu Ile Asp Asp Thr Thr Asn Leu Asn Asn Asn Tyr Arg Asn Asn
        35                  40                  45

Leu Asp Glu Val Ile Leu Asp Tyr Asn Ser Gln Thr Ile Pro Gln Ile
    50                  55                  60

Ser Asn Arg Thr Leu Asn Thr Leu Val Gln Asp Asn Ser Tyr Val Pro
65                  70                  75                  80

Arg Tyr Asp Ser Asn Gly Thr Ser Glu Ile Glu Glu Tyr Asp Val Val
                85                  90                  95

Asp Phe Asn Val Phe Phe Tyr Leu His Ala Gln Lys Val Pro Glu Gly
            100                 105                 110

Glu Thr Asn Ile Ser Leu Thr Ser Ser Ile Asp Thr Ala Leu Leu Glu
        115                 120                 125

Glu Ser Lys Asp Ile Phe Phe Ser Ser Glu Phe Ile Asp Thr Ile Asn
    130                 135                 140

Lys Pro Val Asn Ala Ala Leu Phe Ile Asp Trp Ile Ser Lys Val Ile
145                 150                 155                 160

Arg Asp Phe Thr Thr Glu Ala Thr Gln Lys Ser Thr Val Asp Lys Ile
                165                 170                 175
```

```
Ala Asp Ile Ser Leu Ile Val Pro Tyr Val Gly Leu Ala Leu Asn Ile
            180                 185                 190

Ile Ile Glu Ala Glu Lys Gly Asn Phe Glu Glu Ala Phe Glu Leu Leu
            195                 200                 205

Gly Val Gly Ile Leu Glu Phe Val Pro Glu Leu Thr Ile Pro Val
            210                 215                 220

Ile Leu Val Phe Thr Ile Lys Ser Tyr Ile Asp Ser Tyr Glu Asn Lys
225                 230                 235                 240

Asn Lys Ala Ile Lys Ala Ile Asn Asn Ser Leu Ile Glu Arg Glu Ala
                245                 250                 255

Lys Trp Lys Glu Ile Tyr Ser Trp Ile Val Ser Asn Trp Leu Thr Arg
            260                 265                 270

Ile Asn Thr Gln Phe Asn Lys Arg Lys Glu Gln Met Tyr Gln Ala Leu
            275                 280                 285

Gln Asn Gln Val Asp Ala Ile Lys Thr Ala Ile Glu Tyr Lys Tyr Asn
            290                 295                 300

Asn Tyr Thr Ser Asp Glu Lys Asn Arg Leu Glu Ser Glu Tyr Asn Ile
305                 310                 315                 320

Asn Asn Ile Glu Glu Glu Leu Asn Lys Lys Val Ser Leu Ala Met Lys
                325                 330                 335

Asn Ile Glu Arg Phe Met Thr Glu Ser Ser Ile Ser Tyr Leu Met Lys
            340                 345                 350

Leu Ile Asn Glu Ala Lys Val Gly Lys Leu Lys Lys Tyr Asp Asn His
            355                 360                 365

Val Lys Ser Asp Leu Leu Asn Tyr Ile Leu Asp His Arg Ser Ile Leu
370                 375                 380

Gly Glu Gln Thr Asn Glu Leu Ser Asp Leu Val Thr Ser Thr Leu Asn
385                 390                 395                 400

Ser Ser Ile Pro Phe Glu Leu Ser
                405

<210> SEQ ID NO 31
<211> LENGTH: 1233
<212> TYPE: DNA
<213> ORGANISM: Artificial Sequence
<220> FEATURE:
<223> OTHER INFORMATION: Synthetic Construct
<221> NAME/KEY: CDS
<222> LOCATION: (1)...(1230)

<400> SEQUENCE: 31 atg gcc aaa aat acc ggt aaa tct gaa cag tgt att att gtt aat aat        48
Met Ala Lys Asn Thr Gly Lys Ser Glu Gln Cys Ile Ile Val Asn Asn
 1               5                  10                  15 gag gat tta ttt ttc ata gct aat aaa gat agt ttt tca aaa gat tta       96
Glu Asp Leu Phe Phe Ile Ala Asn Lys Asp Ser Phe Ser Lys Asp Leu
             20                  25                  30 gct aaa gca gaa act ata gca tat aat aca caa aat aat act ata gaa      144
Ala Lys Ala Glu Thr Ile Ala Tyr Asn Thr Gln Asn Asn Thr Ile Glu
         35                  40                  45 aat aat ttt tct ata gat cag ttg att tta gat aat gat tta agc agt      192
Asn Asn Phe Ser Ile Asp Gln Leu Ile Leu Asp Asn Asp Leu Ser Ser
     50                  55                  60 ggc ata gac tta cca aat gaa aac aca gaa cca ttt aca aat ttt gac      240
Gly Ile Asp Leu Pro Asn Glu Asn Thr Glu Pro Phe Thr Asn Phe Asp
 65                  70                  75                  80 gac ata gat atc cct gtg tat att aaa caa tct gct tta aaa aaa att      288
```

```
Asp Ile Asp Ile Pro Val Tyr Ile Lys Gln Ser Ala Leu Lys Lys Ile
                85                  90                  95 ttt gtg gat gga gat agc ctt ttt gaa tat tta cat gct caa aca ttt      336
Phe Val Asp Gly Asp Ser Leu Phe Glu Tyr Leu His Ala Gln Thr Phe
            100                 105                 110 cct tct aat ata gaa aat cta caa cta acg aat tca tta aat gat gct      384
Pro Ser Asn Ile Glu Asn Leu Gln Leu Thr Asn Ser Leu Asn Asp Ala
        115                 120                 125 tta aga aat aat aat aaa gtc tat act ttt ttt tct aca aac ctt gtt      432
Leu Arg Asn Asn Asn Lys Val Tyr Thr Phe Phe Ser Thr Asn Leu Val
130                 135                 140 gaa aaa gct aat aca gtt gta ggt gct tca ctt ttt gta aac tgg gta      480
Glu Lys Ala Asn Thr Val Val Gly Ala Ser Leu Phe Val Asn Trp Val
145                 150                 155                 160 aaa gga gta ata gat gat ttt aca tct gaa tcc aca caa aaa agt act      528
Lys Gly Val Ile Asp Asp Phe Thr Ser Glu Ser Thr Gln Lys Ser Thr
            165                 170                 175 ata gat aaa gtt tca gat gta tcc ata att att ccc tat ata gga cct      576
Ile Asp Lys Val Ser Asp Val Ser Ile Ile Ile Pro Tyr Ile Gly Pro
        180                 185                 190 gct ttg aat gta gga aat gaa aca gct aaa gaa aat ttt aaa aat gct      624
Ala Leu Asn Val Gly Asn Glu Thr Ala Lys Glu Asn Phe Lys Asn Ala
        195                 200                 205 ttt gaa ata ggt gga gcc gct atc tta atg gag ttt att cca gaa ctt      672
Phe Glu Ile Gly Gly Ala Ala Ile Leu Met Glu Phe Ile Pro Glu Leu
210                 215                 220 att gta cct ata gtt gga ttt ttt aca tta gaa tca tat gta gga aat      720
Ile Val Pro Ile Val Gly Phe Phe Thr Leu Glu Ser Tyr Val Gly Asn
225                 230                 235                 240 aaa ggg cat att att atg acg ata tcc aat gct tta aag aaa agg gat      768
Lys Gly His Ile Ile Met Thr Ile Ser Asn Ala Leu Lys Lys Arg Asp
            245                 250                 255 caa aaa tgg aca gat atg tat ggt ttg ata gta tcg cag tgg ctc tca      816
Gln Lys Trp Thr Asp Met Tyr Gly Leu Ile Val Ser Gln Trp Leu Ser
        260                 265                 270 acg gtt aat act caa ttt tat aca ata aaa gaa aga atg tac aat gct      864
Thr Val Asn Thr Gln Phe Tyr Thr Ile Lys Glu Arg Met Tyr Asn Ala
        275                 280                 285 tta aat aat caa tca caa gca ata gaa aaa ata ata gaa gat caa tat      912
Leu Asn Asn Gln Ser Gln Ala Ile Glu Lys Ile Ile Glu Asp Gln Tyr
290                 295                 300 aat aga tat agt gaa gaa gat aaa atg aat att aac att gat ttt aat      960
Asn Arg Tyr Ser Glu Glu Asp Lys Met Asn Ile Asn Ile Asp Phe Asn
305                 310                 315                 320 gat ata gat ttt aaa ctt aat caa agt ata aat tta gca ata aac aat     1008
Asp Ile Asp Phe Lys Leu Asn Gln Ser Ile Asn Leu Ala Ile Asn Asn
            325                 330                 335 ata gat gat ttt ata aac caa tgt tct ata tca tat cta atg aat aga     1056
Ile Asp Asp Phe Ile Asn Gln Cys Ser Ile Ser Tyr Leu Met Asn Arg
        340                 345                 350 atg att cca tta gct gta aaa aag tta aaa gac ttt gat gat aat ctt     1104
Met Ile Pro Leu Ala Val Lys Lys Leu Lys Asp Phe Asp Asp Asn Leu
        355                 360                 365 aag aga gat tta ttg gag tat ata gat aca aat gaa cta tat tta ctt     1152
Lys Arg Asp Leu Leu Glu Tyr Ile Asp Thr Asn Glu Leu Tyr Leu Leu
370                 375                 380 gat gaa gta aat att cta aaa tca aaa gta aat aga cac cta aaa gac     1200
Asp Glu Val Asn Ile Leu Lys Ser Lys Val Asn Arg His Leu Lys Asp
385                 390                 395                 400
```

```
agt ata cca ttt gat ctt tca cta tat acc taa                              1233
Ser Ile Pro Phe Asp Leu Ser Leu Tyr Thr
            405                 410
```

<210> SEQ ID NO 32
<211> LENGTH: 410
<212> TYPE: PRT
<213> ORGANISM: Artificial Sequence
<220> FEATURE:
<223> OTHER INFORMATION: Synthetic Construct

<400> SEQUENCE: 32

```
Met Ala Lys Asn Thr Gly Lys Ser Glu Gln Cys Ile Ile Val Asn Asn
  1               5                  10                  15

Glu Asp Leu Phe Phe Ile Ala Asn Lys Asp Ser Phe Ser Lys Asp Leu
             20                  25                  30

Ala Lys Ala Glu Thr Ile Ala Tyr Asn Thr Gln Asn Asn Thr Ile Glu
         35                  40                  45

Asn Asn Phe Ser Ile Asp Gln Leu Ile Leu Asp Asn Asp Leu Ser Ser
 50                  55                  60

Gly Ile Asp Leu Pro Asn Glu Asn Thr Glu Pro Phe Thr Asn Phe Asp
 65                  70                  75                  80

Asp Ile Asp Ile Pro Val Tyr Ile Lys Gln Ser Ala Leu Lys Lys Ile
                 85                  90                  95

Phe Val Asp Gly Asp Ser Leu Phe Glu Tyr Leu His Ala Gln Thr Phe
            100                 105                 110

Pro Ser Asn Ile Glu Asn Leu Gln Leu Thr Asn Ser Leu Asn Asp Ala
        115                 120                 125

Leu Arg Asn Asn Asn Lys Val Tyr Thr Phe Phe Ser Thr Asn Leu Val
130                 135                 140

Glu Lys Ala Asn Thr Val Val Gly Ala Ser Leu Phe Val Asn Trp Val
145                 150                 155                 160

Lys Gly Val Ile Asp Asp Phe Thr Ser Glu Ser Thr Gln Lys Ser Thr
                165                 170                 175

Ile Asp Lys Val Ser Asp Val Ser Ile Ile Pro Tyr Ile Gly Pro
            180                 185                 190

Ala Leu Asn Val Gly Asn Glu Thr Ala Lys Glu Asn Phe Lys Asn Ala
        195                 200                 205

Phe Glu Ile Gly Gly Ala Ala Ile Leu Met Glu Phe Ile Pro Glu Leu
    210                 215                 220

Ile Val Pro Ile Val Gly Phe Phe Thr Leu Glu Ser Tyr Val Gly Asn
225                 230                 235                 240

Lys Gly His Ile Ile Met Thr Ile Ser Asn Ala Leu Lys Lys Arg Asp
                245                 250                 255

Gln Lys Trp Thr Asp Met Tyr Gly Leu Ile Val Ser Gln Trp Leu Ser
            260                 265                 270

Thr Val Asn Thr Gln Phe Tyr Thr Ile Lys Glu Arg Met Tyr Asn Ala
        275                 280                 285

Leu Asn Asn Gln Ser Gln Ala Ile Glu Lys Ile Ile Glu Asp Gln Tyr
    290                 295                 300

Asn Arg Tyr Ser Glu Glu Asp Lys Met Asn Ile Asn Ile Asp Phe Asn
305                 310                 315                 320

Asp Ile Asp Phe Lys Leu Asn Gln Ser Ile Asn Leu Ala Ile Asn Asn
                325                 330                 335

Ile Asp Asp Phe Ile Asn Gln Cys Ser Ile Ser Tyr Leu Met Asn Arg
            340                 345                 350
```

```
Met Ile Pro Leu Ala Val Lys Lys Leu Lys Asp Phe Asp Asp Asn Leu
            355                 360                 365

Lys Arg Asp Leu Leu Glu Tyr Ile Asp Thr Asn Glu Leu Tyr Leu Leu
    370                 375                 380

Asp Glu Val Asn Ile Leu Lys Ser Lys Val Asn Arg His Leu Lys Asp
385                 390                 395                 400

Ser Ile Pro Phe Asp Leu Ser Leu Tyr Thr
            405                 410

<210> SEQ ID NO 33
<211> LENGTH: 1314
<212> TYPE: DNA
<213> ORGANISM: Artificial Sequence
<220> FEATURE:
<223> OTHER INFORMATION: Synthetic Construct
<221> NAME/KEY: CDS
<222> LOCATION: (10)...(1305)

<400> SEQUENCE: 33 gaattcacg atg tct tac act aac gac aaa atc ctg atc ctg tac ttc aac      51
          Met Ser Tyr Thr Asn Asp Lys Ile Leu Ile Leu Tyr Phe Asn
            1               5                  10 aaa ctg tac aaa aaa atc aaa gac aac tct atc ctg gac atg cgt tac        99
Lys Leu Tyr Lys Lys Ile Lys Asp Asn Ser Ile Leu Asp Met Arg Tyr
 15                  20                  25                  30 gaa aac aac aaa ttc atc gac atc tct ggc tat ggt tct aac atc tct       147
Glu Asn Asn Lys Phe Ile Asp Ile Ser Gly Tyr Gly Ser Asn Ile Ser
                 35                  40                  45 atc aac ggt gac gtc tac atc tac tct act aac cgc aac cag ttc ggt       195
Ile Asn Gly Asp Val Tyr Ile Tyr Ser Thr Asn Arg Asn Gln Phe Gly
             50                  55                  60 atc tac tct tct aaa ccg tct gaa gta aac atc gct cag aac aac gac       243
Ile Tyr Ser Ser Lys Pro Ser Glu Val Asn Ile Ala Gln Asn Asn Asp
         65                  70                  75 atc atc tac aac ggt cgt tac cag aac ttc tct atc tct ttc tgg gtt       291
Ile Ile Tyr Asn Gly Arg Tyr Gln Asn Phe Ser Ile Ser Phe Trp Val
     80                  85                  90 cgt atc ccg aaa tac ttc aac aaa gtt aac ctg aac aac gaa tac act       339
Arg Ile Pro Lys Tyr Phe Asn Lys Val Asn Leu Asn Asn Glu Tyr Thr
 95                 100                 105                 110 atc atc gac tgc atc cgt aac aac aac tct ggt tgg aaa atc tct ctg       387
Ile Ile Asp Cys Ile Arg Asn Asn Asn Ser Gly Trp Lys Ile Ser Leu
                115                 120                 125 aac tac aac aaa atc atc tgg act ctg cag gac act gct ggt aac aac       435
Asn Tyr Asn Lys Ile Ile Trp Thr Leu Gln Asp Thr Ala Gly Asn Asn
            130                 135                 140 cag aaa ctg gtt ttc aac tac act cag atg atc tct atc tct gac tac       483
Gln Lys Leu Val Phe Asn Tyr Thr Gln Met Ile Ser Ile Ser Asp Tyr
        145                 150                 155 att aat aaa tgg atc ttc gtt act atc act aac aac cgt ctg ggt aac       531
Ile Asn Lys Trp Ile Phe Val Thr Ile Thr Asn Asn Arg Leu Gly Asn
    160                 165                 170 tct cgt atc tac atc aac ggt aac ctg atc gat gaa aaa tct atc tct       579
Ser Arg Ile Tyr Ile Asn Gly Asn Leu Ile Asp Glu Lys Ser Ile Ser
175                 180                 185                 190 aac ctg ggt gac atc cac gtt tct gac aac atc ctg ttc aaa atc gtt       627
Asn Leu Gly Asp Ile His Val Ser Asp Asn Ile Leu Phe Lys Ile Val
                195                 200                 205 ggt tgc aac gac acg cgt tac gtt ggt atc cgt tac ttc aaa gtt ttc       675
Gly Cys Asn Asp Thr Arg Tyr Val Gly Ile Arg Tyr Phe Lys Val Phe
```

```
                  210                 215                 220
gac act gaa ctg ggt aaa act gaa atc gaa act ctg tac tct gac gaa       723
Asp Thr Glu Leu Gly Lys Thr Glu Ile Glu Thr Leu Tyr Ser Asp Glu
        225                 230                 235 ccg gac ccg tct atc ctg aaa gac ttc tgg ggt aac tac ctg ctg tac       771
Pro Asp Pro Ser Ile Leu Lys Asp Phe Trp Gly Asn Tyr Leu Leu Tyr
240                 245                 250 aac aaa cgt tac tac ctg ctg aac ctc cgg act gac aaa tct atc           819
Asn Lys Arg Tyr Tyr Leu Leu Asn Leu Leu Arg Thr Asp Lys Ser Ile
255                 260                 265                 270 act cag aac tct aac ttc ctg aac atc aac cag cag cgt ggt gtt tat       867
Thr Gln Asn Ser Asn Phe Leu Asn Ile Asn Gln Gln Arg Gly Val Tyr
                275                 280                 285 cag aaa cct aat atc ttc tct aac act cgt ctg tac act ggt gtt gaa       915
Gln Lys Pro Asn Ile Phe Ser Asn Thr Arg Leu Tyr Thr Gly Val Glu
                290                 295                 300 gtt atc atc cgt aaa aac ggt tct act gac atc tct aac act gac aac       963
Val Ile Ile Arg Lys Asn Gly Ser Thr Asp Ile Ser Asn Thr Asp Asn
            305                 310                 315 ttc gta cgt aaa aac gac ctg gct tac atc aac gtt gtt gac cgt gac      1011
Phe Val Arg Lys Asn Asp Leu Ala Tyr Ile Asn Val Val Asp Arg Asp
        320                 325                 330 gtt gaa tac cgt ctg tac gct gac atc tct atc gct aaa ccg gaa aaa      1059
Val Glu Tyr Arg Leu Tyr Ala Asp Ile Ser Ile Ala Lys Pro Glu Lys
335                 340                 345                 350 atc atc aaa ctg atc cgt act tct aac tct aac aac tct ctg ggt cag      1107
Ile Ile Lys Leu Ile Arg Thr Ser Asn Ser Asn Asn Ser Leu Gly Gln
                355                 360                 365 atc atc gtt atg gac tcg atc ggt aac aac tgc act atg aac ttc cag      1155
Ile Ile Val Met Asp Ser Ile Gly Asn Asn Cys Thr Met Asn Phe Gln
                370                 375                 380 aac aac aac ggt ggt aac atc ggt ctg ctg ggt ttc cac tct aac aac      1203
Asn Asn Asn Gly Gly Asn Ile Gly Leu Leu Gly Phe His Ser Asn Asn
            385                 390                 395 ctg gtt gct tct tca tgg tac tac aac aac atc cgt aaa aac act tct      1251
Leu Val Ala Ser Ser Trp Tyr Tyr Asn Asn Ile Arg Lys Asn Thr Ser
        400                 405                 410 tct aac ggt tgc ttc tgg tct ttc atc tct aaa gaa cac ggt tgg cag      1299
Ser Asn Gly Cys Phe Trp Ser Phe Ile Ser Lys Glu His Gly Trp Gln
415                 420                 425                 430 gaa aac taagaattc                                                    1314
Glu Asn
```

<210> SEQ ID NO 34
<211> LENGTH: 432
<212> TYPE: PRT
<213> ORGANISM: Artificial Sequence
<220> FEATURE:
<223> OTHER INFORMATION: Synthetic Construct

<400> SEQUENCE: 34

```
Met Ser Tyr Thr Asn Asp Lys Ile Leu Ile Leu Tyr Phe Asn Lys Leu
1               5                   10                  15

Tyr Lys Lys Ile Lys Asp Asn Ser Ile Leu Asp Met Arg Tyr Glu Asn
                20                  25                  30

Asn Lys Phe Ile Asp Ile Ser Gly Tyr Gly Ser Asn Ile Ser Ile Asn
            35                  40                  45

Gly Asp Val Tyr Ile Tyr Ser Thr Asn Arg Asn Gln Phe Gly Ile Tyr
        50                  55                  60
```

-continued

| | | | | | | | | | | | | | | | |
|---|---|---|---|---|---|---|---|---|---|---|---|---|---|---|---|
|Ser|Ser|Lys|Pro|Ser|Glu|Val|Asn|Ile|Ala|Gln|Asn|Asn|Asp|Ile|Ile|
|65| | | | |70| | | |75| | | | |80| |

Tyr Asn Gly Arg Tyr Gln Asn Phe Ser Ile Ser Phe Trp Val Arg Ile
                85                  90                  95

Pro Lys Tyr Phe Asn Lys Val Asn Leu Asn Asn Glu Tyr Thr Ile Ile
            100                 105                 110

Asp Cys Ile Arg Asn Asn Asn Ser Gly Trp Lys Ile Ser Leu Asn Tyr
        115                 120                 125

Asn Lys Ile Ile Trp Thr Leu Gln Asp Thr Ala Gly Asn Asn Gln Lys
    130                 135                 140

Leu Val Phe Asn Tyr Thr Gln Met Ile Ser Ile Ser Asp Tyr Ile Asn
145                 150                 155                 160

Lys Trp Ile Phe Val Thr Ile Thr Asn Asn Arg Leu Gly Asn Ser Arg
                165                 170                 175

Ile Tyr Ile Asn Gly Asn Leu Ile Asp Glu Lys Ser Ile Ser Asn Leu
            180                 185                 190

Gly Asp Ile His Val Ser Asp Asn Ile Leu Phe Lys Ile Val Gly Cys
        195                 200                 205

Asn Asp Thr Arg Tyr Val Gly Ile Arg Tyr Phe Lys Val Phe Asp Thr
    210                 215                 220

Glu Leu Gly Lys Thr Glu Ile Glu Thr Leu Tyr Ser Asp Glu Pro Asp
225                 230                 235                 240

Pro Ser Ile Leu Lys Asp Phe Trp Gly Asn Tyr Leu Leu Tyr Asn Lys
                245                 250                 255

Arg Tyr Tyr Leu Leu Asn Leu Leu Arg Thr Asp Lys Ser Ile Thr Gln
            260                 265                 270

Asn Ser Asn Phe Leu Asn Ile Asn Gln Gln Arg Gly Val Tyr Gln Lys
        275                 280                 285

Pro Asn Ile Phe Ser Asn Thr Arg Leu Tyr Thr Gly Val Glu Val Ile
    290                 295                 300

Ile Arg Lys Asn Gly Ser Thr Asp Ile Ser Asn Thr Asp Asn Phe Val
305                 310                 315                 320

Arg Lys Asn Asp Leu Ala Tyr Ile Asn Val Val Asp Arg Asp Val Glu
                325                 330                 335

Tyr Arg Leu Tyr Ala Asp Ile Ser Ile Ala Lys Pro Glu Lys Ile Ile
            340                 345                 350

Lys Leu Ile Arg Thr Ser Asn Ser Asn Asn Ser Leu Gly Gln Ile Ile
        355                 360                 365

Val Met Asp Ser Ile Gly Asn Asn Cys Thr Met Asn Phe Gln Asn Asn
    370                 375                 380

Asn Gly Gly Asn Ile Gly Leu Leu Gly Phe His Ser Asn Asn Leu Val
385                 390                 395                 400

Ala Ser Ser Trp Tyr Tyr Asn Asn Ile Arg Lys Asn Thr Ser Ser Asn
                405                 410                 415

Gly Cys Phe Trp Ser Phe Ile Ser Lys Glu His Gly Trp Gln Glu Asn
            420                 425                 430

RECOMBINANT VACCINE AGAINST BOTULINUM NEUROTOXIN

This application is a continuation of U.S. application Ser. No. 09/611,419 filed Jul. 6, 2000 (pending) which is a continuation-in-part of U.S. patent application Ser. No. 08/123,975, filed Sep. 21, 1993 (abandoned), and a continuation of International Application No. PCT/US00/12890, which claims the benefit of U.S. Provisional Applications Nos. 60/133,866, 60/133,868, 60/133,869, 60/133,865, 60/133,873, and 60/133,867, all filed May 12, 1999, U.S. Provisional Application No. 60/146,192, filed Jul. 29, 1999, all of which are incorporated herein by reference in their entirety.

BACKGROUND OF THE INVENTION

1. Field of the Invention

This invention is directed to preparation and expression of synthetic genes encoding polypeptides containing protective epitopes of botulinum neurotoxin (BoNT). The invention is also directed to methods of vaccination against botulism using the expressed peptides.

2. Related Art

The sporulating, obligate anaerobic, gram-positive *bacillus Clostridium* produces eight forms of antigenically distinct exotoxins. Tetanus neurotoxin (TeNT) is produced by *Clostridium tetani* while *Clostridium botulinum* produces seven different neurotoxins which are differentiated serologically by specific neutralization. The botulinum neurotoxins (BoNT) have been designated as serotypes A, B, $C_1$, D, E, F, and G. Botulinum neurotoxins (BoNT) are the most toxic substances known and are the causative agents of the disease botulism. BoNT exert their action by inhibiting the release of the neurotransmitter acetylcholine at the neuromuscular junction (Habermann, E., et al., (1986), "Clostridial Neurotoxins: Handling and Action at the Cellular and Molecular Level," *Cur. Top. Microbiol. Immunol.*, 129:93–179; Schiavo, G., et al., (1992a), "Tetanus and Botulinum-B Neurotoxins Block Neurotransmitter Release by Proteolytic Cleavage of Synaptobrevin," *Nature*, 359: 832–835; Simpson, L. L., (1986), "Molecular Pharmacology of Botulinum Toxin and Tetanus Toxin," *Annu. Rev. Pharmacol. Toxicol.*, 26:427–453) which leads to a state of flaccid paralysis. Indeed, only a few molecules of toxin can abolish the action of a nerve cell. Polyclonal antibodies derived for a specific neurotoxin can neutralize the toxic effects of that toxin but will not cross-neutralize another toxin serotype. Thus, to protect against all seven toxins, one needs seven vaccines.

Botulinum neurotoxins are translated as a single 150 kDa polypeptide chain and then posttranslationally nicked, forming a dichain consisting of a 100 kDa heavy chain and a 50 kDa light chain which remain linked by a disulfide bond (DasGupta, B. R., et al., (1972), "A Common Subunit Structure in *Clostridium botulinum* Type A, B, and E Toxins," *Biophys. Res. Commun.*, 48:108–112; DasGupta, B. R., (1989), "The Structure of Botulinum Neurotoxins," *Botulinum Neurotoxin and Tetanus Toxin*, (Simpson, L. L., Ed.), pp. 53–67, Academic Press, New York). Most of the clostridial strains contain specific endogenous proteases which activate the toxins at a protease-sensitive loop located approximately one third of the way into the molecule from the amino-terminal end. Upon reduction and fractionation (electrophoretically or chromatographically), the two chains can be separated; one chain has a Mr of ~100 kDa and is referred to as the heavy chain while the other has a Mr ~50 kDa and is termed the light chain.

The mechanism of nerve intoxication is accomplished through the interplay of three key events, each of which is performed by a separate portion of the neurotoxin protein. First, the carboxy half of the heavy chain (fragment C or $H_C$ is required for receptor specific binding to cholinergic nerve cells (Black, J. D., et al., (1986), "Interaction of $^{125}$I-botulinum Neurotoxins with Nerve Terminals. I. Ultrastructural Autoradiographic Localization and Quantitation of Distinct Membrane Acceptors for Types A and B on Motor Nerves," *J. Cell Biol.*, 103:521–534; Nishiki, T.-I., et al., (1994), "Identification of Protein Receptor for *Clostridium botulinum* Type B Neurotoxin in Rat Brain Synaptosomes," *J. Biol. Chem.*, 269:10498–10503; Shone, C. C., et al., (1985), "Inactivation of *Clostridium botulinum* Type A Neurotoxin by Trypsin and Purification of Two Tryptic Fragments. Proteolytic Action Near the COOH-terminus of the Heavy Subunit Destroys Toxin-Binding Activity, *Eur. J. Biochem.*, 151:75–82). There is evidence suggesting that polysialogangliosides (van Heyningen, W. E., (1968), "Tetanus," *Sci. Am.*, 218:69–77) could act as receptors for the toxins but the data supporting a specific receptor remains equivocal (Middlebrook, J. L., (1989), "Cell Surface Receptors for Protein Toxins," *Botulinum Neurotoxins and Tetanus Toxin*, (Simpson, L. L., Ed.) pp. 95–119, Academic Press, New York). After binding, the toxin is internalized into an endosome through receptor-mediated endocyctosis (Shone, C. C., et al., (1987), "A 50-kDa Fragment from the $NH_2$-tenninus of the Heavy Subunit of *Clostridium botulinum* Type A Neurotoxin Forms Channels in Lipid Vesicles, *Euro. J. Biochem.*, 167:175–180). The amino terminal half of the heavy chain is believed to participate in the translocation mechanism of the light chain across the endosomal membrane (Simpson, 1986; Poulain, B., et al., (1991), "Heterologous Combinations of Heavy and Light Chains from Botulinum Neurotoxin A and Tetanus Toxin Inhibit Neurotransmitter Release in *Aplysia*," *J. Biol. Chem.*, 266: 9580–9585; Montal, M. S., et al., (1992), "Identification of an Ion Channel-Forming Motif in the Primary Structure of Tetanus and Botulinum Neurotoxins," *FEBS*, 313:12–18). The low pH environment of the endosome may trigger a conformational change in the translocation domain, thus forming a channel for the light chain The final event of intoxication involves enzymatic activity of the light chain, a zinc-dependent endoprotease (Schiavo, 1992a; Schiavo, G., et al., (1992b), "Tetanus Toxin is a Zinc Protein and its Inhibition of Neurotransmitter Release and Protease Activity Depend on Zinc," *EMBO J.*, 11:3577–3583), on key synaptic vesicle proteins (Schiavo, 1992a; Oguma, K., et al., (1995), "Structure and Function of *Clostridium botulinum* Toxins," *Microbiol. Immunol.*, 39:161–168; Schiavo, G., et al., (1993), "Identification of the Nerve Terminal Targets of Botulinum Neurotoxin Serotypes A, D, and E," *J. Biol. Chem.*, 268:23784–23787; Shone, C. C., et al., (1993), "Proteolytic Cleavage of Synthetic Fragments of Vesicle-Associated Membrane Protein, Isoform-2 by Botulinum Type B Neurotoxin," *Eur. J. Biochem.*, 217:965–971) necessary for neurotransmitter release. The light chains of BoNT serotypes A, $C_1$, and E cleave SNAP-25 (synaptosomal-associated protein of M25,000), serotypes B, D, F, and G cleave VAMP/synaptobrevin (synaptic vesicle-associated membrane protein); and serotype $C_1$ cleaves syntaxin. Inactivation of SNAP-25, VAMP, or syntaxin by BoNT leads to an inability of the nerve cells to release acetylcholine resulting in neuromuscular paralysis and possible death, if the condition remains untreated.

Human botulism poisoning is generally caused by type A, B, E or rarely, by type F toxin. Type A and B are highly poisonous proteins which resist digestion by the enzymes of the gastrointestinal tract. Foodborne botulism poisoning is caused by the toxins present in contaminated food, but wound and infant botulism are caused by in vivo growth in closed wounds and the gastrointestinal tract respectively. The toxins primarily act by inhibiting the neurotransmitter acetylcholine at the neuromuscular junction, causing paralysis. Another means for botulism poisoning to occur is the deliberate introduction of the toxin(s) into the environment as might occur in biological warfare. When the cause of botulism is produced by toxin rather than by in vivo infection the onset of neurologic symptoms is usually abrupt and occurs within 18 to 36 hours after ingestion. The most common immediate cause of death in respiratory failure due to diaphragmatic paralysis. Home canned foods are the most common sources of toxins. The most frequently implicated toxin is toxin A, which is responsible for more than 50% of morbidity resulting from botulinum toxin.

Because even small amounts of botulinal toxin can cause serious illness, persons such as laboratory workers who are exposed to toxin must learn to handle all samples that may contain toxin with extreme care. It is also suggested that such workers be protected from illness by vaccination against the toxins. Furthermore, persons exposed to conditions in which botulism toxins might be in the environment which might be inhaled or ingested, such as military personnel, need to be protected from the toxin.

Agents that abolish the action of BoNT have been investigated since the 1940s. Early work at Fort Detrick in the 1940s lead to the development of a toxoid vaccine to protect against serotypes A, B, $C_1$, D, and E toxins. The toxoid vaccine was manufactured by growing five *Clostridium botulinum* strains, extracting and precipitating the toxin from the growth media after cell lysis. Formalin was added to the crude preparation to inactivate the neurotoxin. Residual formalin was left in the vaccine product to ensure the toxin remains non-toxic. The product was adsorbed to aluminum hydroxide and blended. Currently, a pentavalent toxoid vaccine against serotypes A through E (Anderson, J. H., et al., (1981), "Clinical Evaluation of Botulinum Toxoids," *Biomedical Aspects of Botulism,* (Lewis, G. E., Ed.), pp. 233–246, Academic Press, New York; Ellis, R. J., (1982), "Immunobiologic Agents and Drugs Available from the Centers for Disease Control. Descriptions, Recommendations, Adverse Reactions and Scrologic Response," 3rd ed., Centers for Disease Control. Atlanta, Ga.; Fiock, M. A., et al., (1963), "Studies of Immunities to Toxins of *Clostridium Botulinum*. IX. Immunologic Response of Man to Purified Pentavalent ABCDE Botulinum Toxoid," *J. Immunol.,* 90:697–702; Siegel, L. S., (1988), "Human Immune Response to Botulinum Pentavalent (ABCDE) Toxoid Determined by a Neutralization Test and by an Enzyme-Linked Immunosorbent Assay," *J. Clin. Microbiol.,* 26:2351–2356), available under Investigational New Drug (IND) status, is used to immunize specific populations of at-risk individuals, i.e., scientists and health care providers who handle BoNT and our armed forces who may be subjected to weaponized forms of the toxin Though serotypes A, B, and E are most associated with botulism outbreaks in humans, type F has also been diagnosed (Midura, T. F., et al., (1972), "*Clostridium botulinum* Type F: Isolation from Venison Jerky," Appl. Microbiol., 24:165–167; Green, J., et al., (1983), "Human Botulism (Type F)—A Rare Type," *Am. J. Med.,* 75:893–895; Sonnabend, W. F., et al., (1987), "Intestinal Toxicoinfection by *Clostridium botulinum* Type F in an Adult. Case Associated with Guillian-Barre Syndrome," *Lancet,* 1:357–361; Hatheway, C. L., (1976), "Toxoid of *Clostridium botulinum* Type F: Purification and Immunogenicity Studies," *Appl. Environ. Microbiol.,* 31:234–242). A separate monovalent toxoid vaccine against BoNTF is available under IND status Hatheway demonstrated that the BoNTF toxoid could protect guinea pigs against a homologous challenge (Wadsworth, J. D. F., et al., (1990), "Botulinum Type F Neurotoxin," *Biochem. J.,* 268:123–128).

Even though toxoid vaccines are available, there are numerous shortcomings with their current use and ease of production. First, because *C. botulinum* is a spore-former, a dedicated facility is required to manufacture a toxin-based product. The requirement for a dedicated manufacturing facility is not trivial. It is extremely costly to renovate and upgrade an existing facility or to build a new one and then to maintain the facility in accordance with current Good Manufacturing Practices (cGMP) to manufacture one vaccine. Second, the yields of toxin production from *C. botulinum* are relatively low. Third, the toxoiding process involves handling large quantities of toxin and thus is dangerous, and the added safety precautions increase the cost of manufacturing. Fourth, the toxoid product for types A–E consists of a crude extract of clostridial proteins that may influence immunogenicity or reactivity of the vaccine, and the type F toxoid is only partially purified (IND 5077). Fifth, because the toxoiding process involves the use of formaldehyde, which inactivates the toxin, and residual levels of formaldehyde (not to exceed 0.02%) are part of the product formulation to prevent reactivation of the toxin, the vaccine is reactogenic. An additional component of the toxoid vaccines is the preservative thimerosal (0.01%), which also increases the reactogenicity of the product.

The development of a new-generation, recombinant vaccine could alleviate many of the problems associated with the toxoid. A recombinant vaccine would eliminate the need for a dedicated manufacturing facility. Presently, many cgMP facilities are in existence and available that could manufacture a recombinant product. There would be no need to culture large quantities of a hazardous toxin-producing bacterium. Production yields from a genetically engineered product is expected to be high. There would be no need to treat the vaccine with formalin because the product would be non-toxic from the outset. Recombinant products would be purer, less reactogenic, and more fully characterized. Thus, the cost of a recombinant product would be expected to be much lower than a toxoid because there would be no expenditures required to support a dedicated facility, and the higher production yields would reduce the cost of the vaccine product.

SUMMARY OF THE INVENTION

The instant invention provides immunogenic peptides capable of eliciting protective immunity against botulinum neurotoxin of serotypes A–G.

The instant invention also provides vaccines capable of eliciting protective immunity against botulinum neurotoxin, where the vaccines do not act as neurotoxins themselves.

The instant invention further provides methods for preparing non-toxic peptides for use in vaccines against botulinum neurotoxin by growing recombinant organisms which express the peptides.

The instant invention also provides methods for fast and efficient purification of the non-toxic peptides from cultures of recombinant organisms.

These and other aspects are illustrated by one or more of the following embodiments of the present invention.

In one embodiment, this invention provides a nucleic acid encoding the carboxy-terminal portion of the heavy chain (HC) of botulinum neurotoxin (BoNT), the BoNT being selected from the group consisting of BoNT serotype A, BoNT serotype B, BoNT serotype C1, BoNT serotype D, BoNT serotype E, BoNT serotype F, and BoNT serotype G, wherein said nucleic acid is expressable in a recombinant organism selected from *Escherichia coli* and *Pichia pastoris*. Preferably, the nucleic acid comprises a nucleic acid sequence selected from SEQ ID No:1 (serotype A), SEQ ID No:7 (serotype B), SEQ ID No:9 (serotype Cl), SEQ ID No:1 (serotype D), SEQ ID No:13 (serotpye E), SEQ ID No:15 (serotype F), and SEQ ID No:17 (serotype G). In an alternative preferred embodiment, the nucleic acid encodes an HC amino acid sequence of BoNT selected from SEQ ID No:2 (serotype A), SEQ ID No:8 (serotype B), SEQ ID No:10 (serotype Cl), SEQ ID No:12 (serotype D), SEQ ID No:14 (serotpye E), SEQ ID No:16 (serotype F), and SEQ ID No:18 (serotype G).

In another embodiment, this invention provides a nucleic acid encoding the amino-terminal portion of the heavy chain (HN) of botulinum neurotoxin (BoNT), the BoNT being selected from the group consisting of BoNT serotype B, BoNT serotype C1, BoNT serotype D, BoNT serotype E, BoNT serotype F, and BoNT serotype G, wherein said nucleic acid is expressable in a recombinant organism selected from *Escherichia coli* and *Pichia pastoris*. In a prefered embodiment, the nucleic acid comprises a nucleic acid sequence selected from SEQ ID No:21 (serotype B), SEQ ID No:23 (serotype C1), SEQ ID No:25 (serotype D), SEQ ID No:27 (serotpye E), SEQ ID No:29 (serotype F), and SEQ ID No:31 (serotype G). Alternatively, the nucleic acid nucleic acid encodes an HN amino acid sequence of BoNT selected from SEQ ID No:22 (serotype B), SEQ ID No:24 (serotype C1), SEQ ID No:26 (serotype D), SEQ ID No:28 (serotpye E), SEQ ID No:30 (serotype F), and SEQ ID No:32 (serotype G).

Preferably, the nucleic acid of this invention is a synthetic nucleic acid. In a preferred embodiment, the sequence of the nucleic acid is designed by selecting at least a portion of the codons encoding HC from codons preferred for expression in a host organism, which may be selected from gram negative bacteria, yeast, and mammalian cell lines; preferably, the host organism is *Escherichia coli* or *Pichia pastoris*. In another preferred embodiment, the nucleic acid sequence encoding HC is designed by selecting codons encoding HC which codons provide HC sequence enriched in guanosine and cytosine residues. More preferably, nucleic acid encoding HC or HN is expressed in a recombinant host organism with higher yield than a second nucleic acid fragment encoding the same HC sequence, said second nucleic acid fragment having the wild-type *Clostridum botulinum* sequence of HC.

In yet another embodiment, this invention provides anexpression vector comprising the nucleic acid of this invention, whereby HC and/or HN is expressed upon transfection of a host organism with the expression vector. Another embodiment of this invention provides a method of preparing a polypeptide comprising the carboxy-terminal portion of the heavy chain (HC) of botulinum neurotoxin (BoNT) or the amino-terminal portion of the heavy chain (HN) of botulinum neurotoxin (BoNT) selected from the group consisting of BoNT serotype A, BoNT serotype B, BoNT serotype C, BoNT serotype D, BoNT serotype E, BoNT serotype F, and BoNT serotype G, said method comprising culturing a recombinant host organism transfected with the expression vector of of this invention under conditions wherein HC or HN is expressed. Preferably, the recombinant host organism is a eukaryote. In another preferred embodiment, the method of this invention further comprises recovering insoluble protein from the host organism, whereby a fraction enriched in HC or HN is obtained. Preferably, the host organism is *Pichia pastoris*.

In still another embodiment, this invention provides an immunogenic composition comprising the carboxy-terminal portion of the heavy chain (HC) of botulinum neurotoxin (BoNT) selected from the group consisting of BoNT serotype A, BoNT serotype B, BoNT serotype C, BoNT serotype D, BoNT serotype E, BoNT serotype F, and BoNT serotype G. Preferably, the immunogenic composition is prepared by culturing a recombinant organism transfected with an expression vector encoding HC. More preferably, the immunogenic composition is prepared by a method wherein an insoluble protein fraction enriched in HC is recovered from said recombinant organism.

In yet another embodiment, this invention provides an immunogenic composition comprising the amino-terminal portion of the heavy chain (HN) of botulinum neurotoxin (BoNT) selected from the group consisting of BoNT serotype A, BoNT serotype B, BoNT serotype C, BoNT serotype D, BoNT serotype E, BoNT serotype F, and BoNT serotype G. Preferably, the immunogenic composition comprising HN is prepared by culturing a recombinant organism transfected with an expression vector encoding HN. More preferably, the immunogenic composition is prepared from an insoluble protein fraction enriched in HN which is recovered from the recombinant organism.

In still another embodiment, this invention provides an immunogenic composition comprising a polypeptide comprising epitopes contained in the carboxy-terminal portion of the heavy chain (HC) of botulinum neurotoxin (BoNT) and/or the amino-terminal portion of the heavy chain (HN) of botulinum neurotoxin (BoNT) selected from the group consisting of BoNT serotype A, BoNT serotype B, BoNT serotype C, BoNT serotype D, BoNT serotype E, BoNT serotype F, and/or BoNT serotype G, said epitopes eliciting protective immunity toward the respective BoNT serotype. Preferably, the immunogenic composition elicits an ELISA response to the respective BoNT serotype(s) in an animal which is detectable in serum from the animal even when the serum is diluted 100-fold.

BRIEF DESCRIPTION OF THE DRAWINGS

FIGS. 1A and 1B respectively show the nucleotide sequence and the encoded amino acid sequence for a synthetic gene encoding the $H_C$ fragment of BoNT serotype A (SEQ ID NOS:1 and 2).

FIGS. 2A and 2B respectively show the nucleotide sequence and the encoded amino acid sequence for a synthetic gene encoding the $H_C$ fragment of BoNT serotype A (SEQ ID NOS:3 and 4).

FIGS. 3A and 3B respectively show the nucleotide sequence and the encoded amino acid sequence for a synthetic gene encoding the $H_C$ fragment of BoNT serotype A (SEQ ID NOS:5 and 6).

FIGS. 4A and 4B respectively show the nucleotide sequence and the encoded amino acid sequence for a synthetic gene encoding the $H_C$ fragment of BoNT serotype B (SEQ ID NOS:7 and 8).

FIGS. 5A and 5B respectively show the nucleotide sequence and the encoded amino acid sequence for a synthetic gene encoding the H$_C$ fragment of BoNT serotype C (SEQ ID NOS:9 and 10).

FIGS. 6A and 6B respectively show the nucleotide sequence and the encoded amino acid sequence for a synthetic gene encoding the H$_C$ fragment of BoNT serotype D (SEQ ID NOS:11 and 12).

FIGS. 7A and 7B respectively show the nucleotide sequence and the encoded amino acid sequence for a synthetic gene encoding the H$_C$ fragment of BoNT serotype E (SEQ ID NOS:13 and 14).

FIG. 8 shows the nucleotide sequence for a synthetic gene encoding the H$_C$ fragment of BoNT serotype E and the encoded amino acid sequence (SEQ ID NOS:35 and 36).

FIGS. 9A and 9B respectively show the nucleotide sequence and the encoded amino acid sequence for a synthetic gene encoding the H$_C$ fragment of BoNT serotype F (SEQ ID NOS:15 and 16).

FIGS. 10A and 10B respectively show the nucleotide sequence and the encoded amino acid sequence for a synthetic gene encoding the H$_C$ fragment of BoNT serotype G (SEQ ID NOS:17 and 18).

FIGS. 11A and 11B respectively show the nucleotide sequence and the encoded amino acid sequence for a synthetic gene encoding the H$_C$ fragment of BoNT serotype A (SEQ ID NOS:19 and 20).

FIGS. 12A and 12B respectively show the nucleotide sequence and the encoded amino acid sequence for a synthetic gene encoding the H$_N$ fragment of BoNT serotype B (SEQ ID NOS:21 and 22).

FIGS. 13A and 13B respectively show the nucleotide sequence and the encoded amino acid sequence for a synthetic gene encoding the H$_N$ fragment of BoNT serotype C (SEQ ID NOS:23 and 24).

FIGS. 14A and 14B respectively show the nucleotide sequence and the encoded amino acid sequence for a synthetic gene encoding the H$_N$ fragment of BoNT serotype D (SEQ ID NOS:25 and 26).

FIGS. 15A and 15B respectively show the nucleotide sequence and the encoded amino acid sequence for a synthetic gene encoding the H$_N$ fragment of BoNT serotype E (SEQ ID NOS:27 and 28).

FIGS. 16A and 16B respectively show the nucleotide sequence and the encoded amino acid sequence for a synthetic gene encoding the H$_N$ fragment of BoNT serotype F (SEQ ID NOS:29 and 30).

FIGS. 17A and 17B respectively show the nucleotide sequence and the encoded amino acid sequence for a synthetic gene encoding the H$_N$ fragment of BoNT serotype G (SEQ ID NOS:31 and 32).

FIGS. 18A and 18B respectively show the nucleotide sequence and the encoded amino acid sequence for a synthetic gene encoding the H$_C$ fragment of BoNT serotype F (SEQ ID NOS:33 and 34).

FIGS. 19A, 19B, and 19C. FIG. 19A shows the AT base content of a putative fragment C region in native *C. botulinum* DNA. FIG. 19B shows the reduced AT content after the first design (rBoNTF(Hc)1) of the synthetic gene. FIG. 19C shows the AT content of the final gene design (rBoNTF(Hc)2) used to express recombinant rBoNTF(Hc) in *P. pastoris*.

FIG. 20A shows an SDS-PAGE gel and FIG. 20B shows a Western blot of samples at various steps along the rBoNTF(Hc) purification. Lanes from both figures are identical except lane 1, where SDS-PAGE shows Novex mark 12 wide-range molecular weight markers and Western blot shows Novex See Blue prestained molecular weight markers. Lane 2 is the cell lysate, lane 3 is the cell extract, lane 4 is the cell extract after dialysis, lane 5 is pool of rBoNTF(Hc) positive fractions after Mono S column chromatography, and lane 6 is pool of rBoNTF(Hc)-positive fractions after hydrophobic interaction chromatography.

FIG. 21A shows Mono S cation exchange chromatography of extract from *P. pastoris*. Proteins were eluted with increasing NaCl gradient. Fractions positive for rBoNTF(Hc) by Western analysis were pooled individually and subjected to hydrophobic interaction chromatography (the results of which are shown in FIG. 21B) and proteins were eluted with a decreasing ammonium sulfate gradient. In both panels, protein monitored by A280 nm is recorded on the left axis and elution conditions are recorded on the right axis, with the gradient trace laid over the chromatogram.

DETAILED DESCRIPTION OF THE EMBODIMENTS OF THIS INVENTION

Figure 20:
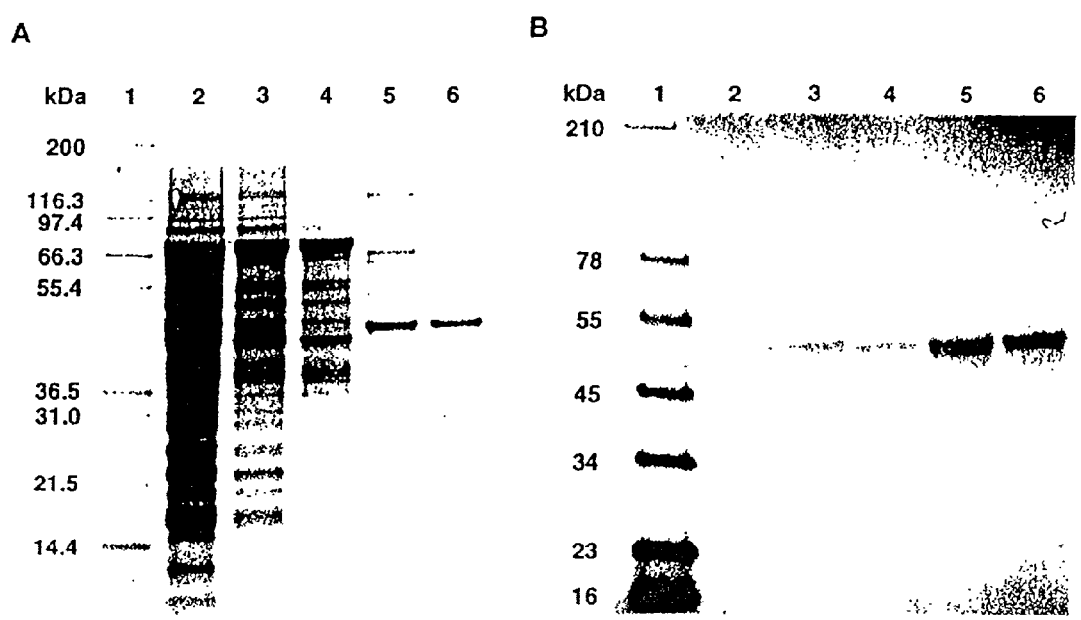
FIGS. 20A and 20B.

The present inventors have determined that animals, including primates, may be protected from the effects of botulinum neurotoxin (BoNT) by immunization with fragments of the botulinum neurotoxin protein expressed by recombinant organisms. Specifically, peptides comprising protective epitopes from the receptor binding domain and/or the translocation domain, found in the carboxy terminal and the amino terminal portions of the heavy chain of the BoNT protein, respectively, are expressed by recombinant organisms transfected with expression vectors encoding the peptides for each serotype of BoNT. Immunization with these recombinantly produced peptides will elicit antibodies capable of protecting animals against intoxication with the BoNT of the respective serotype.

This invention provides a genetically engineered vaccine for protection against botulism. The vaccine comprises fragments of the A and B toxins known as "C fragments" (H$_C$ domain). It is now possible to produce the H$_C$ fragments of the A and B toxins in *E. coli* using gene segment constructs of the HC fragment or an HC polypeptide fused to *E. coli* maltose binding protein. It has been found that the fusion product provides excellent protection against the native toxin challenge. The invention provides plasmids and recombinant proteins for use as vaccines to provide protection against toxins of *Clostridium botulinum*.

Kozaki et al. (in "Antibodies against Botulism Neurotoxin", L. L. Simpson, ed., 1989, Academic Press, New York) suggested that a protective epitope might be present in the 50 kDa carboxyl terminus (HC) region of the protein. Thompson et al. (1990, *Eur. J. Biochem.* 189:73–81 and Accession No. X52066, both of which are incorporated herein in their entirety by reference) deduced the amino acid sequence for the serotype A botulinum toxin. DasGupta et al. (1990, *Biochemie*, 72:661–664) identified the "nick" site for post-translational cleavage of the expressed toxin polypeptide, from which the sequence of the heavy chain can be deduced as SEQ ID NO:41 (amino acids 449 to 1296 of Accession No. X52066). See also Krieglstein, et al., 1994, *J. Protein Chem.*, 13:49–57.

Whelan et al. (*Appl. Environ. Microbiol.* 58:2345–2354, 1992 and Accession No. M81186, both of which are incorporated herein in their entirety by reference) have deduced the amino acid sequence for the serotype B botulinum toxin. Schmidt, et al. (1985, *Arch. Biochem. Biophys.*, 238:544–548) provided N-terminal sequence information for the heavy chain resulting from post-translational cleavage of the expressed toxin polypeptide, and the sequence of the heavy chain can be deduced from this information as SEQ ID NO:42 (amino acids 442 to 1291 of Accession No. M81186).

Analogous post-translational cleavage for all BoNT serotypes produces analogous heavy chain and light chain structures (see Krieglstein, et al., 1994, *J. Protein Chem.*, 13:49–57, and references cited therein).

Synthetic Gene Construction

Preliminary experiments indicated that the DNA sequence found in *C. botulinum* encoding the relevant BoNT fragments are not well expressed in typical recombinant hosts. Therefore, synthetic gene construction was undertaken, based on the amino acid sequence of the respective fragments.

Synthetic gene construction is a technique used to optimize for expression in heterologous host systems. The base composition (i.e., percent A+T or percent G+C) as well as the specific codons in a gene sequence play a role in determining whether a gene from one organism will be optimally expressed in a different organism. There is a reason why certain codons are used and why some are not. Organisms will use the codons in which corresponding tRNAs are present. If the organisms do not use certain codons, they most likely lack those specific tRNAs. As it turns out, codons found in clostridial DNA (i.e., genes found in the genus of bacterial called Clostridium) are very unique both in terms of base composition (i.e., very high A+T base composition) and in the use of codons not normally found in *E. coli* or yeast.

Table 1 is a chart depicting codon usage in *Pichia pastoris*. This table was generated by listing the codons found in a number of highly expressed genes in *P. pastoris*. The codon data was obtained by sequencing the genes and then listing which codons were found in the genes.

From Table 1, it is clear that the amino acid residues can be encoded for by multiple codons. When constructing synthetic genes using *P. pastoris* codon usage, it is preferred to use only those codons that are found in the naturally occurring genes in *P. pastoris*, and it should be attempted to keep them in the same ratio found in the genes of the natural organism. When the clostridial gene has an overall A+T richness of greater than 70% and A+T regions that have spikes of A+T of 95% or higher, they have to be lowered for expression in expression systems like yeast. (Preferably, the overall A+T richness is lowered below 60% and A+T in spikes is also lowered to 60% or below). It is of course necessary to balance keeping the same codon ratio (e.g., for glycine GGG was not found, GGA was found 22% of the time, GGT was found 74% of the time, GGC was found 3% of the time) with reducing the high A+T content. In the construction of the genes, it is preferred to keep the A+T spikes about 55%.

TABLE 1

| Amino Acid | Codon | Number | Fraction |
|---|---|---|---|
| Gly | GGG | 0.00 | 0.00 |
| Gly | GGA | 59.00 | 0.22 |
| Gly | GGT | 197.00 | 0.74 |
| Gly | GGC | 9.00 | 0.03 |
| Glu | GAG | 112.00 | 0.58 |
| Glu | GAA | 80.00 | 0.42 |
| Asp | GAT | 56.00 | 0.32 |
| Asp | GAC | 118.00 | 0.88 |
| Val | GTG | 10.00 | 0.05 |
| Val | GTA | 8.00 | 0.04 |
| Val | GTT | 107.00 | 0.50 |
| Val | GTC | 87.00 | 0.41 |
| Ala | GCG | 1.00 | 0.00 |
| Ala | GCA | 25.00 | 0.10 |
| Ala | GCT | 147.00 | 0.80 |
| Ala | GCC | 71.00 | 0.29 |
| Arg | AGG | 2.00 | 0.01 |
| Arg | AGA | 111.00 | 0.79 |
| Ser | AGT | 8.00 | 0.04 |
| Ser | AGC | 3.00 | 0.02 |
| Lys | AAG | 145.00 | 0.79 |
| Lys | AAA | 38.00 | 0.21 |
| Asn | AAT | 18.00 | 0.13 |
| Asn | AAC | 119.00 | 0.87 |
| Met | ATG | 80.00 | 1.00 |
| Ile | ATA | 0.00 | 0.00 |
| Ile | ATT | 83.00 | 0.58 |
| Ile | ATC | 72.00 | 0.44 |
| Thr | ACG | 5.00 | 0.03 |
| Thr | ACA | 8.00 | 0.05 |
| Thr | ACT | 88.00 | 0.50 |
| Thr | ACC | 74.00 | 0.43 |
| Trp | TGG | 38.00 | 1.00 |
| End | TGA | 0.00 | 0.00 |
| Cys | TGT | 35.00 | 0.83 |
| Cys | TGC | 7.00 | 0.17 |
| End | TAG | 1.00 | 0.20 |
| End | TAA | 4.00 | 0.80 |
| Tyr | TAT | 18.00 | 0.12 |
| Tyr | TAC | 128.00 | 0.88 |
| Leu | TTG | 120.00 | 0.52 |
| Leu | TTA | 21.00 | 0.08 |
| Phe | TTT | 24.00 | 0.19 |
| Phe | TTC | 104.00 | 0.81 |
| Ser | TCG | 8.00 | 0.03 |
| Ser | TCA | 14.00 | 0.07 |
| Ser | TCT | 89.00 | 0.47 |
| Ser | TCC | 71.00 | 0.37 |
| Arg | CGG | 2.00 | 0.01 |
| Arg | CGA | 0.00 | 0.00 |
| Arg | CGT | 26.00 | 0.18 |
| Arg | CGC | 0.00 | 0.00 |
| Gln | CAG | 31.00 | 0.34 |
| Gln | CAA | 59.00 | 0.66 |
| His | CAT | 11.00 | 0.13 |
| His | CAC | 77.00 | 0.88 |
| Leu | CTG | 35.00 | 0.15 |
| Leu | CTA | 7.00 | 0.03 |
| Leu | CTT | 43.00 | 0.18 |
| Leu | CTC | 7.00 | 0.03 |
| Pro | CCG | 0.00 | 0.00 |
| Pro | CCA | 97.00 | 0.57 |
| Pro | CCT | 66.00 | 0.39 |
| Pro | CCC | 7.00 | 0.04 |

Considering codon usage for a number of organisms including *E. coli*, it turns out that a synthetic gene using *E. coli* codon usage also expresses fairly well in *P. pastoris*. Similarly, a synthetic gene using *P. pastoris* codon usage also appears to express very well in *E. coli*.

Synthetic genes for the $H_C$ fragments of botulinum neurotoxin serotypes A–G are shown in FIGS. 1–10, along with the amino acid sequences encoded by the synthetic genes. Synthetic genes for the $H_N$ fragments of botulinum neurotoxin serotypes A–G are shown in FIGS. 11–17, along with the amino acid sequences encoded by the synthetic genes. Synthetic genes having alternative gene sequences may be prepared by following the guidance provided herein concerning codon selection. The amino acid sequence encoded by such synthetic genes will preferably be the sequence of one of the BoNT serotype proteins, or a fragment thereof which contains protective epitopes. Suitable fragments include the $H_C$ fragments of BoNT serotypes A, B $C_1$, D, E, F, and G, and the $H_N$ fragments of BoNT serotypes A, B, $C_1$, D, E, F, and G. Such alternative gene sequences are within the contemplation of this invention.

Also within the contemplation of this invention are proteins containing protective epitopes from both the N-terminal and the C-terminal domains of the respective serotype BoNT proteins. Such proteins may be prepared by fusing a sequence encoding the translocation domain (HN) to the sequence of the HC region. This may be accomplished by removing the restriction enzyme site of the 3' end of the translocation domain gene as well as the termination codon, and also removing the initiation codon, restriction enzyme site and any other nucleotides on the 5' end of the gene that are not part of the botulinum toxin gene. Then a common restriction enzyme site not found in either synthetic gene may be inserted on the 3' end of the $H_N$ gene and the 5' end of the $H_C$ gene, and this common restriction site may be used to fuse the two genes together.

Recombinant Peptide Production

The nontoxin fragment is very safe, will not require formalin treatment, and has been shown to produce significant immunity against the fully toxic parent molecule. There are two major advantages of the invention over the presently employed vaccine. First, the recombinantly-produced botulinum neurotoxin (rBoNT) protein fragments are completely nontoxic and, is thus, very safe. The fermentation of the host cell harboring the rBoNT gene (e.g., *Escherichia coli* or *Pichia pastoris*) will not require the high biological containment facilities presently needed to ferment the spore-forming *Clostridium botulinum* required for the production of the toxoid vaccine. Second, the synthetic gene can be placed in high expression systems and used to make much larger quantities of the fragment than toxin produced by the parent organism, *Clostridium botulinum*. Thus, there will be immense cost savings because it will be easier and safer to produce much larger quantities of the vaccine than is now possible.

Synthetic genes as described herein may be transfected into suitable host organisms to create recombinant production organisms, and cultures of these recombinant organisms can then be used to produce immunogenic peptide fragments capable of conferring protective immunity against BoNT of the respective serotypes. Exemplary techniques for transfection and production of BoNT fragments are shown in the Examples. Alternative techniques are well documented in the literature (See, e.g., Maniatis, Fritsch & Sambrook, "Molecular Cloning: A Laboratory Manual" (1982); "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984), and Sambrook, et al., "Molecular Cloning: a Laboratory Manual" (1989)). Such techniques are explained fully in the literature, and modification of these techniques within the scope of this invention is within the skill in the art.

The synthetic gene for BoNT serotype B fragment $H_C$ (see FIG. 4A) has been inserted into the yeast expression vector pHIL-D4, and integrated into the chromosome of *Pichia pastoris* strain GS115. The expressed product (see amino acid sequence in FIG. 4B) had the expected molecular weight as shown by denaturing polyacrylamide gel electrophoresis (PAGE) and Western blot analysis using antibodies directed against botulinum neurotoxin serotype B. The expressed recombinant BoNTB ($H_C$) elicited high antibody titers as judged by the Enzyme Linked Immunosorbent Assay (ELISA) and, more importantly, these circulating serum titers protected mice, guinea pigs, and non-human primates from challenges with active toxin. Industrial scale manufacturing processes (fermentation and purification) have been completed and a pilot lot has been produced in compliance with cGMP.

The synthetic gene for BoNT serotype C fragment $H_C$ (see FIG. 5A) has been inserted into the yeast expression vector pHIL-D4, and integrated into the chromosome of *Pichia pastoris* strain GS1 15. The expressed product (see amino acid sequence in FIG. 5B) had the expected molecular weight as shown by denaturing polyacrylamide gel electrophoresis (PAGE) and Western blot analysis using antibodies directed against botulinum neurotoxin serotype C. The expressed recombinant BoNTC ($H_C$) elicited high antibody titers as judged by the Enzyme Linked Immunosorbent Assay (ELISA) and, more importantly, these circulating serum titers protected mice from challenges with active toxin.

The synthetic gene for BoNT serotype D fragment $H_C$ (see FIG. 6A) has been inserted into the yeast expression vector pHIL-D4, and integrated into the chromosome of *Pichia pastoris* strain GS1 15. The expressed product (see amino acid sequence in FIG. 6B) had the expected molecular weight as shown by denaturing polyacrylamide gel electrophoresis (PAGE) and Western blot analysis using antibodies directed against botulinum neurotoxin serotype D. The expressed recombinant BoNTD ($H_C$) elicited high antibody titers as judged by the Enzyme Linked Immunosorbent Assay (ELISA) and, more importantly, these circulating serum titers protected mice from challenges with active toxin.

The synthetic gene for BoNT serotype E fragment $H_C$ (see FIG. 7A) has been inserted into the yeast expression vectors pHILD2, pHILD3, and pPIC9K (see FIG. 7B). A modified form of the synthetic gene in which an internal EcoRI site was removed and the gene was enlarged (see FIG. 8) was inserted into the yeast vector pHIL-D4, and integrated into the chromosome of *Pichia pastoris* strain GS115. The expressed product (see amino acid sequence in FIG. 8) had the expected molecular weight as shown by denaturing polyacrylamide gel electrophoresis (PAGE) and Western blot analysis using antibodies directed against botulinum neurotoxin serotype E. The expressed recombinant BoNTE ($H_C$) elicited high antibody titers as judged by the Enzyme Linked Immunosorbent Assay (ELISA) and, more importantly, these circulating serum titers protected mice from challenges with active toxin.

The synthetic gene for BoNT serotype F fragment $H_C$ (see FIG. 9A) has been inserted into the yeast expression vector pHIL-D4, and integrated into the chromosome of *Pichia pastoris* strain GS115. The initial step in the development of the rBoNTF($H_C$) vaccine candidate was to design a gene which could satisfactorily be expressed in a pichia host. A synthetic gene encoding rBoNTF($H_C$) was constructed to lower the inherent AT richness of the native clostridial gene and to remove any potentially rare codons. Clostridial genes having an AT content in excess of 65% or having an average AT content but containing AT-rich tracts usually contain multiple terminators/polyadenylation signals, which can result in premature termination of transcripts when expression is attempted in yeast (Romanos, M. A., et al., (1995), "Expression of Cloned Geries in Yeast," *DNA Cloning* 2: Expression Systems," (Glover D., et al., Eds.), Oxford Univ. Press, London). The synthetic gene in this study required two successive rounds of alterations before the yeast could properly produce full-length antigen. The expressed product (see amino acid sequence in FIG. 9B) had the expected molecular weight as shown by denaturing polyacrylamide gel electrophoresis (PAGE) and Western blot analysis using antibodies directed against botulinum neurotoxin serotype F.

A previous study (Hatheway, 1976) demonstrated that the serotype F toxoid antigen needed to be at least partially purified to be efficacious. The same observation was noted with the rBoNTF($H_C$) antigen produced in pichia cells as the crude cell lysate did not protect mice against a BoNTF challenge. The putative receptor-binding domain of BoNTF was purified from yeast and shown to be efficacious in a mouse model. The expressed recombinant BoNTF ($H_C$) elicited high antibody titers as judged by the Enzyme Linked Immunosorbent Assay (ELISA) and, more importantly, these circulating serum titers protected mice from challenges with active toxin.

The synthetic gene for BoNT serotype G fragment $H_C$ (see FIG. 10A) has been inserted into the yeast expression vector pHIL-D4, and integrated into the chromosome of Pichia pastoris strain GS115. The expressed product (see amino acid sequence in FIG. 10B) had the expected molecular weight as shown by denaturing polyacrylamide gel electrophoresis (PAGE) and Western blot analysis using antibodies directed against botulinum neurotoxin serotype G. The expressed recombinant BoNTG ($H_C$) elicited high antibody titers as judged by the Enzyme Linked Immunosorbent Assay (ELISA) and, more importantly, these circulating serum titers protected mice from challenges with active toxin.

When purifying a protein for the first time, it is important to generate a viable means for identifying which fractions contain product. If the protein of interest is not an enzyme or does not absorb at a unique wavelength, there are still suitable assays (for example mass spectrometry) for identifying the product. The inventors chose to monitor the purification of rBoNT($H_C$) through immunological detection by Western blot analysis. However, with various polyclonal antibodies against whole toxin available but without an appropriate positive control, the Western blot results can only be interpreted as ambiguous until a purified sample is sequenced or shown to be protective.

There are two major issues of concern when extracting C-fragment, $H_N$, and/or heavy chain ($H_C$) antigens from pichia cells. The first concern is the solubility of these proteins (i.e., can enough product be extracted into the soluble fraction for further processing?). The second concern deals with the effective removal of polynucleic acids and/or other contaminating materials, which strongly interfere with the necessary chromatography.

The zwiterionic detergent, CHAPS, is most notably an effective agent for solubilizing membrane proteins. Membrane proteins exist in a hydrophobic environment, and if removed from that environment, possess strong tendencies to aggregate and ultimately precipitate. CHAPS prevents that aggregation from occurring with membrane bound proteins. The inventors extrapolated this premise to the clostridial proteins noted above. C-fragments, translocation domains (HN), and entire heavy chains are missing their natural partner (the remaining segments of the neurotoxin) and thus, presumably bare exposed hydrophobic regions on their protein surface where the $H_C$, $H_N$, or heavy chain normally associates with rest of the neurotoxin. These exposed hydrophobic regions are potential nucleation sources for protein aggregation, because the natural tendency of a protein in an aqueous environment is to bury their hydrophobic surface. When pichia cells are disrupted with CHAPS (on the order of 0.3% W/V) present in the cracking buffer, the amount of fragment C protein isolated in the soluble fraction has been observed to increase from less than 5% to nearly 80% with serotype $C_1$. Dramatic increases in solubility have been noted with C-fragment serotypes A and F as well.

Once a soluble antigen has been produced, the subsequent task is to separate that antigen from the myriad of pichia host proteins, lipids, and other impurities that exist in the extracted medium. In order for the chemical separations to be feasible by liquid chromatography, it is critical that polynucleic acids be efficiently removed. Nucleotides will either bind to the C-fragment (serotypes A, E, and F due to their elevated pIs) or will bind to the anion-exchange chromatography resin (as is used in the first purification step of the $C_1$ process). With either case, the chromatography is rendered futile. The C-fragment product will either fail to bind to the chromatography media or it will elute over an unacceptably large sodium chloride concentration range. Pichia cells possess an abundant amount of DNA. Polyethyleneimine (PEI) is a polycationic agent that readily precipitates nucleotides. When pichia cell extracts are treated with PEI, the nucleic acids are efficiently precipitated and removed by centrifugation without significant loss of product. More importantly, the chromatographic separation of C-fragments from pichia proteins are dramatically improved.

The soluble portion of the cell lysate may typically be purified in two conventional chromatographic steps. The ultimate objective of this work is to obtain FDA licensure of rBoNT as a safe and effective vaccine. Even though separations can be accomplished at extremely high resolution with affinity chemistry, there remains an undesirable effect of hapten leaching from the resin. Thus, a preferred separation employs a cation-exchange step followed by hydrophobic interaction chromatography (HIC). These two steps complement each other as they provide separations based on electrostatic and hydrophobic interactions. The cation-exchange step was particularly efficient in increasing the purity of rBoNTF($H_C$), as the antigen was estimated to be purified greater than 52-fold. The efficiency of purification is primarily attributed to the significant difference in isoelectric points between most pichia proteins (pIs<7) and rBoNT($H_C$) (experimental pI=9.4 for rBoNTF($H_C$), data not shown) and thus, the pichia proteins were removed in the column flow through. Precipitate that results when the cation-exchange pool is treated with ammonium sulfate contains mostly pichia proteins and very little rBoNT product. The HIC step removes most or all of the remaining impurities. The yield of soluble rBoNTF($H_C$) from the total recombinant yeast cell lysate was estimated to be greater than 28% with a purity greater than 98%. Use of similar purification steps for rBoNTA($H_C$) produced greater than 95% pure material.

A significant amount of rBoNTF($H_C$) product (30–40%) was identified in the insoluble portion of the cell lysate. Also, the antigen was 35% of the total protein present in the pellet; in effect it was more pure than the soluble rBoNTF ($H_C$) was after the ion-exchange step. This suggests an alternative process whereby insoluble rBoNT product produced in yeast may be resolubilized and purified to homogeneity. The resolubilization may be performed by resuspending the pellet in urea and subsequently removing the urea by dialyses in nondenaturing buffer. A single chromatographic step using cation-exchange chemistry may be sufficient to purify the resolubilized antigen, in some cases to greater than 98%. The yield of resolubilized rBoNTF($H_C$) product from the total cell lysate was estimated to be >19%. The overall bench scale yield of purified soluble and resolubilized rBoNTF($H_C$) was estimated to be greater than 47% or 240 mg/Kg of the cell paste. A similar procedure would be suitable for purification of rBoNTA($H_C$) and other rBoNT fragment peptides from yeast.

Analysis of CD spectra of both soluble and resolubilized product revealed the presence of significant β-sheet which is in agreement with that predicted for rBoNTF($H_C$) using an artificial neural network (Lebeda, F. J., et al., (1997), "Predicting Differential Antigen-Antibody Contact Regions Based on Solvent Accessibility," *J. Protein Chem.*, 16:607–618), and that determined by crystal structure of BoNT serotype A (Lacy, D. B., et al., (1998), "Crystal Structure of Botulinum Neurotoxin Type A and Implications for Toxicity," *Nat. Struct. Biol.*, 5:898–902). However, even though CD revealed that the two antigens possessed similar folds, there were subtle differences between the two spectra suggesting that the secondary structures, and hence, tertiary structures were not identical.

Immunization

The purified soluble and resolubilized antigens appear to be in a folded conformation. However, the bottom line with any potential vaccine is the demonstration of protection. Are the antigens in a conformation that will elicit the production of neutralizing antibody? To answer this question, mice were inoculated with rBoNTF($H_C$) and subsequently challenged with a high level of rBoNTF toxin. The purified soluble rBoNTF($H_C$) completely protected mice receiving three inoculations of 0.2 μg from challenge with 1000 mouse i.p. $LD_{50}$ of BoNT/F toxin. Analysis of the association of dose with survival indicated that dose was associated with the odds of surviving (odds ratio=2.0, meaning that the odds of survival increase twofold per unit increase in dose with a 95% confidence level from 1.3 to 3.1). The number of inoculations was also associated with survival. Both two inoculations and three inoculations were associated with increased odds of survival relative to a single inoculation (5.3-fold with a 95% confidence level of 1.2–23 for two inoculations and 22-fold with a 95% confidence level of 4.3–110 for three inoculations). It is apparent that a single shot at higher doses achieved protection comparable to multiple inoculations at lower doses. Also, three doses of 1 μg of purified resolubilized rBoNTF($H_C$) completely protected mice from a challenge of 5000 mouse i.p. $LD_{50}$ of BoNTF toxin, thus demonstrating that refolded rBoNTF($H_C$) from the insoluble fraction of lysate could also be a prosperous source of antigen.

Individual antibody ELISA titer appears to be an excellent predictor of mouse survival. If the antibody titer of a mouse was 100 or greater, that mouse was predicted to and did survive a challenge of 1000 mouse i.p. $LD_{50}$ of BoNTF toxin. Upon vaccination of mice with 2 or 3 doses of rBoNTA($H_C$) or rBoNTB($H_C$) vaccine delivered on a specific schedule (i.e., parental intramuscular injection at 0, 4, and 8 weeks), survival of animals challenged with 100,000 or 1,000,000 million LD50 of toxin is very high. Measurement of the antibody levels in these animals via an ELISA shows that the survival rate can be correlated with the measured antibody level. The ELISA is performed by coating a microtiter plate with toxin or fragment C itself, then sera from the vaccinated mice is added at various dilutions (i.e., sera diluted 1/100, 1/400, 1/1600, 1/6400, etc.). Since fragment C is sufficient to elicit protection in animals, preferably assays for neutralizing antibody titer in sera from animals vacinated with fragment C are performed using microtiter plates coated with fragment C. Antibody in the sera will bind to the toxin or the fragment C, and the bound antibody may be detected by a secondary antibody (e.g., anti-mouse IgG) that is coupled to horse-radish peroxidase or alkaline phosphatase. The secondary IgG will bind to the anti-BoNT antibody that was raised to the fragment C vaccine. After washing the microtiter wells, a substrate for the peroxidase or phosphatase enzymes is added to the wells. The substrate will give off a color once the enzyme has cleaved the substrate, and the intensity of the color measured (e.g., at 405 nm. Typically, a reading of 0.2 is used as the base. Thus, if dilution of the sera by 1/1600 gives a reading of 0.15 at 405 nm and a dilution of 1/400 gives a reading of 0.45 at 405 nm, the antibody titer in the sera in characterized as 1/400 dilution (i.e., titer of 400 fold). Obviously, if readings of 0.2 are obtained at higher dilutions, better protection is observed. With rBoNTA($H_C$) vaccination, for mice which had ELISA titers of less than 100, only 14.3% survival rate was observed under the conditions of vaccination and challenge. With rBoNTF($H_C$), for mice which had ELISA titers of 100 fold, under the condition of vaccination and challenge, 100% of the mice were protected.

It also will be well known to one of ordinary skill in the art that a susceptible host may be immunized using the appropriate peptide vaccine formulated in adjuvant to increase the immune response. Such adjuvants include but are not limited to Freund's (complete and incomplete), mineral gels, such as aluminum hydroxide, surface active substances such as keyhole limpet hemocyanin, lysolecithin, pluronic polyols, polyanions, peptides, BCG (Bacille Calmette-Guerin), oil emulsions and dinotrophenols. Immunization can be carried out with additional various presentation and cross-linking permutations. By way of example and not of limitation, such permutations include rBoNT peptides cross-linked to KLH as a carrier, any rBoNT peptide cross-linked to any other rBoNT protein as carrier, rBoNT peptides cross-linked to themselves, and these combinations presented by the various adjuvants listed above. It will become evident that such permutations are available in regard to other peptides and self-assembled peptides disclosed throughout this specification.

It will also be known to one of ordinary skill in the art that use of the term "susceptible host" includes any such mammalian host susceptible to intoxication by BoNT. It will be further evident that any such susceptible host is a candidate for treatment to promote protection from BoNT utilizing the peptide vaccines and associated methods described in this specification.

EXAMPLES

In order to facilitate a more complete understanding of the invention, a number of Examples are provided below. However, the scope of the invention is not limited to specific embodiments disclosed in these Examples, which are for purposes of illustration only.

Example 1

Synthesis and Cloning of a Synthetic Gene Encoding rBoNTF($H_C$)

A synthetic gene encoding a putative fragment C region of botulinum neurotoxin serotype F was designed and constructed for expression in *Escherichia coli* (Holley et al., submitted to Vaccine). The recombinant BoNTF($H_C$)$_1$ gene was expressed in *E. coli* as a fusion protein with maltose-binding protein (MBP) with yields of 1 mg/L culture (See FIG. 18).

The same gene was used for expression studies in the yeast, *P. pastoris*. This particular host was chosen because it could produce high levels of recombinant proteins (Cregg, J. M., et al., (1993), "Recent Advances in the Expression of Foreign Genes in *Pichia pastoris*," *Bio/Technology*, 11:905–909; Romanos, M. A., et al., (1992), "Foreign Gene Expression in Yeast: A Review," *Yeast*, 8:423488; Sreekrishna, K., et al., (1988), "High Level Expression of Heterologous Proteins in Methylotrophic Yeast *Pichia pastoris*," *J. Bas. Microbiol.*, 28:265–278) and because it lacked endotoxins which would facilitate product development. Intracellular expression of the antigen was used to avoid potential glycosylation of the recombinant protein. The rBoNTF($H_C$)$_1$ gene was modified at its 3' end for insertion into the unique EcoR I site of the yeast vector, pHILD4. The recombinant construct containing the rBoNTF ($H_C$)$_1$ gene was subsequently linearized with Sac I and the cassette integrated into the chromosomal alcohol oxidase (AOX 1) of *Pichia pastoris* strain GS115 (Clare, J. J., et al., (1991), "High-Level Expression of Tetanus Toxin Fragment C in *Pichia pastoris* Strains Containing Multiple Tandem Integrations of the Gene," *Bio/Technology*, 9:455460). Yeast transformants expressing the selectable markers histidine dehydrogenase (Cregg, J. M., et al., (1985), "*Pichia pastoris* as a Host System for Transformations," *Mol. Cell. Biol.*, 5:3376–3385) and aminoglycoside phosphotransferase 3' (1) (Scorer, C. A., et al., (1994), "Rapid Selection Using G418 of High Copy Number Transformants of *Pichia pastoris* for High-Level Foreign Gene Expression," Bio/Technology, 12:181–184) were isolated These isolates were further characterized for their ability to express rBoNTF($H_C$) after induction with methanol. Although the various transformants generated were able to express the selectable markers, no expression of rBoNTF($H_C$) as judged by SDS/PAGE and blot analysis was observed in these isolates (data not shown).

SDS/PAGE, Western Blot, and Protein Assays

Total protein concentrations were determined by using the Pierce BCATM (bicinchoninic acid) protein assay kit with BSA as a standard The purity of the rBoNTF($H_C$) product was assessed by SDS/PAGE with Novex (San Diego, Calif., U.S.A.) gel electrophoresis supplies, reagents, protocols, and National Institutes of Health (NIH) imaging software as previously described (Byrne, M. P., et al., (1998), "Purification, Potency, and Efficacy of the Botulinum Neurotoxin Type A Binding Domain from *Pichia pastoris* as a Recombinant Vaccine Candidate," *Infect. Immun.*, 66:4817–4822). Western blot assays were used to identify FPLC fractions containing rBoNTF($H_C$) as previously described (Byrne, 1998) with the following changes The primary antibody used was a polyclonal protein G sepharose-purified horse anti-BoNTF antibody incubated at 1 μg/ml for 3 h. The secondary antibody used was a horseradish peroxidase-labeled affinity-purified goat anti-horse IgG (Kirkegaard & Perry Laboratories, Gaithersburg, Md., U.S.A.) assayed at 1 μg/ml for 2 h.

Example 2

Synthesis and Cloning of a Synthetic Gene Encoding rBoNTF($H_C$)

A second synthetic gene, rBoNTF($H_C$)$_2$, was subsequently designed to facilitate expression in *P. pastoris*. Redesigning the gene was intended to lower specific regions of the rBoNTF($H_C$)$_1$ gene in which spikes of AT-rich tracts still remained. Previous work had shown that rare codons (Makoff, A. J., et al., (1989), "Expression of Tetanus Toxin Fragment C in *E. coli*: High Level Expression by Removing Rare Condons," *Nucleic Acids Res.*, 17:10191–10201) and/or highly enriched AT base compositions (Romanos, M. A., et al., (1991), "Expression of Tetanus Toxin Fragment C in Yeast: Gene Synthesis is Required to Eliminate Fortuitous Polyadenylation Sites in AT-rich DNA," *Nucleic Acids Res.*, 19:1461–1467) in clostridial DNA were incompatible with optimum expression of clostridial genes in *E. coli* and yeast. A second synthetic gene encoding the rBoNTF($H_C$) fragment was designed and constructed using *P. pastoris* codon usage (Sreekrishna, K., (1993), "Strategies for Optimizing Protein Expression and Secretion in the Methylotrophic Yeast *Pichia pastoris*," *Industrial Micororganisms: Basic and Applied Molecular Genetics*, (Baltz, R. H., et al, Eds.), pp. 119–126, Am. Soc. Microbiol., Washington, D.C.). Briefly, complimentary oligonucleotides encoding the amino terminal region of the F($H_C$)(423 nucleotides flanked with EcoRI and PstI sites), the central region of the F($H_C$) (606 nucleotides flanked by PstI and SalI sites) and the carboxy-terminal region of F($H_C$) (336 nucleotides flanked by SalI and EcoRI sites) were annealed and cloned into pUC or PCR zero-blunt plasmid vectors. The AT base composition in the native clostridial F($H_C$) DNA averaged 76% while rBoNTF($H_C$)$_1$ averaged 58% and rBoNTF($H_C$)$_2$, 53% (FIG. 19). The synthetic gene sequence of rBoNTF($H_C$)$_2$ and the 432 amino acids it encoded for is shown in FIG. 9 After nucleotide sequencing, the cloned fragments were excised by the appropriate restriction endonucleases, separated by agarose gel electrophoresis, and purified The isolated DNA fragments were ligated simultaneously into EcoR I digested and dephosphorylated plasmid pHILD4. The vector harboring the rBoNTF($H_C$)$_2$ gene was integrated into the chromosomal AOX1 locus of *P. pastoris* as described above. Transformants expressing selectable markers (histidine dehydrogenase and aminoglycoside phosphotransferase 3' (I)) were isolated and tested for their ability to express rBoNTF($H_C$). Unlike the rBoNTF($H_C$)$_1$ gene, rBoNTF($H_C$)$_2$ was expressed after induction with methanol and yielded the expected molecular weight of approximately 50000 daltons as judged by SDS/PAGE and Western blot analysis (FIG. 20). The deduced molecular mass of the encoded polypeptide was 50,250 daltons.

Example 3

Expression and Cell Disruption of rBoNTF($H_C$) in *P. pastoris*

Large-scale fermentation conditions and optimal intracellular expression of rBoNTF($H_C$) were determined for the yeast strain *P. pastoris*.

Protein Expression

A stock seed culture of *P. pastoris* was grown in shake-flasks containing 0.5 L of YNB medium (13.4 g/L yeast nitrogen base without amino acids, 20 g/L glycerol, 0.4 mg/L biotin, in 100 mM sodium phosphate, pH 6.0). Cultures were grown at 30° C. until an $A_{600}$ of 20 absorbance units was achieved, and then used to inoculate a 5-L BioFlo 3000 fermentor (New Brunswick Scientific, Edison, N.J., U.S.A.) containing 2.5 L basal-salt medium plus PTM4 trace mineral salts and 4% glycerol. Dissolved oxygen was maintained at 40% and the pH was maintained at 5.0 with 30% ammonium hydroxide. After the initial glycerol was consumed, 50% (w/v) glycerol was added at a rate of 20 g/L/h for 1 h then decreased linearly to 0 g/L/h over 3 h The medium was enriched with 1.5 g methanol/L of medium Methanol feed was started at 4 g/L/h and linearly increased to 9 g/L/h over 10 h The methanol feed rate was adjusted by using the dissolved oxygen-spike method (Chiruvolu, V., et al., (1997), "Recombinant Protein Expression in an Alcohol Oxidase-Defective Strain of *Pichia pastoris* in Feed-Batch Fermentations, *Enzyme Microbiol. Technol.*, 21:277–283). After 10 h of methanol induction, the cells were harvested by centrifugation at 6000 g for 10 min at 4° C. with a Beckman JA-10 rotor (Beckman Instruments, Palo Alto, Calif., U.S.A.) and then stored at −20° C.

Protein Expression

A stock seed culture of *P. pastoris* was grown in shake-flasks containing 0.5 L of YNB medium (13.4 g/L yeast nitrogen base without amino acids, 20 g/L glycerol, 0.4 mg/L biotin, in 100 mM sodium phosphate, pH 6.0). Cultures were grown at 30° C. until an $A_{600}$ of 20 absorbance units was achieved, and then used to inoculate a 5-L BioFlo 3000 fermentor (New Brunswick Scientific, Edison, N.J., U.S.A.) containing 2.5 L basal-salt medium plus PTM4 trace mineral salts and 4% glycerol. Dissolved oxygen was maintained at 40% and the pH was maintained at 5.0 with 30% ammonium hydroxide. After the initial glycerol was consumed, 50% (w/v) glycerol was added at a rate of 20 g/L/h for 1 h then decreased linearly to 0 g/L/h over 3 h. The medium was enriched with 1.5 g methanol/L of medium Methanol feed was started at 4 g/L/h and linearly increased to 9 g/L/h over 10 h. The methanol feed rate was adjusted by using the dissolved oxygen-spike method (Chiruvolu, 1997). After 10 h of methanol induction, the cells were harvested by centrifugation at 6000×g for 10 min at 4° C. with a Beckman JA-10 rotor (Beckman Instruments, Palo Alto, Calif., U.S.A.) and then stored at −20° C.

Cell disruption and sample preparation Eleven g of frozen cell paste was resuspended in 100 ml of 50 mM $Na_2HPO_4$/2 mM $Na_2EDTA$/l mM PMSF, pH 6.8 at 4° C. The suspended cells were disrupted by three successive passes through a microfluidizer device (model 110Y, Microfluidics Corp., Newton, Mass., U.S.A.) at 21000 psi The temperature of the disruptate was kept below 10° C. throughout the process by cooling the exit line and collection flask with ice The cells were judged to be greater than 95% disrupted as determined by microscopy. In comparison, 8–10 passes through a Gaulin homogenizer were required to efficiently disrupt the cells in past protocols. SDS-PAGE and Western blot analysis of cell lysate showed that expressed rBoNTF($H_C$) represented <0.5% of the total protein. The resulting cell lysate volume was 105 ml with a protein concentration of 11 mg/ml Cellular debris and insoluble proteins were removed by centrifugation at 15000 g for 15 min at 4° C. with a Sorval SS-34 rotor (Sorval Instruments, Newtown, Conn., U.S.A.). The resulting extract was noticeably turbid due to the presence of lipids and significant quantities of nucleic acids. As rBoNTF($H_C$) possessed a calculated isoelectric point of 9.1 and presumably interacted strongly with DNA, DNase was added to the cell extract in order to digest the polynucleotides and facilitate purification. To remove the polynucleotides, the extract was treated with DNase (100 units/ml, Aldrich) and $ZnCl_2$ (2 mM, Aldrich) at room temperature for 30 min and then dialyzed extensively with 10 kDa molecular weight cut off (MWCO) Slide-A-Lyzer dialysis cassettes (Pierce) in 50 mM $Na_2HPO_4$/2 mM $Na_2EDTA$/1 mM PMSF, pH 6.8 at 4° C. A precipitate developed during dialysis that was separated by centrifugation at 15000 g for 15 min at 4° C. with a Sorval SS-34 rotor. The clarified extract contained 7.8 mg/ml of total protein and was used as starting material for the FPLC purification of soluble rBoNTF($H_C$) while the pellet was used as starting material for the resolubilized rBoNTF($H_C$) purification.

Example 4

Conventional Purification of rBoNTF($H_C$) from *P. pastoris*

Figure 21:
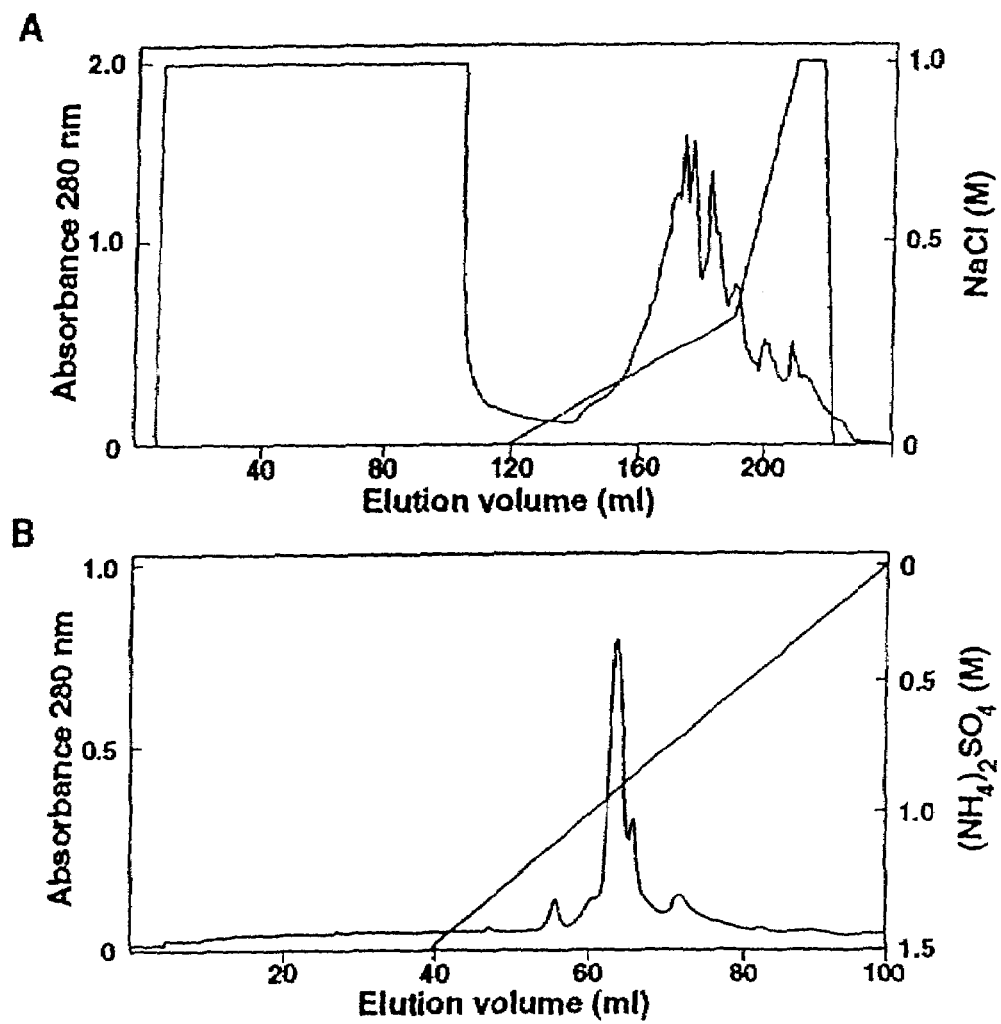
FIGS. 21A and 21B show purification of rBoNTF(Hc) by sequential chromatography.

The rBoNTF($H_C$) protein was purified to homogeneity using an FPLC system and two chromatographic steps. First, the material was subjected to cation exchange chromatography (FIG. 21A).

FPLC Purification of Soluble rBoNTF($H_C$)

Soluble rBoNTF($H_C$) was purified by using a Pharmacia model 500 FPLC system (Pharmacia, Uppsala, Sweden) with programmed elution and $A_{280}$ monitoring. The starting material was loaded onto a Pharmacia HR 10/10 Mono S cation-exchange column equilibrated with 50 mM $Na_2HPO_4$/2 mM $Na_2EDTA$/1 mM PMSF, pH 6.8 (buffer A) at a flow rate of 2 ml/min (150 cm/h). The column was washed with 16 ml (2 bed volumes) of buffer A Flow through and wash were collected separately and stored for subsequent analysis. Protein was eluted from the column with a linear gradient from 0 to 300 mM NaCl over 80 ml (10 bed volumes), then a linear gradient from 300 to 1000 mM NaCl over 20 ml (2.5 bed volumes), and then an isocratic gradient at 1000 mM over 10 ml (1.25 bed volumes). Four-ml fractions were collected throughout the linear and isocratic gradients. This step was highly efficient as most pichia proteins possess isoelectric points between pH 5 and 7 and, therefore, pass through the column without binding. Fractions eluting between 230 and 260 mM NaCl were positive for rBoNTF($H_C$) by Western blot analysis and were pooled. The pooled fractions were adjusted to 1.5 M ammonium sulfate by the slow addition of 2 M $(NH_4)_2SO_4$/50 mM $Na_2HPO_4$/2 mM $Na_2EDTA$/25 mM NaCl, pH 7.5 with stir bar agitation. A protein precipitate formed which consisted primarily of yeast proteins with a small amount of rBoNTF($H_C$) product (approximately 10%). The precipitate was removed by centrifugation at 6000 g for 10 min at 4° C. with a Sorval SS-34 rotor Fortunately, when the pool of Mono S column fractions was diluted with ammonium sulfate, most of the rBoNTF($H_C$) product remained in solution (approximately 90%) while significant quantities of pichia proteins salted out. The first step enriched the desired product from <0.5 to 26% of the total protein (Table 2).

HIC was used as a second chromatographic step (FIG. 21B) and separated proteins based on their differences in surface hydrophobicity. It was determined that neopentyl chemistry provided the appropriate hydrophobic interaction with rBoNTF($H_C$). The supernatant was loaded onto a Pharmacia alkyl superose 10/10 hydrophobic interaction chromatography (HIC) column equilibrated with 1.5 M (NH$_4$)$_2$SO$_4$/50 mM Na$_2$HPO$_4$/2 mM Na$_2$EDTA/25 mM NaCl, pH 7.5 (buffer B) at a flow rate of 1 ml/min (75 cm/h). The column was washed with 8 ml (1 bed volume) of buffer B. Protein was eluted from the column with a linear gradient of decreasing (NH$_4$)$_2$SO$_4$ from 1.5 to 0 M over 60 ml (7.5 bed volumes). The rBoNTF(H$_C$) eluted from the HIC column at 0.92 M ammonium sulfate in a volume of 3 ml with a protein concentration of 0.52 mg/ml. Fractions positive by Western blot analysis and which only showed a single band by SDS/PAGE were pooled and dialyzed extensively in 50 mM Na$_2$HPO$_4$/2 mM Na$_2$EDTA, pH 6.8.

The recovery of purified product from cell extract was estimated to be greater than 42%, with a yield of 140 mg/kg of cell paste (Table 2). The resulting rBoNTF(H$_C$) was judged to be greater than 98% pure as only a single band was detected by SDS-PAGE (FIG. 20) even when moderately (4 µg) overloaded. Capillary isoelectric focusing showed the antigen possessed an isoelectric point of 9.4 (data not shown), which is in reasonable agreement with the calculated pI of 9.1.

TABLE 2

Purification of soluble rBoNTF(Hc)
Total protein concentration was determined by
Pierce BCA ™ assay. rBoNTF(H$_c$) was
identified by Western blot analysis and purity was
estimated by analysis of individual lanes of SDS/PAGE
by pixel densitometry using NIH imaging software.

| Step | Concentration (mg/ml) | Protein (mg) | rBoNTF(Hc) (mg) | Purity (%) | Fold Purification | Recovery (%) |
|---|---|---|---|---|---|---|
| Lysate | 11 | 1100 | 5.6 | <0.5 | — | 3.8 |
| Dialzed extract | 7.8 | 740 | 3.7 | <0.5 | — | 66 |
| Mono S | 1.2 | 9.6 | 2.5 | 26 | >52 | 45 |
| Alyl superose | 0.52 | 1.6 | 1.6 | 100 | 3.8 | 29 |

CD of Purified Soluble and Resolubilized rBoNTF(H$_C$)

Purified soluble and resolubilized rBoNTF(H$_C$) were subjected to CD spectroscopy in a Jasco 600 spectropolarimeter (Japan Spectroscopy company, Tokyo, Japan). Experiments were performed at a concentration of 30 µg/ml (0.62 µM) in a 1 cm path length cell in 10 mM Na$_2$HPO$_4$, pH 7.0. Spectra were obtained as an average of four accumulations, scanned from 260–200 nm, at a scan rate of 10 nm/min, with a 2 sec response, and a 1 nm band width. The temperature was maintained at 20° C. with a Peltier thermocontrol device.

Analysis of the far-UV circular dichroism spectrum (FIG. 22) of the purified antigen showed a positive peak at 233 nm and a minimum at 214 nm. This suggests the molecule is in a folded conformation and possesses considerable β-sheet.

Example 5

Purification of Resolubilized rBoNTF(H$_C$)

Western blot analysis revealed that approximately 30–40% of the total expressed rBoNTF(H$_C$) was present in the insoluble pellet after cell lysis. To investigate whether this insoluble protein could be recovered, the pellet was extracted in the denaturant urea and then dialyzed in non-denaturing buffer.

FPLC purification of resolubilized rBoNTF(H$_C$) The cell lysate pellet was resuspended into 20 ml of 3 M urea/50 mM Na$_2$HPO$_4$, pH 7.0 and extracted 15 h at 4° C. on a Labquake rotator. The cellular components not solubilized by the denaturing buffer were removed by centrifugation with a Sorval SS-34 rotor at 15000 g for 10 min at 4° C. The supernatant was dialyzed extensively using 10 kDa MWCO Pierce Slide-A-Lyzer dialysis cassettes in buffer A. A slight precipitate formed during the dialysis which was removed by centrifugation as described above. Western blot analysis showed that rBoNTF(H$_C$) was present only in the supernatant, which was estimated to be about 35% pure by SDS/PAGE. The supernatant was loaded onto a Pharmacia HR 10/10 Mono S cation-exchange column and separated by the same conditions as above. Fractions containing only a single positive rBoNTF(H$_C$) band SDS/PAGE and Western blot analysis were pooled and dialyzed in 50 mM Na$_2$HPO$_4$/2 mM Na$_2$EDTA, pH 6.8 in 10 kDa MWCO dialysis cassettes. The final resolubilized rBoNTF(H$_C$) product was judged to be greater than 98% pure as determined by SDS/PAGE.

Figure 22:
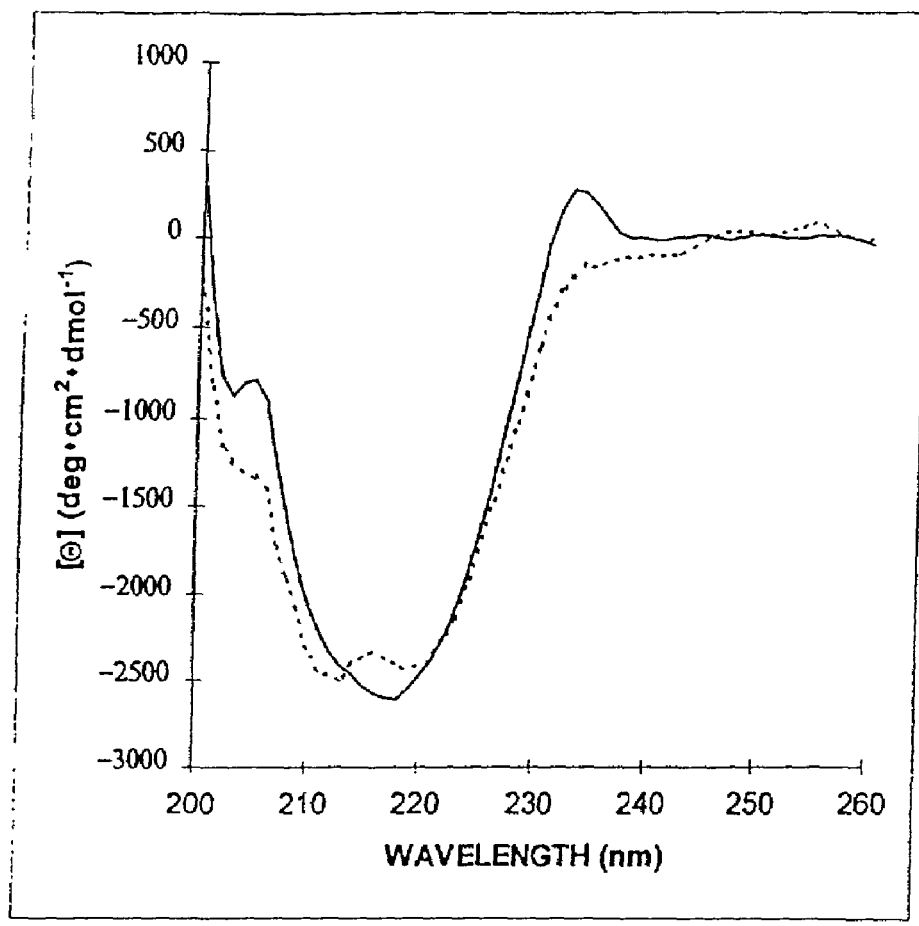
FIG. 22 shows CD spectra of purified soluble (–) and resolubilized (–) rBoNTF(Hc) at 30 µg/ml (0.62 µM) in 10 mM sodium phosphate, pH 7.0 in a 1-cm path length cell. Spectra were the average of four accumulations, scanned from 260 to 200 nm at a scan rate of 10 nm/min with a 2-s response and a 1-nm bandwidth. The temperature was maintained at 20° C. using a Peltier thermocontrol device.

After a single cation exchange chromatography separation step, the rBoNTF(H$_C$) was greater than 98% pure as judged by SDS-PAGE. The total yield of purified resolubilized rBoNTF(H$_C$) was 100 mg/kg of cell paste. The conformation of purified resolubilized antigen showed significant β-sheet as determined by CD spectral analysis (FIG. 22). However, the overall fold appeared slightly different than that shown by rBoNTF(H$_C$) purified from the cell lysate supernatant. The primary difference was the lack of a positive peak at 233 nm, indicating differences in β-sheet content.

Example 6

Mouse Immunogenicity and Efficacy Studies

To assess the immunogenicity of the recombinant rBoNTF(H$_C$), mice were inoculated with either one, two, or three doses of purified rBoNTF(H$_C$) from the soluble fraction of lysate at doses ranging from 0.008 to 5 µg per mouse.

Mouse Inoculations and BoNTF Toxin Challenge

Mice, Crl:CD-1, ICR mice (Charles River, N.C., U.S.A.) weighing 16–22 g on receipt, were injected intramuscularly (i.m.) with purified rBoNTF(H$_C$). Mice were challenged intraperitoneally (i.p.) 21 days after their last rBoNTF(H$_C$) injection with BoNTF toxin complex (Langeland strain) diluted in 0.2% (w/v) gelatin/0.4% (w/v) Na$_2$HPO$_4$, pH 6.2, in 100 µl total volume per mouse. Groups of five naive mice were also used as toxin controls. Mice were observed daily and deaths were recorded five days post challenge. All animal manipulations were in accordance with applicable regulations in AAALAC-accredited facilities.

The efficacy of the purified soluble rBoNTF(H$_C$) was determined by inoculating groups of five female mice with one, two, or three doses of 0.008, 0.04, 0.2, 1.0, or 5.0 µg rBoNTF(H$_C$) (diluted in 100 µl of 0.2% (v/v) Alhydrogel (Superfos Biosector, Kvistgaard, Denmark) in 0.9% (w/v) saline) per mouse at 14 day intervals. Two days before challenge, mice were bled retroorbitally and serum was collected for ELISA testing. Mice were challenged with 1000 mouse i.p. LD$_{50}$ of BoNTF toxin complex.

All of the mice, including five naive controls, were challenged with 1000 mouse ip LD$_{50}$ of BoNTF toxin. The controls all died within 24 h. A dose response was observed from groups of mice receiving different numbers of inoculations (Table 3). A single inoculation of 5 µg protected four of five mice, while a dose of 0.2 µg or below protected one or no mice. Two and three inoculations protected four of five and five of five mice at doses of 0.2 and 0.04 µg, respectively. At all dose levels studied, the number of surviving mice increases with the number of inoculations.

Serum antibody titers for each individual mouse were determined by ELISA, followed by calculation of the geometric mean titers for each group in the study.

Mouse Serum ELISA

Individual mouse serum ELISAs were performed as previously described (Byrne, 1998) except for the following differences Botulinum neurotoxin serotype F (Langeland strain, Food Research Institute, University of Wisconsin, Madison, Wis., U.S.A.) was used as the coating antigen and the positive control for each assay was a mouse IgG monoclonal antibody, 7F8.G2.H3 (Brown, D. R., et al., (1997), "Identification and Characterization of a Neutralizing Monoclonal Antibody Against Botulinum Neurotoxin, Serotype F, Following Vaccination with Active Toxin," *Hybridoma*, 16:447456).

TABLE 3

Survival, antibody group ELISA titers, and serum neutralization titers of mice after inoculation with purified soluble rBoNTF($H_c$)
Mice were challenged with 1000 i.p. $LD_{50}$ BoNTF toxin 21 days after last inoculation. Antibody ELISA titers were measured as the reciprocal of the highest dilution having an $OD_{405}$ greater than 0.2 AU after correcting for background. Geometric mean ELISA titers were determined by taking the geometric mean of the logarithm of the individual titers. Standard deviations of the geometric means are also reported. If the ELISA titer was determined to be below the detection limit of the assay (<100), the ELISA titer was arbitrarily assigned a value of 25. A geometric mean titer value of 1.4 means that all ELISA titers within that group were below the detection limit.

| Vaccination | Survival (alive/5 tested) | | | Geometric mean ELISA titers | | |
|---|---|---|---|---|---|---|
| dose (µg) | 1X | 2X | 3X | 1X | 2X | 3X |
| 0.008 | 0* | 0 | 2 | 1.4 | 1.4 | 1.6 ± 0.3 |
| 0.04 | 0 | 1 | 4 | 1.4 | 1.5 ± 0.3 | 2.4 ± 0.8 |
| 0.2 | 1 | 4 | 5 | 1.4 | 2.1 ± 0.9 | 2.9 ± 1.3 |
| 1.0 | 2 | 5 | 5 | 1.4 | 2.8 ± 0.3 | 4.3 ± 0.3 |
| 5.0 | 4 | 4 | 5 | 1.6 ± 0.3 | 2.8 ± 0.9 | 4.1 ± 0.5 |

*Only four mice were tested within this group

Statistical Analysis

The logistic regression model was used to test associations of geometric mean ELISA titers and individual titers with survival by using SAS, version 6.10. Geometric mean titers correlated well with protection (Table 3). The three groups with no survivors had geometric means titers below the detection limit of the assay (1.4). Similarly, the four groups that showed complete protection had geometric means titers of 2.8 or greater. Individual mouse antibody titers correlated extremely well with protection (Table 4). Only 7 out of 38 mice survived whose titers were below 100. On the other hand, 34 out of 34 survived whose titers were 100 or greater. One mouse in the study could be classified as a "nonresponder." The mouse, receiving two injections at the highest dose level, had an antibody titer below the detection limit and did not survive the BoNTF challenge. The rest of the mice in that particular group had titers of 1600 or greater.

TABLE 4

Correlation of individual antibody ELISA titer with protection after inoculation with purified soluble rBoNTF($H_c$)
Serum was bled from each mouse individually. Titer is reciprocal of the highest dilution having an $OD_{405}$ greater than 0.2 AU after correcting for background. Mice were challenged with 1000 i.p. $LD_{50}$ BoNTF toxin 21 days after last inoculation.

| Individual ELISA titer | Survival (alive/total)* | % survival |
|---|---|---|
| <100 | 7/38 | 18.4 |
| 100 | 7/7 | 100 |
| 400 | 4/4 | 100 |
| 1600 | 11/11 | 100 |
| 6400 | 3/3 | 100 |
| 25600 | 9/9 | 100 |

*The individual antibody titers from three mice were not measured. Two mice did not offer enough serum and one mouse was not challenged.

The resolubilized antigen was also evaluated for immunogenicity and protective efficacy by its ability to protect mice from a BoNTF toxin challenge. Groups of 10 male mice each received three inoculations of either 1 fig or 5 µg of rBoNTF($H_c$) (diluted in 100 µl 0.2% (v/v) Alhydrogel in 0.9% (w/v) saline) per mouse at 14 day intervals. Two days before challenge, mice were bled retroorbitally and serum was collected for ELISA testing Mice inoculated with 1 µg doses were challenged with 5000 mouse ip $LD_{50}$ of BoNTF toxin. Ten of ten mice survived the challenge. Because 100% protection was observed with the group inoculated with 1 µg doses, the group that received three doses of 5 µg were subjected to a challenged level two orders of magnitude greater in order to test the limits of the antigen. Therefore, the 5 µg dose group was challenged with 500,000 mouse ip LD50 of BoNTF toxin. None of the mice survived the challenge; however, a significant delay in time to death was observed (24–48 h). All the control mice succumbed within 24 h after challenge.

Example 7

Synthesis and Clonining of a Synthetic Gene Encoding rBoNTA ($H_C$)

The preparation of genetically engineered proteins to provide protection from the toxins produced by *Clostridium botulinum* was accomplished in *E. coli*.

Restriction endonucleases and DNA modifying enzymes were obtained from GIBCO BRL (Gaithersburg, Md.). Polymerase chain reaction (PCR) reagents were purchased from Perkin-Elmer Cetus (Norwalk, Conn.). SDS PAGE precast gels and running buffers were acquired from Amersham (Arlington Heights, Ill.). All oligonucleotides were synthesized by Macromolectular Resources (Ft. Collins, Colo.). ELISA reagents were obtained in house or from Sigma (St. Louis, Mo.) or Kirkegard and Perry Laboratories (Gaithersburg, Md.).

The *Escherichia coli* host was K12DH5a, purchased as competent cells from GIBCO BRL. Expression vectors pMAL from New England Biolabs (Beverly, Mass.) and pKK233-2 from Pharmacia LKB (Piscataway, N.J.) were used according to the manufacturers' standard protocols. The DNA clone coding of the $H_C$ domain of *c. botulinum* toxin serotype A was pCBA3, kindly provided by Nigel Minton.

Oligonucleotide primers incorporating appropriate terminal restriction enzyme sites were used to PCR amplify the $H_C$ region of the C. botulinum clone pCBA3. Gel-purified insert DNA and vector DNA were cleaved with the appropriate restriction enzymes, purified on low melting point agarose, and ligated overnight at room temperature. Competent DH5a host cells were transformed according to suppliers recommendations and plated on LB plates with 100 ug/ml ampicillin. Protein electrophoresis was run on precast 11–20% SDS PAGE at the manufacturer's recommended parameters. ELISA plates were incubated with capture antibody (horse anti-botulinum A polyclonal serum) overnight, then blocked with skim milk prior to application of various dilutions of test material, signal antibody (rabbit antibotulinum A polyclonal serum), signal HRP conjugated anti-(rabbit IgG) and ABTS substrate solution. Plates were read on an automated reader at 405 nm.

The sequence of the C fragment of the A chain was deduced as SEQ ID NO:38.

The C fragment protein sequence was reverse translated using E. coli optimal codon usage. The gene was then altered in many places to insert restriction sites, start codon, stop codon. Other changes were also effected to make the molecule more appropriate for use in the vector. Throughout, the fidelity of the protein sequence generated therefrom was maintained.

The sequence for the synthetic gene is SEQ ID NO:37.

This gene has been synthesized using a large number of oligomers of approximately 60–65 bases corresponding to the sequences of the + and − strands. The oligomers had overlaps of 7 bases. The oligomers were allowed to anneal and were ligated to form 5 subunits of 250–300 base pairs each. Each subunit had been designed to have restriction sites at their termini which allowed them to be assembled in the right order to form the complete gene. On confirmation there was shown that the correct gene had 7 deletion errors. These errors were repaired using in vitro mutagenesis and the repair sites sequenced to confirm.

Example 8

Synthesis and Cloning of a Synthetic Gene Encoding rBoNTB ($H_C$)

The C fragment for botulism toxin serotype B of Whelan was studied and the portion of the protein having the sequence of SEQ ID NO:40 (amino acids 853 to 1291 of Accession No. M81186) was defined as the C fragment.

The synthetic gene for expression in E. coli was produced in the manner described for synthesis of the gene for the C fragment of the A strand, namely, using a large number of oligomers of approximately 60–65 bases corresponding to the sequences of the + and − strands with overlaps of 7 bases. The oligomers were allowed to anneal and were ligated to form subunits of 250–300 base pairs each. Each subunit had been designed to have restriction sites at their termini which allowed them to be assembled in the right order to form the complete gene. The synthetic gene encoding the C fragment of the B toxin is SEQ ID NO:39.

Cloning:

Supernatants of sonicated, IPTG-induced recombinant pMAL fusion E. coli cultures were tested for the presence of the botulinum $H_C$ expression product by ELISA and SDS-PAGE gels stained with coomassie brilliant blue were unsuccessful. Attempts to express $H_C$ fragment as a non-fusion product were unsuccessful. Initial characterization of plasmid DNA from putative clones in pKK233-2 demonstrated an insert of the expected size was present. In addition, SDS-PAGE indicated the presence of a protein of approximately 50 kDa after induction. However, the recombinants appeared unstable and further preparations of this and other cultures failed to reproduce these results. This approach was subsequently abandoned in favor of the fusion product expression.

Example 9

Immunization Trials

Although attempts to quantitate expressed $H_C$ fusion products were unsuccessful, limited immunization trials were performed on mice to evaluate the vaccine potential of the product. Initial vaccination employed concentrated, crude E. coli lysate with complete Freund's adjuvant. Two weeks later, animals were boosted with amylose column-purified expression product with Freund's incomplete adjuvant. At this time, a second group of five animals received amylose purified product in Freund's incomplete adjuvant as a single vaccination. After two additional weeks, both groups were challenged intraperitoneally with a dose of 3 $LD_{50}$ of toxin. All eleven animals receiving two immunizations with HE survived while six of the twelve control animals receiving pMAL vector alone died.

Likewise, all five animals receiving one $H_C$ vaccination survived while animals receiving the pMAL vector alone died.

Four weeks after the initial challenge with 3 $LD_{50}$ of toxin, nine of the eleven animals who had received two immunizations were exposed to 30, 300, or 1200 $LD_{50}$ doses of toxin. The animals succumbing to the toxin challenge of 30 and 300 $LD_{50}$ did not exhibit fatality typical of botulinum toxin poisoning in that they appeared healthy after 18 hours, but were dead a few hours thereafter. In contrast, the animal which died from the 1200 $LD_{50}$ dose appeared moribund when examined at 18 hours and remained so until death. This reaction is consistent with symptoms usually observed with botulinum toxin-induced paralysis. Additional data on second challenge is shown on Table 5. Hence, it was shown that immunization with the genetically engineered toxin protected against large doses of the toxin.

It is also possible to produce antibodies using the genetically engineered toxin. Because the toxin is not disease-producing in the animal, it is possible to produce large amounts of antitoxin more cheaply. It is also possible to produce antitoxin using hybridoma technology.

TABLE 5

PROTECTION OF MICE IMMUNIZED WITH $H_c$ OF A TOXIN DERIVED FROM SYNTHETIC GENE (# of deaths/total animals)

| Calculated challenge dose ($LD_{50}$) | Control (vector without insert) | Protected (Vector with insert) |
|---|---|---|
| 4 | 2/3 | 0/3 |
| 10 | | 0/3 |
| 30 | 3/4 | 0/3 |
| 100 | | 0/3 |
| 300 | | 0/3 |
| 1000 | | 0/3 |
| 3000 | 0/1 | |

The animals received vaccinations of crude lysated cell material at 0, 2 and 4 weeks. Challenges were administered intraperitoneally with serotype A toxin at 5 weeks.

Example 10 rBoNTA($H_C$) Purification and Protective Effect

Recombinant BoNTA($H_C$) peptide was produced recombinantly in yeast. The first step in the purification process for BoNTA(H$_C$) was a Streamline expanded bed chromatography column. The product was eluted by a sodium chloride step gradient. Product eluted from the expanded bed chromatography column was estimated to be 10% pure with a total protein concentration of 0.92 mg/ml. After dialyzing the salt away, the material was loaded onto a mono S cation exchange column for further purification. Western blot and ELISA data indicated that BoNTA(H$_C$) eluted from the column at 110 mM sodium chloride. The Mono S pool was subjected to HIC as a final purification step and thus, the material was adjusted to 1.5 M ammonium sulfate. The Mono S product was loaded onto a HIC column and eluted with a gradient of decreasing ammonium sulfate. Product eluted at 1.04 M ammonium sulfate and BoNTA(H$_C$) immunologically positive fractions were combined and dialyzed to remove ammonium sulfate. Only a 50 kDa BoNTA(H$_C$) band was detected by SDS-PAGE and Western blot analysis and was judged to be greater than 95% pure after the final step. Protective effect of this purified material was measured by immunizing mice with 1 dose followed by challenge with 1000 LD50 of BoNTA(H$_C$). The results are shown in Table 6 below.

TABLE 6

Potency assay: 1 dose followed by challenge with 1000 LD50 of BoNTA(H$_c$)

| Dose (µg) | survival |
|---|---|
| 10 | 10/10 |
| 2.5 | 10/10 |
| 0.625 | 10/10 |
| 0.156 | 7/10 |
| 0.039 | 2/10 |
| 0.0098 | 0/10 |
| 0.0024 | 0/10 |

Example 11 rBoNTB(H$_C$) Purification and Protective Effect

Recombinant BoNTC(H$_C$) peptide was produced recombinantly in yeast. The first separation technique employed for the purification process for BoNTB(H$_C$) was Streamline chromatography (Pharmacia), which is a single pass expanded bed adsorption operation where proteins can be recovered from crude feed stock or cell lysate without prior clarification. Significant clean-up was accomplished in this step as the MES buffer system prohibited binding of a large percentage of unwanted proteins to the SP resin. Protein was loaded onto the column at a concentration of 123 mg/mL-resin, using 20 mM MES buffer, pH 5.7 with 10 mM NaCl. The product pool was eluted in a single step. Under the conditions investigated, on average 3.9% of the total protein loaded was recovered in the elution peak, and the product pool was approximately 70% BoNTB(H$_C$) fragment based on SDS-PAGE.

The second chromatography step in the process utilizes Poros HS, another strong cation exchange resin. The buffer system was similar to that used for Streamline SP, however enhanced selectivity of Poros HS enriched the product peak to about 85% purity. The product peak eluted during the gradient at approximately 130 mM NaCl. Strongly bound proteins were eluted with 1 M NaCl.

The final chromatography step utilized a Poros PI column. Analysis of the PI fractions by SDS-PAGE and IEF revealed that the product band, a single band at 50 kD on SDS-PAGE, was present in the pH 8.0 fraction. Analysis of purified BoNTB(H$_C$) fragment by 2-D electrophoresis resulted in one major spot and two minor, faint spots from the PI-peak 1 fraction. Peak 2 contained several spots at two different molecular weights corresponding to 50 kD and 47 kD. Presumably these spots represent different isoforms. IEF banding patterns detected in the first dimension are in agreement with those seen in Phast IEF for the two peaks. The protective efficacy of this material was determined by potency assay of 1 dose followed by challenge with 1000 LD50 of BoNTB(H$_C$). The results are shown in the following Table 7.

TABLE 7

BoNTB(H$_c$)

| Dose (µg) | survival |
|---|---|
| 10 | 10/10 |
| 2.5 | 10/10 |
| 0.625 | 10/10 |
| 0.156 | 6/10 |
| 0.039 | 1/10 |
| 0.0098 | 0/10 |
| 0.0024 | 0/10 |

Example 12 rBoNTC(H$_C$) Purification and Protective Effect

Recombinant BoNTC(H$_C$) peptide was produced recombinantly in yeast. The initial chromatography step used for the purification process for BoNTC$_1$(H$_C$) was a Mono Q anion-exchange column. The column was equilibrated with 50 mM sodium phosphate, 0.2% (W/V) CHAPS, 2 mM EDTA, pH 7.0. The CHAPS was incorporated into the column buffers to allow product to elute from the column over a narrower sodium chloride concentration. Fractions positive for BoNTC$_1$(H$_C$) by Western analysis were pooled and adjusted to 1 M ammonium sulfate. A moderate precipitate formed which was removed by passing the material through a 0.2µ filtration unit. The clarified Mono Q product pool was subjected to hydrophobic interaction chromatography using a Pharmacia alkyl superose column. This final step removed the remainder of the impurities liberating BoNTC$_1$(H$_C$) product which was estimated to be greater than 98% pure as judged by SDS/PAGE. Protective effect of this purified material was measured by immunizing mice with 1 dose followed by challenge with 1000 LD50 of BoNTC$_1$(H$_C$). The results are shown in Table 8 below.

TABLE 8

Potency Assay: One dose followed by challenge with 1000 LD50 of BoNTC$_1$(Hc)

| Dose (µg) | Survival |
|---|---|
| 8.1 | 10/10 |
| 2.7 | 10/10 |
| 0.9 | 10/10 |
| 0.3 | 9/10 |
| 0.1 | 4/10 |
| 0.033 | 0/10 |
| 0.011 | 0/10 |

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, immunology, hybridoma technology, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

TABLE 1

PICHIA CODON USAGE TABLE
From: Pichia A0X1.gene
REFORMAT of: aox1atruc.dat check: 7028
from: 1 to: 1992 27-MAY-1987 11:40
From: Pichia A0X2 gene
REFORMAT of: aox2strpk.dat check: 9641
from: 1 to: 1992 27-MAY-1987 11:41
From: Pichia 0AS1 gene
REFORMAT of: das1struc.dat check: 3191
from: 1 to: 2124 22-APR-1987 15:08
From: Pichia DAS2 gene
REFORMAT of: das2struc.dat check: 5478
from: 1 to: 2124 15-JUN-1987 14:33
From: Pichia GAP gene
REFORMAT of: pgapstruc.dat check: 9059
from: 1 to: 1002 15-JUN-1987 14:38

| AmAcid | Codon | Number | Fraction |
|---|---|---|---|
| Gly | GGG | 0.00 | 0.00 |
| Gly | GGA | 59.00 | 0.22 |
| Gly | GGT | 197.00 | 0.74 |
| Gly | GGC | 9.00 | 0.03 |
| Glu | GAG | 112.00 | 0.58 |
| Glu | GAA | 80.00 | 0.42 |
| Asp | GAT | 56.00 | 0.32 |
| Asp | GAC | 118.00 | 0.68 |
| Val | GTG | 10.00 | 0.05 |
| Val | GTA | 8.00 | 0.04 |
| Val | GTT | 107.00 | 0.50 |
| Val | GTC | 87.00 | 0.41 |
| Ala | GCG | 1.00 | 0.00 |
| Ala | GCA | 25.00 | 0.10 |
| Ala | GCT | 147.00 | 0.80 |
| Ala | GCC | 71.00 | 0.29 |
| Arg | AGG | 2.00 | 0.01 |
| Arg | AGA | 111.00 | 0.79 |
| Ser | AGT | 8.00 | 0.04 |
| Ser | AGC | 3.00 | 0.02 |
| Lys | AAG | 145.00 | 0.79 |
| Lys | AAA | 38.00 | 0.21 |
| Asn | AAT | 18.00 | 0.13 |
| Asn | AAC | 119.00 | 0.87 |
| Met | ATG | 60.00 | 1.00 |
| Ile | ATA | 0.00 | 0.00 |
| Ile | ATT | 93.00 | 0.58 |
| Ile | ATC | 72.00 | 0.44 |
| Thr | ACG | 5.00 | 0.03 |
| Thr | ACA | 8.00 | 0.05 |
| Thr | ACT | 86.00 | 0.50 |
| Thr | ACC | 74.00 | 0.43 |
| Trp | TGG | 39.00 | 1.00 |

TABLE 1-continued

PICHIA CODON USAGE TABLE
From: Pichia A0X1.gene
REFORMAT of: aox1atruc.dat check: 7028
from: 1 to: 1992 27-MAY-1987 11:40
From: Pichia A0X2 gene
REFORMAT of: aox2strpk.dat check: 9641
from: 1 to: 1992 27-MAY-1987 11:41
From: Pichia 0AS1 gene
REFORMAT of: das1struc.dat check: 3191
from: 1 to: 2124 22-APR-1987 15:08
From: Pichia DAS2 gene
REFORMAT of: das2struc.dat check: 5478
from: 1 to: 2124 15-JUN-1987 14:33
From: Pichia GAP gene
REFORMAT of: pgapstruc.dat check: 9059
from: 1 to: 1002 15-JUN-1987 14:38

| AmAcid | Codon | Number | Fraction |
|---|---|---|---|
| End | TGA | 0.00 | 0.00 |
| Cys | TGT | 35.00 | 0.83 |
| Cys | TGC | 7.00 | 0.17 |
| End | TAG | 1.00 | 0.20 |
| End | TAA | 4.00 | 0.80 |
| Tyr | TAT | 18.00 | 0.12 |
| Tyr | TAC | 128.00 | 0.88 |
| Leu | TTG | 120.00 | 0.52 |
| Leu | TTA | 21.00 | 0.09 |
| Phe | TTT | 24.00 | 0.19 |
| Phe | TTC | 104.00 | 0.81 |
| Ser | TCG | 8.00 | 0.03 |
| Ser | TCA | 14.00 | 0.07 |
| Ser | TCT | 89.00 | 0.47 |
| Ser | TCC | 71.00 | 0.37 |
| Arg | CGG | 2.00 | 0.01 |
| Arg | CGA | 0.00 | 0.00 |
| Arg | CGT | 26.00 | 0.18 |
| Arg | CGC | 0.00 | 0.00 |
| Gln | CAG | 31.00 | 0.34 |
| Gln | CAA | 59.00 | 0.66 |
| His | CAT | 11.00 | 0.13 |
| His | CAC | 77.00 | 0.88 |
| Leu | CTG | 35.00 | 0.15 |
| Leu | CTA | 7.00 | 0.03 |
| Leu | CTT | 43.00 | 0.18 |
| Leu | CTC | 7.00 | 0.03 |
| Pro | CCG | 0.00 | 0.00 |
| Pro | CCA | 97.00 | 0.57 |
| Pro | CCT | 68.00 | 0.39 |
| Pro | CCC | 7.00 | 0.04 |

We claim:

1. An isolated or purified nucleic acid sequence encoding a polypeptide comprising the amino acid sequence of SEQ ID NO:8, wherein said nucleic acid sequence is obtained by genetic engineering and designed by selecting at least a portion of the codons of said nucleic acid sequence from codons preferred for expression in a host cell.

2. The nucleic acid of claim 1, wherein said nucleic acid comprises nucleotides 10–1332 of SEQ ID NO:7.

3. The nucleic acid of claim 1, further comprising an expression control sequence operably linked to said nucleotide sequence.

4. The nucleic acid of claim 3, wherein said expression control sequence comprises a promoter.

5. The nucleic acid of claim 3, wherein said expression control sequence comprises an enhancer.

6. The nucleic acid of claim 1, wherein the AT content is less than about 70% of the total base composition.

7. The nucleic acid of claim 6, wherein the AT content is less than about 60% of the total base composition.

8. An isolated host cell comprising the nucleic acid of claim 3, wherein said nucleic acid is expressed.

9. The isolated host cell of claim 8, wherein said nucleic acid is expressed as a polypeptide, wherein said polypeptide is at least 0.75% (w/w) of the total cellular protein.

10. The isolated host cell of claim 9, wherein said polypeptide is at least 20% (w/w) of the total cellular protein.

11. A method of isolating an immunogenic polypeptide comprising the amino acid sequence of SEQ ID NO:8, comprising:
   culturing a cell transfected with an expression vector comprising a nucleic acid sequence encoding a polypeptide comprising the amino acid sequence of SEQ ID NO:8, wherein said nucleic acid sequence is obtained by genetic engineering and designed by selecting at least a portion of the codons of said nucleic acid sequence from codons preferred for expression in a host cell, under conditions wherein the nucleic acid sequence is expressed; and
   isolating from said transfected cell at least one insoluble polypeptide comprising the amino acid sequence of SEQ ID NO:8,
   wherein the cell is selected from the group consisting of a gram negative bacterium, a yeast cell, and cell of a mammalian cell line and wherein the isolated polypeptide is immunogenic.

12. A method of preparing a polypeptide comprising a carboxy-terminal portion of the heavy chain of botulinum neurotoxin serotype B, comprising:
   transfecting a cell with a nucleic acid sequence encoding a polypeptide comprising the amino acid sequence of SEQ ID NO:8, wherein said nucleic acid sequence is obtained by genetic engineering and designed by selecting at least a portion of the codons of said nucleic acid sequence from codons preferred for expression in a host cell; and
   culturing the transfected cell under conditions wherein the nucleic acid is expressed and the polypeptide comprising the amino acid sequence of SEQ ID NO:8 is produced,
   wherein the cell is selected from the group consisting of a gram negative bacterium, a yeast cell, and cell of a mammalian cell line.

13. The method of claim 12, further comprising recovering from said transfected cell at least one insoluble polypeptide comprising the amino acid sequence of SEQ ID NO:8.

14. The method of claim 12, wherein said cell is *Escherichia coli*.

15. The method of claim 12, wherein said cell is *Pichia pastoris*.

16. An isolated nucleic acid comprising nucleotides 10–1332 of SEQ ID NO:7.

17. The isolated nucleic acid of claim 16, wherein said nucleic acid comprises SEQ ID NO: 7.

\* \* \* \* \*